US012618016B2

(12) United States Patent
Malinski et al.

(10) Patent No.: US 12,618,016 B2
(45) Date of Patent: May 5, 2026

(54) METHODS FOR PRODUCING AVIATION FUELS

(71) Applicant: Chevron Phillips Chemical Company LP, The Woodlands, TX (US)

(72) Inventors: Thomas J. Malinski, Kingwood, TX (US); Michael S. Webster-Gardiner, Kingwood, TX (US); Steven M. Bischof, Kingwood, TX (US); James L. Hillier, Kingwood, TX (US); Jeffery C. Gee, Kingwood, TX (US); Spencer A. Kerns, Kingwood, TX (US); Reza Khankal, Kingwood, TX (US); Jared T. Fern, Kingwood, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 18/808,193

(22) Filed: Aug. 19, 2024

(65) Prior Publication Data

US 2026/0049256 A1 Feb. 19, 2026

Related U.S. Application Data

(63) Continuation-in-part of application No. 18/462,558, filed on Sep. 7, 2023, now Pat. No. 12,540,287, and
(Continued)

(51) Int. Cl.

| | |
|---|---|
| ***C10G 69/12*** | (2006.01) |
| ***C07C 2/08*** | (2006.01) |
| ***C07C 6/04*** | (2006.01) |

(52) U.S. Cl.
CPC .............. *C10G 69/126* (2013.01); *C07C 2/08* (2013.01); *C07C 6/04* (2013.01);
(Continued)

(58) Field of Classification Search
CPC .......... C10G 69/126; C10G 2300/1092; C10G 2300/70; C10G 2400/08; C07C 2/08; C07C 6/04
See application file for complete search history.

(56) References Cited

U.S. PATENT DOCUMENTS

| | | | |
|---|---|---|---|
| 2,882,244 | A | 4/1959 | Milton |
| 3,130,007 | A | 4/1964 | Breck |

(Continued)

FOREIGN PATENT DOCUMENTS

| | | | |
|---|---|---|---|
| WO | 2002004575 | A2 | 1/2002 |
| WO | 2018071905 | A1 | 4/2018 |

(Continued)

OTHER PUBLICATIONS

Non-Final Office Action issued in U.S. Appl. No. 18/462,567, filed Sep. 7, 2023. Notification issued Mar. 20, 2025, 21 pages.

(Continued)

*Primary Examiner* — Ali Z Fadhel
(74) *Attorney, Agent, or Firm* — Merchant & Gould P.C.

(57) ABSTRACT

Processes for making aviation fuels include a step of forming a $C_{16-}$ olefin stream by oligomerizing a mixture of decenes with a $C_{6-}$ alpha-olefin or by subjecting the mixture of decenes and a $C_{8-}$ alpha-olefin to metathesis. The $C_{16-}$ olefin stream is then hydrogenated to form $C_{16-}$ paraffins, and these $C_{16-}$ paraffins can be used to form an aviation fuel. Particular $C_{11}$-$C_{16}$ olefin compositions and paraffin compositions prepared by these processes also are described.

16 Claims, 12 Drawing Sheets

2-butyl-1-hexene
5-butyl-7-methylundec-5-ene
5-butyl-7-methylundecane
3-propyl-1-heptene
(*E*)-5-methyl-8-propyldodec-6-ene
5-methyl-8-propyldodecane
4-ethyl-1-octene
(*E*)-9-ethyl-5-methyltridec-6-ene
5-ethyl-9-methyltridecane
5-methyl-1-nonene
(*E*)-5,10-dimethyltetradec-6-ene
5,10-dimethyltetradecane

Related U.S. Application Data a continuation-in-part of application No. 18/462,567, filed on Sep. 7, 2023, now Pat. No. 12,528,999.

(52) U.S. Cl.
CPC . *C10G 2300/1092* (2013.01); *C10G 2300/70* (2013.01); *C10G 2400/08* (2013.01)

(56) References Cited

U.S. PATENT DOCUMENTS

| | | | | |
|---|---|---|---|---|
| 3,216,789 | A | 11/1965 | Breck | |
| 4,021,447 | A | 5/1977 | Rubin | |
| 4,503,023 | A | 3/1985 | Breck | |
| 6,190,539 | B1 | 2/2001 | Holtermann | |
| 6,291,733 | B1 | 9/2001 | Small | |
| 6,812,180 | B2 | 11/2004 | Fukunaga | |
| 6,914,165 | B2 | 7/2005 | Flego | |
| 7,153,801 | B2 | 12/2006 | Wu | |
| 7,902,105 | B2 | 3/2011 | Khare | |
| 8,334,420 | B2 | 12/2012 | Small | |
| 8,680,003 | B2 | 3/2014 | Sydora | |
| 8,791,217 | B2 | 7/2014 | Hlavinka | |
| 8,969,640 | B2 | 3/2015 | Blommel | |
| 9,115,225 | B2 | 8/2015 | Hlavinka | |
| 9,175,109 | B1 | 11/2015 | Kreischer | |
| 9,352,309 | B2 | 5/2016 | Sydora | |
| 9,567,541 | B2 | 2/2017 | Frey | |
| 9,708,549 | B2 | 7/2017 | Gee | |
| 9,745,230 | B2 | 8/2017 | Small | |
| 9,862,655 | B2 | 1/2018 | Fichtl | |
| 9,879,192 | B2 | 1/2018 | Watermeyer De Wet | |
| 9,914,672 | B2 | 3/2018 | Greene | |
| 9,957,449 | B2 | 5/2018 | Luebke | |
| 9,968,921 | B2 | 5/2018 | Kilgore | |
| 10,113,130 | B1 | 10/2018 | Harvey | |
| 10,183,899 | B2 | 1/2019 | Bischof | |
| 10,240,102 | B2 | 3/2019 | Small | |
| 10,329,212 | B2 | 6/2019 | Fern | |
| 10,414,698 | B2 | 9/2019 | Fern | |
| 10,435,334 | B2 | 10/2019 | Bischof | |
| 10,435,336 | B2 | 10/2019 | Kreischer | |
| 10,544,070 | B2 | 1/2020 | Small | |
| 10,577,291 | B2 | 3/2020 | Frey | |
| 10,647,626 | B2 | 5/2020 | Coffin | |
| 10,647,931 | B2 | 5/2020 | Pucci | |
| 10,793,781 | B2 | 10/2020 | Hakola | |
| 10,920,151 | B2 | 2/2021 | Brandvold | |
| 10,927,052 | B2 | 2/2021 | Coffin | |
| 11,072,569 | B2 | 7/2021 | Bischof | |
| 11,078,433 | B2 | 8/2021 | Smith | |
| 11,174,205 | B2 | 11/2021 | Gee | |
| 11,186,530 | B2 | 11/2021 | Gee | |
| 11,312,671 | B2 | 4/2022 | Barias | |
| 11,358,914 | B2 | 6/2022 | Bischof | |
| 11,639,320 | B1 | 5/2023 | Chang | |
| 2009/0158637 | A1 | 6/2009 | Mccall | |
| 2009/0250376 | A1 | 10/2009 | Brandvold | |
| 2012/0197053 | A1* | 8/2012 | Cantrell | C10L 1/04 585/329 |
| 2012/0209045 | A1 | 8/2012 | Wright | |
| 2014/0051898 | A1 | 2/2014 | Wright | |
| 2016/0194257 | A1* | 7/2016 | Lilga | B01J 29/90 585/517 |
| 2018/0016204 | A1* | 1/2018 | Coffin | C07C 2/26 |
| 2018/0065115 | A1 | 3/2018 | Alvez-Manoli | |
| 2021/0009911 | A1 | 1/2021 | Medoff | |
| 2021/0355047 | A1 | 11/2021 | Li | |
| 2022/0396534 | A1 | 12/2022 | Vincent | |
| 2022/0396741 | A1 | 12/2022 | Vincent | |
| 2023/0313048 | A1* | 10/2023 | Jan | C10G 69/126 585/17 |
| 2024/0246887 | A1 | 7/2024 | Mathur | |

FOREIGN PATENT DOCUMENTS

| | | | |
|---|---|---|---|
| WO | 2026027733 | A1 | 2/2026 |
| WO | 2026027734 | A1 | 2/2026 |
| WO | 2026027735 | A1 | 2/2026 |
| WO | 2026027736 | A1 | 2/2026 |

OTHER PUBLICATIONS

Sustainable Aviation Fuel: Review of Technical Pathways, U.S. Department of Energy, energy.gov/eere/bioenergy, 2020, 81 pages.

Toxicological Profile for Jet Fuels JP-4 and JP-7, U.S. Department of Health and Human Services, Agency for Toxic Substances and Disease Registry, Jun. 1995, 150 pages.

Babu B Hari et al: "An integrated process for production of jet-fuel range olefins from ethylene using Ni-AISBA-15 and Amberlyst-35 catalysts", Applied Catalysis A: General, vol. 530, 2017, pp. 48-55.

Faroon et al., Toxicological Profile for Jet Fuels JP-4 and JP-7, U.S. Department of Health and Human Services. Agency for Toxic Substances and Disease Registry, Jun. 1995, 150 pages.

Holladay et al., Sustainable Aviation Fuel: Review of Technical Pathways, US Dept of Energy, Office of Energy Efficiency and Renewable Energy, Sep. 2020, 81 pages.

International Search Report and Written Opinion issued in corresponding PCT Application No. PCT/US2024/045290, mailed on Dec. 20, 2024, 16 pages.

ISCC Certification for Sustainable Aviation Fuels, ISSC System GmbH, 19 pages.

International Search Report and Written Opinion issued in corresponding PCT Application No. PCT/US2024/045299, mailed on Feb. 3, 2025, 24 pages.

Small, B., Insights on the Mechanism for Ethylene Tetramerization, Organometamcs, DOI: 10.1021/acs.organomet.2c00285, Jun. 2022, 12 pages.

Axens Oligomerization—Bio-Olefin Upgrading, Axens Renewable Paythways, 1 page.

International Search Report and Written Opinion issued in corresponding PCT Application No. PCT/US2025/042160, mailed on Nov. 21, 2025, 13 pp.

Liu et al., "Experimental and numberical analysis on flow characteristics and pyrolysis mechanism of hydrocarbon fuel with a novel online hybred method," ScienceDirect, Energy Conversion and Management, 198 (2019) 111817, 14 pp.

Gao et al.,"Novel measurement of isobaric specific heat capacity for kerosene RP-3 at high temperature and high pressure," ScienceDirect, Thermochimica Acta 638 (2016) pp. 113-119.

* cited by examiner 2-butyl-1-hexene
3-propyl-1-heptene
4-ethyl-1-octene
5-methyl-1-nonene 5-butyl-3-methylnon-4-ene
(*E*)-3-methyl-6-propyldec-4-ene
(*E*)-7-ethyl-3-methylundec-4-ene
(*E*)-3,8-dimethyldodec-4-ene 5-butyl-3-methylnonane
3-methyl-6-propyldecane
7-ethyl-3-methylundecane
3,8-dimethyldodecane 2-butyl-1-hexene 3-propyl-1-heptene 4-ethyl-1-octene 5-methyl-1-nonene 2,2-dimethyl-4-butyl-3-octene 2,2-dimethyl-5-propyl-3-nonene 2,2-dimethyl-6-ethyl-3-decene 2,2,7-trimethyl-3-undecene 5-(2,2-dimethylpropyl)nonane 2,2-dimethyl-5-propylnonane 2,2-dimethyl-6-ethyl-decane 2,2,7-trimethylundecane 2-butyl-1-hexene 3-propyl-1-heptene 4-ethyl-1-octene 5-methyl-1-nonene 6-butyl-4-methyldec-5-ene (*E*)-4-methyl-7-propylundec-5-ene (*E*)-8-ethyl-4-methyldodec-5-ene (*E*)-4,9-dimethyltridec-5-ene 6-butyl-4-methyldecane 4-methyl-7-propylundecane 8-ethyl-4-methyldodecane 4,9-dimethyltridecane 2-butyl-1-hexene
3-propyl-1-heptene
4-ethyl-1-octene
5-methyl-1-nonene 5-butyl-7-methylundec-5-ene
(*E*)-5-methyl-8-propyldodec-6-ene
(*E*)-9-ethyl-5-methyltridec-6-ene
(*E*)-5,10-dimethyltetradec-6-ene 5-butyl-7-methylundecane
5-methyl-8-propyldodecane
5-ethyl-9-methyltridecane
5,10-dimethyltetradecane 2-butyl-1-hexene
3-butyl-2-heptene
5-ethylnonane 3-propyl-1-heptene
4-propyl-2-octene
4-propyloctane 4-ethyl-1-octene
5-ethyl-2-nonene
5-ethylnonane 5-methyl-1-nonene
6-methyl-2-decene
5-methyldecane 2-butyl-1-hexene
3-propyl-1-heptene
4-ethyl-1-octene
5-methyl-1-nonene
4-butyl-3-octene
5-propyl-3-nonene
6-ethyl-3-decene
7-methyl-3-undecene
5-propylnonane
5-propylnonane
5-ethyldecane
5-methylundecane 2-butyl-1-hexene
3-propyl-1-heptene
4-ethyl-1-octene
5-methyl-1-nonene 5-(propan-2-ylidene)nonane
2-methyl-4-propyloct-2-ene
5-ethyl-2-methylnon-2-ene
2,6-dimethyldec-2-ene 5-isopropylnonane
2-methyl-4-propyloctane
5-ethyl-2-methylnonane
2,6-dimethyldecane 2-butyl-1-hexene 3-propyl-1-heptene 4-ethyl-1-octene 5-methyl-1-nonene 5-butyl-4-nonene 6-propyl-4-decene 7-ethyl-4-undecene 8-methyl-4-dodecene 5-butylnonane 5-propyldecane 5-ethylundecane 5-methyldodecane 2-butyl-1-hexene 3-propyl-1-heptene 4-ethyl-1-octene 5-methyl-1-nonene 5-butyldec-5-ene (*E*)-7-propylundec-5-ene (*E*)-8-ethyldodec-5-ene (*E*)-9-methyltridec-5-ene 5-butyldecane 5-propylundecane 5-ethyldodecane 5-methyltridecane 2-butyl-1-hexene
5-(2,2-dimethylpropylidene)nonane
5-neopentylnonane 3-propyl-1-heptene
(*E*)-2,2-dimethyl-5-propylnon-3-ene
2,2-dimethyl-5-propylnonane 4-ethyl-1-octene
(*E*)-6-ethyl-2,2-dimethyldec-3-ene
6-ethyl-2,2-dimethyldecane 5-methyl-1-nonene
(*E*)-2,2,7-trimethylundec-3-ene
2,2,7-trimethylundecane 2-butyl-1-hexene 3-propyl-1-heptene 4-ethyl-1-octene 5-methyl-1-nonene 5-butyldodec-5-ene (*E*)-5-propyltridec-6-ene (*E*)-5-ethyltetradec-7-ene (*E*)-11-methylpentadec-7-ene 5-butyldodecane 5-propyltridecane 5-ethyltetradecane 5-methylpentadecane

METHODS FOR PRODUCING AVIATION FUELS

REFERENCE TO RELATED APPLICATIONS

This application is a continuation-in-part application of co-pending U.S. patent application Ser. No. 18/462,567, filed on Sep. 7, 2023, now U.S. Pat. No. 12,528,999, and a continuation-in-part application of co-pending U.S. patent application Ser. No. 18/462,558, also filed on Sep. 7, 2023, now U.S. Pat. No. 12,540,287, the disclosures of which are incorporated herein by reference in their entirety.

FIELD OF THE INVENTION

The present disclosure generally relates to methods for making aviation fuels, and more particularly, relates to such methods that include a step of reacting particular alpha-olefins with a mixture of decenes in the presence of an oligomerization catalyst or a metathesis catalyst.

BACKGROUND OF THE INVENTION

Although the jet fuel market is smaller than the gasoline and diesel fuel markets, it still constitutes some 25% of the total transportation fuel consumption and currently exceeds 26 billion gallons per year in the U.S. alone. Market growth in jet fuels is expected to approximately double over the next 20 years, while the gasoline markets are expected to decline over this time. Therefore, maintaining a robust jet fuel production and transportation infrastructure, and developing improved processes for producing jet and aviation fuels are becoming increasingly important. Accordingly, it is to these ends that the present invention is generally directed.

Further, sustainable aviation fuels (SAF) may offer the needed resilience to meet these future needs in terms of feedstock availability, while addressing the need to reduce emissions. Not only can SAF provide a large reduction of greenhouse gas emissions with little or no changes to current engine technology, SAF may also provide a drop-in fuel solution. Drop-in fuels allow current aircraft to use a 50 percent blend of SAF and Jet A with no engine or other modifications. In addition, SAF production facilities may be located near the airports they service, which may also improve fuel transport issues for jet fuels. Therefore, many companies have set SAF use goals as a primary strategy to attain net-zero emissions.

However, challenges to the large scale production and use of SAF remain. While SAF provide an environmentally sustainable technology, current technologies to produce SAF are not yet economically viable. For example, SAF may cost four to five times as much as conventional jet fuel, and currently makes up less than one percent of fuel available in the market. Therefore, there remains a need for processes for making sustainable aviation fuels which may improve the technology, and enhance the production economics, and which may provide additional benefits or efficiencies to address the rapidly growing need for jet fuel.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

Aviation fuels and specifically jet fuels contain primarily saturated hydrocarbon compounds, including linear and branched alkanes (paraffins), and cycloalkanes (cycloparaffins or naphthenes), with smaller concentrations of aromatic compounds and olefins. The high hydrogen-to-carbon ratio of the paraffins provides a high heat release per unit weight and a relatively cleaner burn than other hydrocarbons, while cycloparaffins provide less heat release per unit of weight but increase the fuel's density. Paraffins and cycloparaffins also beneficially reduce the freezing point of the fuel.

The composition of aviation fuels is based primarily on fuel specifications which provide the maximum performance for the specific aircraft for which the fuel is used, rather than a specification based on chemical composition. The ethylene oligomerization process described herein can be used to provide products in the kerosene jet fuel range ($C_8$-$C_{16}$) or wide-cut jet fuel range ($C_5$-$C_{15}$ or $C_4$-$C_{16}$). For example, JP-4 is a wide-cut fuel because it is produced from a broad distillation temperature range and contains a wide array of carbon chain-lengths, from 4 to 16 carbons long. The approximate composition of JP-4 is about 86 vol. % saturated hydrocarbons, about 13 vol. % (v/v) aromatic hydrocarbons, about 1 vol. % olefins, and JP-4 has a distillation range of about 60° C. to 270° C.

The disclosed processes for making aviation fuels takes advantage of the selective, on-purpose production of a $C_4$-$C_8$ alpha-olefin from ethylene, in which the principal by-product is a mixture of $C_{10}$ olefins, also referred to herein as a mixture of decenes. The mixture of decenes in this normal alpha-olefin (NAO) mixture can be further subjected to oligomerization or to metathesis with an alpha-olefin to form an aviation fuel comprising $C_{16-}$ paraffins and cycloparaffins. Moreover, the mixture of decenes itself may also be hydrogenated to form a mixture of decanes which are used as a component of an aviation fuel by blending with $C_{16-}$ paraffins and cycloparaffins to provide the aviation fuel.

Previously, the by-product mixture of decenes from the ethylene oligomerization to form $C_4$-$C_8$ alpha-olefins was an undesirable product which has been sold as-is for a low-cost fuel. Thus, this relatively low-value by-product can be upgraded as described herein to produce aviation fuel. Although the ethylene oligomerization process can be highly selective, for example, for producing 1-hexene, the production of decene by-products is not selective. For example, the mixture of decenes can include 1-decene, 2-butyl-1-hexene, 3-propyl-1-heptene, 4-ethyl-1-octene, 5-methyl-1-nonene, 4-decene, and 5-decene. Whether these decenes are hydrogenated to decanes for use as an aviation fuel component or further subjected to oligomerization or metathesis and then hydrogenated to an aviation fuel, the lack of selectivity in their production does not impart any disadvantage to this mixture for an aviation fuel end-use.

Accordingly, this disclosure provides a process for making an aviation fuel. In an aspect of this invention, the process can comprise (a) contacting an ethylene feed with a first catalyst system comprising a first oligomerization catalyst to form an oligomerization product comprising at least one $C_4$-$C_8$ alpha-olefin and a mixture of decenes, (b) separating the mixture of decenes from the oligomerization product, (c) forming a $C_{16-}$ olefin stream by (i) contacting the mixture of decenes with at least one $C_{6-}$ alpha-olefin in the presence of a second catalyst system comprising a second oligomerization catalyst, or (ii) contacting the mixture of decenes with at least one $C_{8-}$ alpha-olefin in the presence of a second catalyst system comprising a metathesis catalyst, (d) optionally, hydrogenating the $C_{16-}$ olefin stream in the presence of a first hydrogenation catalyst to provide $C_{16-}$ paraffins, and (e) optionally, using the $C_{16-}$ paraffins as a component to form an aviation fuel.

In another aspect, a process for making an aviation fuel is provided, and in this aspect, the process can comprise (a) contacting an ethylene feed with a first catalyst system comprising a first oligomerization catalyst to form an oligomerization product comprising at least one $C_4$-$C_8$ alpha-olefin and a mixture of decenes, (b) separating the mixture of decenes from the oligomerization product, (c) contacting the mixture of decenes with at least one $C_{6-}$ alpha-olefin in the presence of a second catalyst system comprising a second oligomerization catalyst to provide a $C_{16-}$ olefin stream, (d) optionally, hydrogenating the $C_{16-}$ olefin stream in the presence of a first hydrogenation catalyst to provide $C_{16-}$ paraffins, and (e) optionally, using the $C_{16-}$ paraffins as a component to form an aviation fuel.

In another aspect, a process for making an aviation fuel is provided, and in this aspect, the process can comprise (a) contacting an ethylene feed with a first catalyst system comprising a first oligomerization catalyst to form an oligomerization product comprising at least one $C_4$-$C_8$ alpha-olefin and a mixture of decenes, (b) separating the mixture of decenes from the oligomerization product, (c) contacting the mixture of decenes with at least one $C_{8-}$ alpha-olefin in the presence of a second catalyst system comprising a metathesis catalyst to provide a $C_{16-}$ olefin stream, (d) optionally, hydrogenating the $C_{16-}$ olefin stream in the presence of a first hydrogenation catalyst to provide $C_{16-}$ paraffins, and (e) optionally, using the $C_{16-}$ paraffins as a component to form an aviation fuel.

In yet another aspect, a process for making an aviation fuel is provided, and in this aspect, the can comprise (a) contacting an ethylene feed with a first catalyst system comprising a first oligomerization catalyst to form an oligomerization product comprising at least one $C_4$-$C_8$ alpha-olefin and a mixture of decenes, (b) separating the mixture of decenes from the oligomerization product, (c) optionally, hydrogenating the mixture of decenes in the presence of a second hydrogenation catalyst to provide a mixture of decanes, and (d) optionally, using the mixture of decanes as a component to form an aviation fuel.

In still another aspect, a process for making an aviation fuel is provided, and in this aspect, the process can comprise (a) contacting an ethylene feed with a first catalyst system comprising a first oligomerization catalyst to form an oligomerization product comprising at least one $C_4$-$C_6$ alpha-olefin or at least one $C_4$-$C_8$ alpha-olefin and a mixture of decenes, (b) contacting the oligomerization product with a second catalyst system comprising a second oligomerization catalyst or a metathesis catalyst to provide a $C_{16-}$ olefin stream, (c) optionally, hydrogenating the $C_{16-}$ olefin stream in the presence of a first hydrogenation catalyst to provide $C_{16-}$ paraffins, and (d) optionally, using the $C_{16-}$ paraffins as a component to form an aviation fuel.

Olefin and alkane compositions produced from one or more of these processes also are encompassed herein. For instance, a $C_{13}$ olefin composition derived from propylene addition to mixed decenes can comprise 2-methyl-4-butyl-3-octene, 2-methyl-5-propylnon-3-ene, 6-ethyl-2-methyldec-3-ene, and/or 2,7-dimethylundec-3-ene, and analogous $C_{13}$ alkanes can be formed via hydrogenation. A $C_{14}$ olefin composition derived from 1-butene addition to mixed decenes can comprise 5-butyl-3-methylnon-4-ene, 3-methyl-6-propyldec-4-ene, 7-ethyl-3-methylundec-4-ene, and/or 3,8-dimethyldodec-4-ene, and analogous $C_{14}$ alkanes can be formed via hydrogenation. A $C_{14}$ olefin composition derived from isobutylene addition to mixed decenes can comprise 2,2-dimethyl-4-butyl-3-octene, 2,2-dimethyl-5-propyl-3-nonene, 2,2-dimethyl-6-ethyl-3-decene, and/or 2,2,7-trimethyl-3-undecene, and analogous $C_{14}$ alkanes can be formed via hydrogenation. A $C_{15}$ olefin composition derived from 1-pentene addition to mixed decenes can comprise 6-butyl-4-methyldec-5-ene, 4-methyl-7-propylundec-5-ene, 8-ethyl-4-methyldodec-5-ene, and/or 4,9-dimethyltridec-5-ene, and analogous $C_{15}$ alkanes can be formed via hydrogenation. A $C_{16}$ olefin composition derived from 1-hexene addition to mixed decenes can comprise 5-butyl-7-methylundec-5-ene, 5-methyl-8-propyldodec-6-ene, 9-ethyl-5-methyltridec-6-ene, and/or 5,10-dimethyltetradec-6-ene, and analogous $C_{16}$ alkanes can be formed via hydrogenation.

Further olefin and alkane compositions produced from one or more of these processes also are encompassed herein. For instance, a $C_{11}$ olefin composition derived from propylene metathesis with mixed decenes can comprise 3-butyl-2-heptene, 4-propyl-2-octene, 5-ethyl-2-nonene, and/or 6-methyl-2-decene, and analogous $C_{11}$ alkanes can be formed via hydrogenation. A $C_{12}$ olefin composition derived from 1-butene metathesis with mixed decenes can comprise 4-butyl-3-octene, 5-propyl-3-nonene, 6-ethyl-3-decene, and/or 7-methyl-3-undecene, and analogous $C_{12}$ alkanes can be formed via hydrogenation. A $C_{12}$ olefin composition derived from isobutylene metathesis with mixed decenes can comprise 2-methyl-4-propyloct-2-ene, 5-ethyl-2-methylnon-2-ene, and/or 2,6-dimethyldec-2-ene, and analogous $C_{12}$ alkanes can be formed via hydrogenation. A $C_{13}$ olefin composition derived from 1-pentene metathesis with mixed decenes can comprise 5-butyl-4-nonene, 6-propyl-4-decene, 7-ethyl-4-undecene, and/or 8-methyl-4-dodecene, and analogous $C_{13}$ alkanes can be formed via hydrogenation. A $C_{14}$ olefin composition derived from 1-hexene metathesis with mixed decenes can comprise 5-butyldec-5-ene, 7-propylundec-5-ene, 8-ethyldodec-5-ene, and/or 9-methyltridec-5-ene, and analogous $C_{14}$ alkanes can be formed via hydrogenation. A $C_{14}$ olefin composition derived from 3,3-dimethyl-1-butene metathesis with mixed decenes can comprise 5-(2,2-dimethylpropylidene)nonane, 2,2-dimethyl-5-propylnon-3-ene, 6-ethyl-2,2-dimethyldec-3-ene, and/or 2,2,7-trimethylundec-3-ene, and analogous $C_{14}$ alkanes can be formed via hydrogenation. A $C_{16}$ olefin composition derived from 1-octene metathesis with mixed decenes can comprise 5-butyldodec-5-ene, 5-propyltridec-6-ene, 5-ethyltetradec-7-ene, and 11-methylpentadec-7-ene, and analogous $C_{16}$ alkanes can be formed via hydrogenation.

If desired, the aviation fuel or a component thereof prepared as described herein can be used as-is, that is, it can be used without further purification. In another aspect, the aviation fuel or a component thereof prepared as described herein can be used following further purification by any method. Suitable purifications may be designed to remove contaminants such as sulfur compounds or may be used to fractionate the aviation fuel or component thereof to select a higher or lower boiling fraction thereof. In a further aspect, the aviation fuel or the component thereof can be blended with a sustainable aviation fuel.

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects may be directed to various feature combinations and sub-combinations described in the detailed description.

BRIEF DESCRIPTION OF THE FIGURES

The following figures form part of the present specification and are included to further demonstrate certain aspects of the present invention. The invention may be better understood by reference to one or more of these figures in combination with the detailed description of specific embodiments presented herein.

Figure 1:
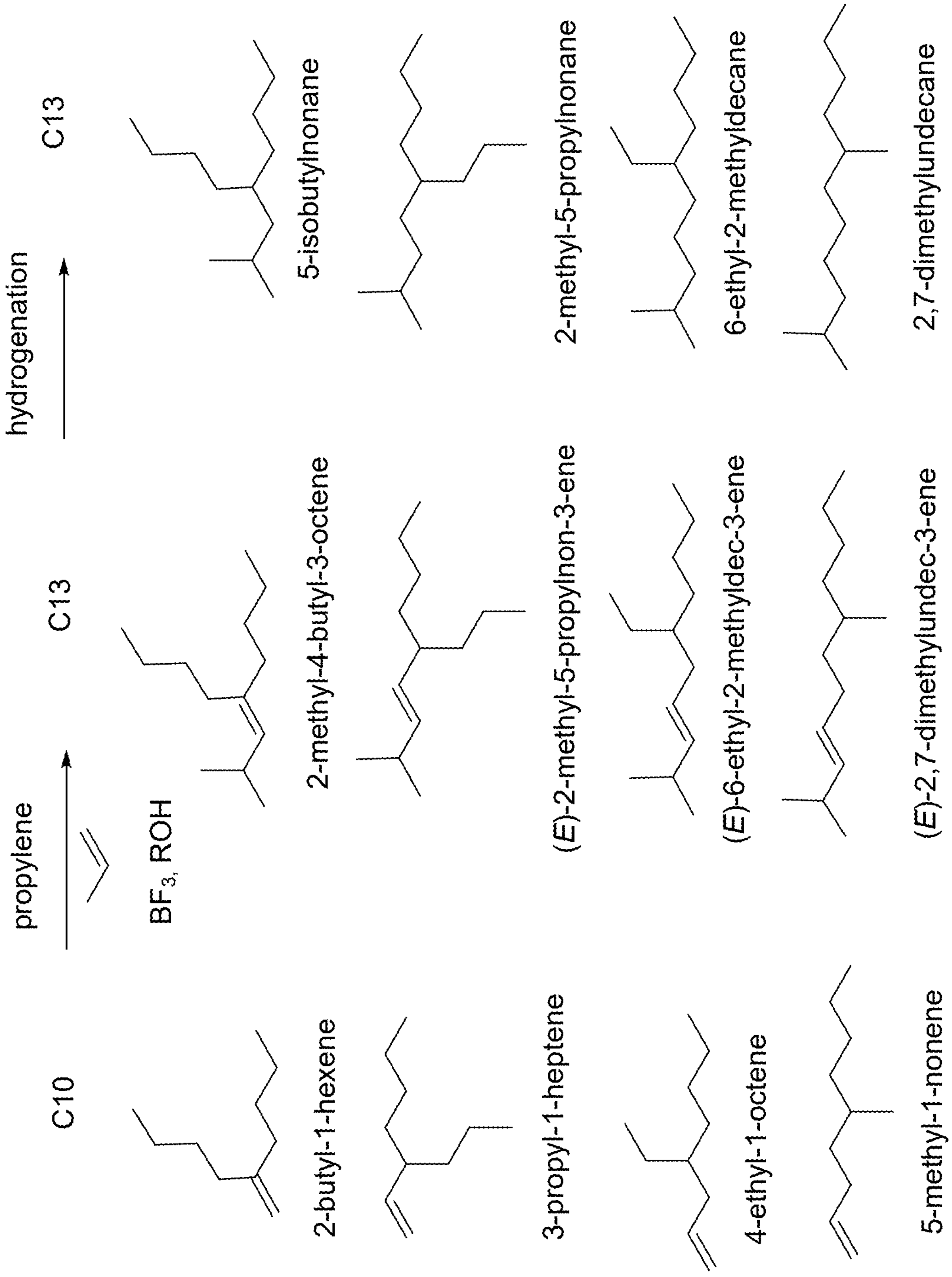
FIG. 1 is an olefin addition reaction scheme for the reaction of $C_{10}$ olefins with propylene to form $C_{13}$ olefins and subsequent hydrogenation to from $C_{13}$ alkanes.

While the inventions disclosed herein are susceptible to various modifications and alternative forms, only a few specific embodiments are described in detail below. The figures and detailed descriptions of these specific embodiments are not intended to limit the breadth or scope of the inventive concepts or the appended claims in any manner. Rather, the figures and detailed written descriptions are provided to illustrate the inventive concepts to a person of ordinary skill in the art and to enable such person to make and use the inventive concepts.

Definitions

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2$^{nd}$ Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter are described such that, within particular aspects, a combination of different features can be envisioned. For each and every aspect and each and every feature disclosed herein, all combinations that do not detrimentally affect the processes or methods described herein are contemplated with or without explicit description of the particular combination. Additionally, unless explicitly recited otherwise, any aspect or feature disclosed herein can be combined to describe inventive processes or methods consistent with the present disclosure.

Generally, groups of elements are indicated using the numbering scheme indicated in the version of the periodic table of elements published in *Chemical and Engineering News,* 63(5), 27, 1985. In some instances, a group of elements can be indicated using a common name assigned to the group; for example, alkali metals for Group 1 elements, alkaline earth metals for Group 2 elements, transition metals for Group 3-12 elements, and halogens or halides for Group 17 elements.

The term "hydrocarbon" whenever used in this specification and claims refers to a compound containing only carbon and hydrogen, whether saturated or unsaturated. Other identifiers can be utilized to indicate the presence of particular groups in the hydrocarbon (e.g., halogenated hydrocarbon indicates the presence of one or more halogen atoms replacing an equivalent number of hydrogen atoms in the hydrocarbon). Non-limiting examples of hydrocarbons include alkanes (linear, branched, and cyclic), alkenes (olefins), and aromatics, among other compounds.

The term "aliphatic" is used herein to refer to a class of acyclic or cyclic, saturated or unsaturated, carbon compounds, excluding aromatic compounds, e.g., an aliphatic compound is a non-aromatic organic compound. An "aliphatic group" is a generalized group formed by removing one or more hydrogen atoms (as necessary for the particular group) from a carbon atom of an aliphatic compound. Aliphatic compounds and therefore aliphatic groups can contain organic functional group(s) and/or atom(s) other than carbon and hydrogen.

The term "aromatic" is used herein to describe a compound containing a cyclically conjugated hydrocarbon that follows the Hickel (4n+2) rule and containing (4n+2) pi-electrons, where n is an integer from 1 to about 5. Aromatic compounds may be monocyclic or polycyclic unless otherwise specified. Aromatic compounds include "arenes" (hydrocarbon aromatic compounds) and "heteroarenes," also termed "hetarenes" (heteroaromatic compounds formally derived from arenes by replacement of one or more methine (—C═) carbon atoms by trivalent or divalent heteroatoms, in such a way as to maintain the continuous pi-electron system characteristic of aromatic systems and a number of out-of-plane pi-electrons corresponding to the Hickel rule (4n+2)). Thus, an arene is an aromatic hydrocarbon, with or without side chains (e.g., benzene, toluene, or xylene, among others).

The term "olefin" is used herein to refer to acyclic and cyclic hydrocarbons having one or more carbon-carbon double bonds apart from the formal ones in aromatic compounds. The class "olefins" includes alkenes and cycloalkenes and the corresponding polyenes. Ethylene, propylene, 1-butene, 2-butene, 1-hexene and the like are non-limiting examples of olefins. The term "alpha olefin" as used in this specification and claims refers to an olefin that has a double bond between the first and second carbon atom of the longest contiguous chain of carbon atoms. The term "alpha olefin" includes linear and branched alpha olefins unless expressly stated otherwise.

The terms "alkane" and "paraffin" are used herein interchangeably to refer to a saturated hydrocarbon compound, and unless otherwise specified, an "alkane" and "paraffin" include linear (n-) and branched (iso-) alkanes (paraffins). Other identifiers can be utilized to indicate the presence of particular groups in the alkane (e.g., halogenated alkane indicates that the presence of one or more halogen atoms replacing an equivalent number of hydrogen atoms in the alkane). Therefore, unless otherwise stated, the term $C_{16-}$ paraffins includes linear $C_{16-}$ n-alkanes and branched $C_{16-}$ iso-alkanes, for example, the $C_{16-}$ paraffins can include $C_{12}$ to $C_{16}$ n-alkanes, $C_{12}$ to $C_{16}$ iso-alkanes, or mixtures thereof.

The carbon count terminology used herein is standard in the industry to reflect a range, an inclusive upper limit, or an inclusive lower limit of a hydrocarbon or mixture of hydrocarbons, and this terminology does not require that each and every carbon count encompassed by the range or limit is present in the composition, as will be understood by the person of ordinary skill. For example, "$C_{16-}$ paraffins" refers to $C_{16}$ and lower carbon number paraffins, but does not necessarily require that all compounds in the disclose range be present. Specifically, the skilled person will appreciate that this terminology is context dependent.

The terms "cycloalkane," "cycloparaffin," and "naphthene" are used herein interchangeably to describe a saturated cyclic hydrocarbon, with or without side chains, for example, cyclobutane. Other identifiers can be utilized to indicate the presence of particular groups in the cycloparaffin (e.g., halogenated cycloalkane indicates that the presence of one or more halogen atoms replacing an equivalent number of hydrogen atoms in the cycloalkane). Unsaturated cyclic hydrocarbons having one endocyclic double or one triple bond are called cycloalkenes and cycloalkynes, respectively. Those having more than one such multiple bond are cycloalkadienes, cycloalkatrienes, and so forth. Other identifiers can be utilized to indicate the presence of particular groups in the cycloalkenes, cycloalkadienes, cycloalkatrienes, and so forth.

Compound names such as the olefins in the $C_{16-}$ olefin stream or the paraffins in the $C_{16-}$ paraffins are named according to conventional organic chemistry nomenclature, and many of these compounds may have different systematic names. It will be readily appreciated by the person of ordinary skill in the art that different names may be used in the specification, claims, aspects, reaction schemes, or figures which refer to an identical compound that may be named differently elsewhere in the specification, claims, aspects, reaction schemes, or figures. For example, it will be apparent to the skilled person that the compound 5-methyl-8-methylenedodecane is the same compound as 5-methylene-8-methyl dodecane.

For any particular compound or group disclosed herein, any name or structure (general or specific) presented is intended to encompass all conformational isomers, regioisomers, stereoisomers, and mixtures thereof that can arise from a particular set of substituents, unless otherwise specified. The name or structure (general or specific) also encompasses all enantiomers, diastereomers, and other optical isomers (if there are any) whether in enantiomeric or racemic forms, as well as mixtures of stereoisomers, as would be recognized by a skilled artisan, unless otherwise specified. For instance, a general reference to pentane includes n-pentane, 2-methyl-butane, and 2,2-dimethylpropane; and a general reference to a butyl group includes a n-butyl group, a sec-butyl group, an iso-butyl group, and a t-butyl group.

Unless otherwise specified, the term "substituted" when used to describe a group, for example, when referring to a substituted analog of a particular group, is intended to describe any non-hydrogen moiety that formally replaces a hydrogen in that group, and is intended to be non-limiting. Also, unless otherwise specified, a group or groups can also be referred to herein as "unsubstituted" or by equivalent terms such as "non-substituted," which refers to the original group in which a non-hydrogen moiety does not replace a hydrogen within that group. Moreover, unless otherwise specified, "substituted" is intended to be non-limiting and include inorganic substituents or organic substituents as understood by one of ordinary skill in the art.

The terms "contacting" and "combining" are used herein to describe catalysts, compositions, processes, and methods in which the materials or components are contacted or combined together in any order, in any manner, and for any length of time, unless otherwise specified. For example, the materials or components can be blended, mixed, slurried, dissolved, reacted, treated, impregnated, compounded, or otherwise contacted or combined in some other manner or by any suitable method or technique.

In this disclosure, while processes and methods are described in terms of "comprising" various components or steps, the processes and methods also can "consist essentially of" or "consist of" the various components or steps, unless stated otherwise. The terms "a," "an," and "the" are intended to include plural alternatives, e.g., at least one, unless otherwise specified.

The terms "catalyst", "catalyst composition," "catalyst mixture," "catalyst system," and the like, do not depend upon the actual product or composition resulting from the contact or reaction of the initial components of the claimed catalyst or catalyst composition/mixture/system, the nature of the active catalytic site, or the fate of the co-catalyst, or substrate for the catalyst, or any activator (e.g., activator-support), after combining these components. Therefore, the terms "catalyst composition," "catalyst mixture," "catalyst system," and the like, encompass the initial starting components of the composition, as well as whatever product(s) may result from contacting these initial starting components, and this is inclusive of both heterogeneous and homogenous catalyst systems or compositions. The terms "catalyst composition," "catalyst mixture," "catalyst system," and the like, may be used interchangeably throughout this disclosure.

Several types of ranges are disclosed in the present invention. When a range of any type is disclosed or claimed, the intent is to disclose or claim individually each possible number that such a range could reasonably encompass, including end points of the range as well as any sub-ranges and combinations of sub-ranges encompassed therein. For example, the amount of $C_{10}$ monoolefins in the mixture of decenes can be in various ranges. By a disclosure that the mixture of decenes contains from 76 mol % to 95 mol % $C_{10}$ monoolefins, the intent is to recite that the molar amount can be any amount in the range and, for example, can include any range or combination of ranges from 76 mol % to 95 mol % $C_{10}$ monoolefins, such as from 78 mol % to 90 mol %, from 80 mol % to 88 mol %, or from 82 mol % to 86 mol %, and so forth. Likewise, all other ranges disclosed herein should be interpreted in a manner similar to this example.

In general, an amount, size, formulation, parameter, range, or other quantity or characteristic is "about" or "approximate" whether or not expressly stated to be such. Whether or not modified by the term "about" or "approximately," the claims include equivalents to the quantities or characteristics.

Although any methods, devices, and materials similar or equivalent to those described herein can be used in the practice or testing of the invention, the typical methods, devices, and materials are herein described.

All publications and patents mentioned herein are incorporated herein by reference in their entirety for the purpose of describing and disclosing, for example, the constructs and methodologies that are described in the publications and patents, which might be used in connection with the presently described invention.

DETAILED DESCRIPTION OF THE INVENTION

Instead of producing aviation fuels from a petroleum source, the processes for making aviation fuels disclosed herein generally include a step of reacting particular alpha-olefins with a mixture of decenes in the presence of an oligomerization catalyst or a metathesis catalyst, followed by hydrogenation. The resulting compositions have a high degree of branching and excellent low temperature properties, such as low viscosities at low temperatures and low pour point temperatures.

Processes for Making Aviation Fuels

A first process for making an aviation fuel in an aspect of this invention can comprise (or consist essentially of, or consist of) (a) contacting an ethylene feed with a first catalyst system comprising a first oligomerization catalyst to form an oligomerization product comprising at least one $C_4$-$C_8$ alpha-olefin and a mixture of decenes, (b) separating the mixture of decenes from the oligomerization product, (c) forming a $C_{16-}$ olefin stream by (i) contacting the mixture of decenes with at least one $C_{6-}$ alpha-olefin in the presence of a second catalyst system comprising a second oligomerization catalyst, or (ii) contacting the mixture of decenes with at least one $C_{8-}$ alpha-olefin in the presence of a second catalyst system comprising a metathesis catalyst, (d) optionally, hydrogenating the $C_{16-}$ olefin stream in the presence of a first hydrogenation catalyst to provide $C_{16-}$ paraffins, and (e) optionally, using the $C_{16-}$ paraffins as a component to form an aviation fuel.

A second process for making an aviation fuel in another aspect of this invention can comprise (or consist essentially of, or consist of) (a) contacting an ethylene feed with a first catalyst system comprising a first oligomerization catalyst to form an oligomerization product comprising at least one $C_4$-$C_8$ alpha-olefin and a mixture of decenes, (b) separating the mixture of decenes from the oligomerization product, (c) contacting the mixture of decenes with at least one $C_{6-}$ alpha-olefin in the presence of a second catalyst system comprising a second oligomerization catalyst to provide a $C_{16-}$ olefin stream, (d) optionally, hydrogenating the $C_{16-}$ olefin stream in the presence of a first hydrogenation catalyst to provide $C_{16-}$ paraffins, and (e) optionally, using the $C_{16-}$ paraffins as a component to form an aviation fuel.

A third process for making an aviation fuel in another aspect of this invention can comprise (or consist essentially of, or consist of) (a) contacting an ethylene feed with a first catalyst system comprising a first oligomerization catalyst to form an oligomerization product comprising at least one $C_4$-$C_8$ alpha-olefin and a mixture of decenes, (b) separating the mixture of decenes from the oligomerization product, (c) contacting the mixture of decenes with at least one $C_{8-}$ alpha-olefin in the presence of a second catalyst system comprising a metathesis catalyst to provide a $C_{16-}$ olefin stream, (d) optionally, hydrogenating the $C_{16-}$ olefin stream in the presence of a first hydrogenation catalyst to provide $C_{16-}$ paraffins, and (e) optionally, using the $C_{16-}$ paraffins as a component to form an aviation fuel.

A fourth process for making an aviation fuel in yet another aspect of this invention can comprise (or consist essentially of, or consist of) (a) contacting an ethylene feed with a first catalyst system comprising a first oligomerization catalyst to form an oligomerization product comprising at least one $C_4$-$C_8$ alpha-olefin and a mixture of decenes, (b) separating the mixture of decenes from the oligomerization product, (c) optionally, hydrogenating the mixture of decenes in the presence of a second hydrogenation catalyst to provide a mixture of decanes, and (d) optionally, using the mixture of decanes as a component to form an aviation fuel. In this fourth process for making an aviation fuel, the step of using the mixture of decanes as a component to form the aviation fuel can comprise blending the mixture of decanes with $C_{16-}$ paraffins and/or cycloparaffins to form the aviation fuel.

A fifth process for making an aviation fuel in still another aspect of this invention can comprise (or consist essentially of, or consist of) (a) contacting an ethylene feed with a first catalyst system comprising a first oligomerization catalyst to form an oligomerization product comprising at least one $C_4$-$C_6$ alpha-olefin or at least one $C_4$-$C_8$ alpha-olefin and a mixture of decenes, (b) contacting the oligomerization product with a second catalyst system comprising a second oligomerization catalyst or a metathesis catalyst to provide a $C_{16-}$ olefin stream, (c) optionally, hydrogenating the $C_{16-}$ olefin stream in the presence of a first hydrogenation catalyst to provide $C_{16-}$ paraffins, and (d) optionally, using the $C_{16-}$ paraffins as a component to form an aviation fuel. In this fifth process, the steps of contacting the ethylene feed with the first catalyst system and contacting the oligomerization product with the second catalyst system can be conducted in the same reactor, while in another aspect, the steps of contacting the ethylene feed with the first catalyst system and contacting the oligomerization product with the second catalyst system can be conducted in different reactors.

In these processes, the $C_{6-}$ alpha-olefin can comprise, consist essentially of, or be selected from, for example, ethylene, propylene, 1-butene, 1-pentene, 1-hexene, or a combination thereof; or alternatively, ethylene, 1-butene, 1-hexene, or a combination thereof. The $C_{8-}$ alpha-olefins in these processes can comprise, consist essentially of, or be selected from, for example, propylene, 1-butene, isobutylene, 1-pentene, 1-hexene, 3,3-dimethyl-1-butene, 1-octene, or a combination thereof; or alternatively, propylene, 1-butene, 1-hexene, 1-octene, or a combination thereof. Because the mixture of decenes can be contacted with at least one $C_{8-}$ alpha-olefin in the presence of a second catalyst system comprising a metathesis catalyst to provide a $C_{16-}$ olefin stream, it is not necessary to include ethylene among the $C_{8-}$ alpha-olefins, which would result in a non-productive olefin metathesis reaction. The $C_4$-$C_8$ alpha-olefin in this process, therefore, can comprise or be selected from, for example, 1-butene, 1-hexene, 1-octene, or any combination thereof, in one aspect, and in another aspect, the $C_4$-$C_6$ alpha-olefin can comprise or be selected from 1-butene, 1-hexene, or a combination thereof.

This disclosure also encompasses, in another aspect, a process for making a sustainable aviation fuel. In this aspect, at least a portion of the ethylene feed is a bio-ethylene feed, i.e., all or any portion of the ethylene feed can be a bio-ethylene feed. Thus, any of the processes for making an aviation fuel can further comprise providing the bio-ethylene feed by {1}converting a starch-based feedstock, a sugar-based feedstock, or a cellulosic feedstock to a biomass ethanol, and {2}dehydrating the biomass ethanol to provide a bio-ethylene feed. All or any portion of the bio-ethylene feed can be derived from the dehydration of biomass ethanol. Accordingly, the resulting aviation fuel can be a sustainable aviation fuel.

Therefore, in this aspect, the sustainable aviation fuel provided herein can be certified as compliant with the Carbon Offsetting and Reduction Scheme for International Aviation (CORSIA) sustainability criteria in accordance with the International Sustainability and Carbon Certification (ISCC) CORSIA certification system. Additionally or alternatively, the sustainable aviation fuel provided herein can be certified as a Lower Carbon Aviation Fuel (LCAF) in accordance with the International Sustainability and Carbon Certification (ISCC) LCAF certification system. In either, the certification can be based upon the weight or fraction of the sustainable aviation fuel attributable to the biomass ethanol determined by mass balance and the free attribution method.

If desired, the sustainable aviation fuel or a component thereof prepared as described herein can be used as-is, that is, it can be used without further purification. In another aspect, the sustainable aviation fuel or a component thereof prepared as described herein can be used following further purification by any method. Suitable purifications may be designed to remove contaminants such as sulfur compounds or may be used to fractionate the sustainable aviation fuel or component thereof to select a higher or lower boiling fraction thereof. In a further aspect, the sustainable aviation fuel or the component thereof can be blended—for instance, at 10 to 50 wt. %—with a non-sustainable aviation fuel (e.g., fossil fuel based).

First and Second Catalyst Systems

The ethylene feed is contacted with the first catalyst system comprising a first oligomerization catalyst to form an oligomerization product comprising at least one $C_4$-$C_8$ alpha-olefin and a mixture of decenes. In the first process, the second process, and the third process, this mixture of decenes can be further oligomerized with, for example, at least one $C_{6-}$ alpha-olefin or $C_{8-}$ alpha-olefin in the presence of a second catalyst system comprising a second oligomerization catalyst or a metathesis catalyst to form a $C_{16-}$ olefin stream. In the fifth process, the oligomerization product can be further oligomerized in the presence of a second catalyst system comprising a second oligomerization catalyst or a metathesis catalyst to form a $C_{16-}$ olefin stream. The first catalyst system and the second catalyst system can comprise, independently, any suitable oligomerization catalyst. Alternatively, the first catalyst system can comprise any suitable oligomerization catalyst and the second catalyst system can comprise any suitable metathesis catalyst.

For instance, the first oligomerization catalyst can comprise, consist essentially of, consist of, or can be selected from any oligomerization catalyst. The second oligomerization catalyst can comprise, consist essentially of, consist of, or be selected from any oligomerization catalyst promoting anti-Markovnikov selectivity. The metathesis catalyst can comprise, consist essentially of, consist of, or be selected from any metathesis catalyst.

While not limited thereto, the first catalyst system, the second catalyst system, or both catalyst systems independently can comprise a chromium-based catalyst, a metallocene-based catalyst, a Ziegler-Natta based catalyst, a metal-oxide supported Group 6-10 transition metal-based catalyst, or a combination thereof. For example, aspects of this disclosure are provided in one or more of U.S. Pat. Nos. 6,291,733; 8,334,420; 8,680,003; 8,791,217; 9,115,225; 9,175,109; 9,352,309; 9,708,549; 9,745,230; 9,968,921; 10,183,899; 10,240,102; 10,329,212; 10,414,698; 10,435,334; 10,435,336; 10,544,070; 10,927,052; 11,072,569; and 11,358,914. These references describe chromium-based catalysts and other catalysts which are useful for the ethylene oligomerization process described herein and can be employed as the first catalyst system or the second catalyst system.

In another aspect, the first catalyst system, the second catalyst system, or both catalyst systems independently can comprise, can consist essentially, or can be tungstated zirconium, molybdenum zirconium, nickel and/or cobalt doped tungstated zirconium, a nickel and/or cobalt doped molybdenum zirconium catalyst, a Group 3 to Group 12 metal-treated zeolite, or combinations thereof.

In another aspect, the first catalyst system, the second catalyst system, or both catalyst systems independently can comprise, consist essentially of, or be selected from molybdenum oxide on alumina ($MoO_3/Al_2O_3$), tungsten oxide on silica ($WO_3/SiO_2$), tungsten oxide on silica-alumina ($WO_3/SiO_2/Al_2O_3$), rhenium oxide on alumina ($Re_2O_7/Al_2O_3$), cobalt oxide and molybdenum oxide on alumina ($CoO/MoO_3/Al_2O_3$), rhenium oxide on alumina activated with tetramethyl tin ($Re_2O_7/Al_2O_3/SnMe_4$), or any combination thereof.

In these and other processes for making an aviation fuel, the second oligomerization catalyst can comprise, consist essentially of, consist of, or be selected from (a) $BF_3$ and a protic promoter or (b) a chemically-modified solid oxide which comprises a solid oxide treated with an electron-withdrawing anion.

The second oligomerization catalyst can comprise, consist essentially of, consist of, or be selected from $BF_3$ and a protic promoter in an aspect, and this aspect, the protic promoter can comprise, consist essentially of, or be selected from water, an alcohol, a carboxylic acid, or any combination thereof.

Suitable alcohols include a $C_1$ to $C_{20}$, alcohol; alternatively, a $C_1$ to $C_{15}$, alcohol; alternatively, a $C_1$ to $C_{10}$ alcohol; or alternatively, a $C_1$ to $C_6$ alcohol; a monool, a polyol, or any combination thereof; a monool, a diol, or any combination thereof; alternatively, a monool; alternatively, a polyol; or alternatively, a diol; a linear alcohol, a branched alcohol, or any combination thereof; alternatively, a linear alcohol; or alternatively, a branched alcohol; methanol, ethanol, a propanol, a butanol, a pentanol, a hexanol, or any combination thereof; alternatively, methanol; alternatively, ethanol; alternatively, 1-propanol; alternatively, 2-propanol; alternatively, 1-butanol; alternatively, 1-pentanol; or alternatively, 1-hexanol; or any combination thereof.

Suitable carboxylic acids include a $C_2$ to $C_{20}$ carboxylic acid; alternatively, a $C_2$ to $C_{15}$ carboxylic acid; alternatively, a $C_3$ to $C_{10}$ carboxylic acid; or alternatively, a $C_3$ to $C_8$ carboxylic acid; a mono-carboxylic acid, a poly-carboxylic acid, or any combination thereof; alternatively, a monocarboxylic acid, a di-carboxylic acid, or any combination thereof; alternatively, a mono-carboxylic acid; alternatively, a poly-carboxylic acid; or alternatively, a di-carboxylic acid; a linear carboxylic acid, a branched carboxylic acid, or any combination thereof; alternatively, a linear carboxylic acid; or alternatively a branched carboxylic acid; acetic acid, propionic acid, a butyric acid, a hexanoic acid, a heptanoic acid, an octanoic acid, a nonanoic acid, a decanoic acid, a succinic acid, or any combination thereof; or any combination thereof.

The second oligomerization catalyst can comprise, consist essentially of, consist of, or be selected from a chemically-modified solid oxide which comprises a solid oxide treated with an electron-withdrawing anion, and the chemically-modified solid oxide can be generated by treatment of a solid oxide with an acid of an electron-withdrawing anion or a salt of an electron-withdrawing anion. While not required, following treatment of the solid oxide with the acid or the salt of an electron-withdrawing anion, the chemically-modified solid oxide often is dried, or calcined, or both dried and calcined.

The solid oxide component of the chemically-modified solid oxide can comprise, consist essentially of, or be $Al_2O_3$, $B_2O_3$, BeO, $Bi_2O_3$, CdO, $Co_3O_4$, $Cr_2O_3$, CuO, $Fe_2O_3$, $Ga_2O_3$, $La_2O_3$, $Mn_2O_3$, $MoO_3$, $Na_2O$, NiO, $P_2O_5$, $Sb_2O_5$, $SiO_2$, $SnO_2$, SrO, $ThO_2$, $TiO_2$, $V_2O_5$, $WO_3$, $Y_2O_3$, ZnO, $ZrO_2$, $K_2O$, CaO, $La_2O_3$, $Ce_2O_3$, mixtures thereof, mixed oxides thereof (for example, silica-alumina), as well as any combination thereof. For instance, the solid oxide of the chemically-modified solid oxide can comprise, consist essentially of, or be silica, alumina, titania, zirconia, magnesia, boria, calcia, zinc oxide, silica-alumina, silica-coated alumina, silica-titania, silica-zirconia, silica-magnesia, alumina-titania, alumina-zirconia, zinc-aluminate, alumina-boria, silica-boria, aluminum phosphate, aluminophosphate, aluminophosphate-silica, magnesium aluminate, titania-zirconia, or any combination thereof.

The electron-withdrawing anion of the chemically-modified solid oxide can comprise, consist essentially of, or be sulfate, bisulfate, fluorosulfate, phosphate, fluorophosphate, triflate, mesylate, tosylate, thiosulfate, a $C_1$-$C_{10}$ alkyl sulfonate, a $C_6$-$C_{14}$ aryl sulfonate, fluoride, chloride, or any combination thereof. For instance, the chemically-modified solid oxide can be generated by treatment of a solid oxide with sulfuric acid, sulfate ion, bisulfate ion, fluorosulfuric acid, fluorosulfate ion, phosphoric acid, phosphate ion, fluorophosphoric acid, monofluorophosphate ion, triflic (trifluoromethanesulfonic) acid, triflate trifluoromethanesulfonate) ion, methanesulfonic acid, mesylate (methanesulfonate) ion, toluenesulfonic acid, tosylate (toluenesulfonate) ion, thiosulfate ion, a $C_1$-$C_{10}$ alkyl sulfonic acid, a $C_1$-$C_{10}$ alkyl sulfonate ion, a $C_6$-$C_{14}$ aryl sulfonic acid, a $C_6$-$C_{14}$ aryl sulfonate ion, fluoride ion, chloride ion, or any combination thereof.

In one aspect, the chemically-modified solid oxide can comprise a sulfur oxoacid anion-modified solid oxide, a phosphorus oxoacid anion-modified solid oxide, or a halide ion-modified solid oxide. In another aspect, the chemically-modified solid oxide can comprise a sulfated solid oxide, bisulfated (hydrogen sulfated) solid oxide, fluorosulfated solid oxide, phosphated solid oxide, fluorophosphated solid oxide, fluorided solid oxide, or chlorided solid oxide. In yet another aspect, the solid oxide of the chemically-modified solid oxide comprises, consists essentially of, or is silica, alumina, silica-alumina, silica-coated alumina, aluminum phosphate, aluminophosphate, heteropolytungstate, titania, zirconia, magnesia, boria, zinc oxide, a mixed oxide thereof, or any mixture thereof; and the electron-withdrawing anion of the chemically-modified solid oxide comprises, consists essentially of, or is sulfate, bisulfate, fluorosulfate, phosphate, fluorophosphates, fluoride, or chloride. In still another aspect, the chemically-modified solid oxide comprises or consists essentially of sulfated alumina, sulfated silica-alumina, or sulfated silica-coated alumina. Optionally, the chemically-modified solid oxide can be metal-treated with a metal cation selected from a Group 1, 2, 12, or 13 metal.

Referring again to the first catalyst system, the second catalyst system, or both catalyst systems, the first catalyst system (or the second catalyst system, or both) independently can comprise a metal alkyl compound selected from an organoaluminum compound, an organoaluminoxane, an organoboron compound, an organozinc compound, an organomagnesium compound, an organolithium compound, or any combination thereof. As an example, the first catalyst system, the second catalyst system, or both catalyst systems independently can comprise a metal alkyl compound having the general formula (a) $M^3(X^{10})_n(X^{11})_{3-n}$, wherein $M^3$ is boron or aluminum and n is from 1 to 3 inclusive; (b) $M^4(X^{10})_n(X^{11})_{2-n}$, wherein $M^4$ is magnesium or zinc and n is from 1 to 2 inclusive; or (c) $M^5X^{10}$; wherein $M^5$ is Li; wherein $X^{10}$ is independently hydride or a $C_1$ to $C_{20}$ hydrocarbyl; and $X^{11}$ is independently a halide, a hydride, a $C_1$ to $C_{20}$ hydrocarbyl, or a $C_1$ to $C_{20}$ hydrocarbyloxide.

In the processes for making an aviation fuel, in an aspect, the first catalyst system, the second catalyst system, or both catalyst systems independently can further comprise hydrogen. In another aspect, the first catalyst system, the second catalyst system, or both catalyst systems independently can further comprise hydrogen, for example, at a partial pressure of from 2 psi to 100 psi; from 5 psi to 75 psi; or from 10 psi to 50 psi.

Oligomerization Products

In the processes for making an aviation fuel according to this disclosure, the first catalyst system comprising a first oligomerization catalyst can oligomerize the ethylene feed to form an oligomerization product comprising at least one $C_4$-$C_8$ alpha-olefin and a mixture of decenes. The $C_4$-$C_8$ alpha-olefin in this process can comprise or be selected from, for example, 1-butene, 1-hexene, 1-octene, or any combination thereof. The oligomerization product can further comprise octenes, dodecenes, tetradecenes, or any combination thereof.

The first oligomerization catalyst and the second oligomerization catalyst can be selected independently from any olefin oligomerization catalyst, and the metathesis catalyst can be selected from any metathesis catalyst. In an aspect, an oligomerization catalyst such as a chromium-based catalyst can be utilized as the first oligomerization catalyst and can produce the oligomerization product comprising at least one $C_4$-$C_8$ alpha-olefin and a mixture of decenes described in detail in this disclosure. The second catalyst system comprising a second oligomerization catalyst can be used to further oligomerize the mixed decenes with a $C_{6-}$ alpha-olefin to form a $C_{16-}$ olefin stream. The $C_{16-}$ olefin stream can be hydrogenated and used as a component of an aviation fuel.

The second catalyst system comprising a metathesis catalyst can be used in a metathesis reaction of the mixed decenes with a $C_{8-}$ alpha-olefin to form a $C_{16-}$ olefin stream, which also can be hydrogenated and used as a component of an aviation fuel.

The second oligomerization catalyst can also be used to for contacting an oligomerization product comprising at least one $C_4$-$C_6$ alpha-olefin and a mixture of decenes, in which the mixture of decenes has not be separated from the oligomerization product, in order to provide a $C_{16-}$ olefin stream. In an aspect, the first catalyst system, the second catalyst system, or both independently can comprise a chromium-based catalyst, a metallocene-based catalyst, a Ziegler-Natta based catalyst, a metal-oxide supported Group 6-10 transition metal-based catalyst, or a combination thereof.

In one aspect, even though the oligomerization product which is formed from oligomerizing the ethylene feed can include a mixture of olefins, it can be analyzed and the composition can be well-defined. The composition of the oligomerization product prepared from ethylene using the first catalyst system can be adjusted according to the specific catalyst system employed and the conditions under which the oligomerization is carried out. In an aspect, the oligomerization product can comprise at least 60 mol %; at least 65 mol %; at least 70 mol %; at least 75 mol %; at least 80 mol %; at least 85 mol %; at least 90 mol %; or at least 95 mol % 1-hexene. Alternatively and in a further aspect, the oligomerization product can comprise at least 60 mol %; at least 65 mol %; at least 70 mol %; at least 75 mol %; at least 80 mol %; at least 85 mol %; at least 90 mol %; or at least 95 mol % 1-octene. The oligomerization product can also comprise at least 60 mol %; at least 65 mol %; at least 70 mol %; at least 75 mol %; at least 80 mol %; at least 85 mol %; at least 90 mol %; or at least 95 mol % 1-hexene and 1-octene combined.

A further aspect provides that the oligomerization product prepared from ethylene (at least a portion of which can be a bio-ethylene) using the first catalyst system can comprise at least 70 wt. % hexene; at least 75 wt. % hexene; at least 80 wt. % hexene; at least 85 wt. % hexene; or at least 90 wt. % hexene, based upon the weight of the oligomerization product. Alternatively and in a further aspect, the oligomerization product can include from 70 wt. % to 99.8 wt. % hexene; from 75 wt. % to 99.7 wt. % hexene; or alternatively, from 80 wt. % to 99.6 wt. % hexane, based upon the weight of the oligomerization product. Alternatively and in another aspect, the oligomerization product can also comprise at least 70 wt. % octene; at least 75 wt. % octene; at least 80 wt. % octene; at least 85 wt. % octene; or at least 90 wt. % octene, based upon the weight of the oligomerization product. Alternatively, the oligomerization product can include from 70 wt. % to 99.8 wt. % octene; from 75 wt. % to 99.7 wt. % octene; or from 80 wt. % to 99.6 wt. % octene, based upon the weight of the oligomerization product.

In a further aspect, the oligomerization product can include the mixture of decenes in a concentration of at least 0.5 mol %; at least 1 mol %; at least 2 mol %; at least 3 mol %; at least 4 mol %; at least 5 mol %; at least 6 mol %; at least 8 mol %; at least 10 mol %; at least 12 mol %; or at least 15 mol % in the oligomerization product. The oligomerization product can comprise the mixture of decenes in a concentration of less than 40 mol %; less than 35 mol %; less than 30 mol %; less than 25 mol %; less than 20 mol %; less than 15 mol %; less than 10 mol %; or less than 5 mol %. For example, contacting the ethylene feed with the first catalyst system can be carried out under conditions in which at least 0.2 wt. %, at least 1 wt. %, at least 2 wt. %, at least 5 wt. %, at least 7 wt. %, at least 10 wt. %, at least 12 wt. %, or at least 15 wt. % of the oligomerization product can include the mixture of decenes. Contacting the ethylene feed (e.g., a bio-ethylene feed) with the first catalyst system also may be carried out under conditions in which less than 5 wt. %, less than 7 wt. %, less than 10 wt. %, less than 12 wt. %, less than 15 wt. %, less than 18 wt. %, or less than 20 wt. % of the oligomerization product can comprise or can consist essentially of the mixture of decenes.

As described herein, the mixture of decenes, although it can be well-defined, is formed in a non-selective manner such that a number of decene isomers are produced. For example, the mixture of decenes can comprise 2-butyl-1-hexene, 3-propyl-1-heptene, 4-ethyl-1-octene, 5-methyl-1-nonene, 4-decene, and 5-decene in one aspect, while in another aspect, the mixture of decenes can comprise 2-butyl-1-hexene, 3-propyl-1-heptene, 4-ethyl-1-octene, and 5-methyl-1-nonene. In yet another aspect, the mixture of decenes is described in U.S. Pat. No. 10,647,626.

In an aspect, the mixture of decenes can comprise at least 76 mol %, at least 78 mol %, at least 80 mol %, or at least 82 mol % $C_{10}$ monoolefins. For example, the mixture of decenes can comprise from 76 mol % to 95 mol % $C_{10}$ monoolefins; from 78 mol % to 90 mol % $C_{10}$ monoolefins; from 80 mol % to 88 mol % $C_{10}$ monoolefins; or from 82 mol % to 86 mol % $C_{10}$ monoolefins.

According to a further aspect, the $C_{10}$ monoolefins can include (a) at least 3 mol %, at least 4 mol %, at least 5 mol %, at least 6 mol %, at least 7 mol %, or at least 8 mol % 2-butyl-1-hexene; (b) at least 8 mol %, at least 9 mol %, at least 10 mol %, at least 11 mol %, at least 12 mol %, or at least 13 mol % 3-propyl-1-heptene; (c) at least 6 mol %, at least 7 mol %, at least 8 mol %, at least 9 mol %, at least 10 mol %, or at least 11 mol % 4-ethyl-1-octene; and (d) at least 20 mol %, at least 22 mol %, at least 24 mol %, at least 26 mol %, at least 28 mol %, or at least 30 mol % 5-methyl-1-nonene.

Further aspects of the mixture of decenes, and $C_{10}$ monoolefins specifically, include the following. In one aspect, the $C_{10}$ monoolefins can comprise from 3 mol % to 20 mol %, from 4 mol % to 18 mol %, from 5 mol % to 17 mol %, from 6 mol % to 16 mol %, or from 7 mol % to 15 mol % 2-butyl-1-hexene. Another aspect of the $C_{10}$ monoolefins is that they can comprise from 10 mol % to 32 mol %, from 11 mol % to 30 mol %, from 12 mol % to 28 mol %, from 13 mol % to 26 mol %, or from 14 mol % to 24 mol % 3-propyl-1-heptene. In a further aspect, the $C_{10}$ monoolefins comprise from 7 mol % to 25 mol %, from 8 mol % to 24 mol %, from 9 mol % to 23 mol %, from 10 mol % to 22 mol %, or from 11 mol % to 21 mol % 4-ethyl-1-octene. In still a further aspect, the $C_{10}$ monoolefins comprise from 24 mol % to 52 mol %, from 26 mol % to 50 mol %, from 28 mol % to 48 mol %, from 30 mol % to 46 mol %, or from 32 mol % to 44 mol % 5-methyl-1-nonene.

According to another aspect, the $C_{10}$ monoolefins have any of the following features: (a) a molar ratio of 2-butyl-1-hexene to 5-methyl-1-nonene of at least 2:1, at least 2.4:1, at least 2.6:1, or at least 2.8:1; (b) a molar ratio of 3-propyl-1-heptene to 5-methyl-1-nonene of at least 1.2:1, at least 1.4:1, at least 1.6:1, or at least 1.8:1; (c) a molar ratio of 4-ethyl-1-octene to 5-methyl-1-nonene of at least 1.6:1, at least 1.7:1, at least 1.9:1, or at least 2.1:1; or (d) any combination thereof.

The oligomerization product can further comprise $C_{9-}$ monoolefins, $C_{11+}$ monoolefins, or combinations thereof, in addition to the decene mixture and the at least one $C_4$-$C_8$ alpha-olefin. In an aspect, the oligomerization product can be characterized as further comprising at least 1 mol %, at least 2 mol %, at least 3 mol %, or at least 4 mol % $C_{14}$ monoolefins. For example, the oligomerization product can further comprise from 1 mol % to 12 mol % $C_{14}$ monoolefins; from 2 mol % to 10 mol % $C_{14}$ monoolefins; from 3 mol % to 8 mol % $C_{14}$ monoolefins; or from 4 mol % to 7 mol % $C_{14}$ monoolefins. A further aspect provides that the oligomerization product can further comprise (a) from 0.1 mol % to 5 mol %, from 0.25 mol % to 4 mol %, or from 0.5 mol % to 3 mol % $C_8$ monoolefins, wherein the $C_8$ monoolefins comprise at least 95 mol % 1-octene; (b) from 0.1 mol % to 5 mol %, from 0.25 mol % to 4 mol %, or from 0.5 mol % to 3 mol % $C_{12}$ monoolefins, wherein the $C_{12}$ monoolefins comprise from 54 mol % to 74 mol % 1-dodecene; (c) from 0.05 mol % to 2 mol %, from 0.04 mol % to 1.5 mol %, from 0.06 mol % to 1.25 mol %, from 0.08 mol % to 1 mol %, or from 0.1 mol % to 0.75 mol % $C_{16}$ monoolefins and/or $C_{18}$ monoolefins; or (d) any combination thereof.

The mixture of decenes produced according to this disclosure, in an aspect, can comprise at least 95 mol % $C_{10}$ monoolefins, and the $C_{10}$ monoolefins comprise (a) at least 3 mol % 2-butyl-1-hexene; (b) at least 10 mol % 3-propyl-1-heptene; (c) at least 7 mol % 4-ethyl-1-octene; and (d) at least 24 mol % 5-methyl-1-nonene. The mixture of decenes can also include linear $C_{10}$ monoolefins comprising or consisting essentially of 1-decene, 4-decene, 5-decene, or combinations thereof.

Chromium-Based Catalyst Systems

In an aspect, the first catalyst system, the second catalyst system, or both catalyst systems, independently can comprise or consist essentially of a chromium-based catalyst. For example, the chromium-based catalyst can produce the oligomerization product comprising at least one $C_4$-$C_8$ alpha-olefin and a mixture of decenes described in detail in this disclosure. This mixture of decenes can be further oligomerized with, for example, at least one $C_{6-}$ alpha-olefin in the presence of a second catalyst system, which can also comprise a chromium-based catalyst, but other catalyst systems can be used, to provide a $C_{16-}$ olefin stream. The chromium-based catalyst system uses a combination of catalyst components that include a chromium compound and certain heteroatomic compounds referred to as "heteroatomic ligands" which can constitute a ligand on the chromium compound itself or can be used as a separate component of the chromium-based catalyst system in combination with a chromium compound that does not include the heteroatomic ligand.

The chromium-based catalyst can comprise or can consist essentially of (a) a chromium-containing compound, (b) a heteroatomic ligand, (c) a metal alkyl compound, and (d) optionally, a diluent. Again, the heteroatomic ligand can be a separate component of the first catalyst system, the second catalyst system, or both, or it can be a ligand complexed to the chromium-containing compound of the first catalyst system, the second catalyst system, or both. As an example, the heteroatomic ligand can comprise, consist essentially of, or be selected from a pyrrole compound, a diphosphino aminyl compound, an $N^2$-phosphinyl amidine compound, or an $N^2$-phosphinyl formamidine compound.

In an aspect of this disclosure the first catalyst system, the second catalyst system, or both independently can comprise, consist essentially of, or are selected from (a) a chromium-containing compound, a pyrrole compound, an organoaluminum compound, and optionally a halide containing compound; (b) a chromium-containing compound, a diphosphino aminyl compound, and an organoaluminum compound; (c) a chromium-containing compound complexed to a diphosphino aminyl compound, and an organoaluminum compound; (d) a chromium-containing compound, an $N^2$-phosphinyl amidine compound, and an organoaluminum compound; (e) a chromium-containing compound complexed to an $N^2$-phosphinyl amidine compound, and an organoaluminum compound; (f) a chromium-containing compound, an $N^2$-phosphinyl formamidine compound, and an organoaluminum compound; (g) a chromium-containing compound complexed to an $N^2$-phosphinyl formamidine compound, and an organoaluminum compound; or (h) any combinations thereof.

According to an aspect, the chromium-containing compound can comprise, consist essentially of, or be selected from chromium(II) nitrate, chromium(II) sulfate, chromium (II) fluoride, chromium(II) chloride, chromium(II) bromide, chromium(II) iodide, chromium(III) nitrate, chromium(III) sulfate, chromium(III) fluoride, chromium(III) chloride, chromium(III) bromide, or chromium(III) iodide.

In another aspect, the chromium-containing compound can be selected from a chromium(II) carboxylate, a chromium(II) alkoxide, chromium(II) aryloxide, a chromium(II) beta-dionate (i.e. beta-diketonate), a chromium(III) carboxylate, a chromium(III) alkoxide, chromium(III) aryloxide, or a chromium(III) beta-dionate (i.e. beta-diketonate). In one example, each carboxylate group of the chromium-containing compound independently can be a $C_2$ to $C_{24}$ carboxylate group, or alternatively, a $C_4$ to $C_{19}$ carboxylate group, or alternatively, a $C_5$ to $C_{12}$ carboxylate group. In another example, each alkoxide group of the chromium-containing compound independently can be a $C_1$ to $C_{24}$ alkoxy group, alternatively, a $C_4$ to $C_{19}$ alkoxy group, or alternatively, a $C_5$ to $C_{12}$ alkoxy group. In other examples, each aryloxide group of the chromium-containing compound independently can be a $C_6$ to $C_{24}$ aryloxy group, alternatively, a $C_6$ to $C_{19}$ aryloxy group, or alternatively, a $C_6$ to $C_{12}$ aryloxy group. Each beta-dionate group of the chromium-containing compound independently can be a $C_5$ to $C_{24}$ beta-dionate group, alternatively, a $C_5$ to $C_{19}$ beta-dionate group, or alternatively, a $C_5$ to $C_{12}$ beta-dionate group.

According to an aspect, the first catalyst system, the second catalyst system, or both independently can comprise a chromium carboxylate comprising or consisting essentially of an acetate, a propionate, a butyrate, a pentanoate, a hexanoate, a heptanoate, an octanoate, a nonanoate, a decanoate, an undecanoate, a dodecanoate, a tridecanoate, a tetradecanoate, a pentadecanoate, a hexadecanoate, a heptadecanoate, or an octadecanoate. The first catalyst system, the second catalyst system, or both independently also may comprise a chromium carboxylate wherein each carboxylate group of the chromium carboxylate is independently selected from acetate, propionate, n-butyrate, isobutyrate, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, laurate (n-dodecanoate), or stearate (n-octadecanoate).

Chromium carboxylates are useful chromium compounds, for example, the first catalyst system, the second catalyst system, or both independently can comprise a chromium carboxylate comprising, consisting essentially of, or selected from chromium(II) acetate, chromium(II) propionate, chromium(II) butyrate, chromium(II) isobutyrate, chromium(II) neopentanoate, chromium(II) oxalate, chromium(II) octanoate, chromium(II) 2-ethylhexanoate, chromium(II) laurate, chromium(II) stearate, chromium(III) acetate, chromium(III) propionate, chromium(III) butyrate, chromium(III) isobutyrate, chromium(III) neopentanoate, chromium(III) oxalate, chromium(III) octanoate, chromium (III) 2-ethylhexanoate, chromium(III) 2,2,6,6,-tetramethylheptanedionate, chromium(III) naphthenate, chromium(III) laurate, or chromium(III) stearate.

The heteroatomic ligands for the chromium-based catalyst system described herein can be used as a separate component of the chromium-based catalyst in combination with a chromium compound, or the heteroatomic ligands can constitute a ligand on the chromium compound itself. In an aspect, the heteroatomic ligand can comprise, can consist essentially of, or can be, an amine compound, an amide compound, an imide compound, or combinations thereof. For example, the heteroatomic ligand can comprise, can consist essentially of, or can be (a) a $C_2$ to $C_{30}$ amine; alternatively, a $C_2$ to $C_{20}$ amine; alternatively, $C_2$ to $C_{15}$ amine; or alternatively, a $C_2$ to $C_{10}$ amine; (b) a $C_3$ to $C_{30}$ amide; alternatively, a $C_3$ to $C_{20}$ amide; alternatively, $C_3$ to $C_{15}$ amide; or alternatively, a $C_3$ to $C_{10}$ amide; or (c) a $C_4$ to $C_{30}$ imide; alternatively, a $C_4$ to $C_{20}$ imide; alternatively, $C_4$ to $C_{15}$ imide; or alternatively, a $C_4$ to $C_{10}$ imide.

In a further aspect, the heteroatomic ligand can comprise, can consist essentially of, or can be, a pyrrole compound, a diphosphino aminyl compound, an $N^2$-phosphinyl amidine compound, an $N^2$-phosphinyl formamidine compound, or combinations thereof. For example, the heteroatomic ligand can comprise, can consist essentially of, or can be (a) any pyrrole compound that can form a chromium pyrrolide complex; (b) pyrrole ($C_5H_5N$), a derivative of pyrrole (e.g., indole), a substituted pyrroles, or a metal pyrrolide compound; or (c) pyrrole or any heteroleptic or homoleptic metal complex or salt containing a pyrrolide radical or ligand; or (d) a $C_4$ to $C_{30}$ pyrrole; alternatively, a $C_4$ to $C_{20}$ pyrrole; alternatively, $C_4$ to $C_{15}$ pyrrole; or alternatively, a $C_4$ to $C_{10}$ pyrrole.

In another aspect, the heteroatomic ligand can comprise, can consist essentially of, or can be a pyrrole compound having the Formula P1 or Formula I1:

P1

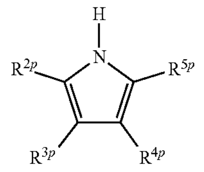

I1

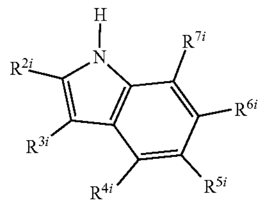

wherein $R^{2p}$, $R^{3p}$, $R^{4p}$, and $R^{5p}$ of Formula P1 and $R^{2i}$, $R^{3i}$, $R^{4i}$, $R^{5i}$, $R^{6i}$, and $R^{7i}$ of Formula I1 can each independently be hydrogen, a $C_1$ to $C_{18}$ organyl group, a $C_1$ to $C_{18}$ hydrocarbyl group, or a $C_3$ to $C_{60}$ silyl group; alternatively, hydrogen, a $C_1$ to $C_{15}$ organyl group, a $C_1$ to $C_{15}$ hydrocarbyl group, or a $C_3$ to $C_{45}$ silyl group; alternatively, hydrogen, a $C_1$ to $C_{10}$ organyl group, a $C_1$ to $C_{10}$ hydrocarbyl group, or a $C_3$ to $C_{30}$ silyl group; alternatively, hydrogen, a $C_1$ to $C_5$ organyl group, a $C_1$ to $C_5$ hydrocarbyl group, or a $C_3$ to $C_{15}$ silyl group.

For example, $R^{2p}$, $R^{3p}$, $R^{4p}$, and $R^{5p}$ of Formula P1 and $R^{2i}$, $R^{3i}$, $R^{4i}$, $R^{5i}$, $R^{6i}$, and $R^{7i}$ of Formula I1 can each independently be hydrogen or a $C_1$ to $C_{18}$ hydrocarbyl group; alternatively, hydrogen or a $C_1$ to $C_{15}$ hydrocarbyl group; alternatively, hydrogen or a $C_1$ to $C_{10}$ hydrocarbyl group; or alternatively, hydrogen or a $C_1$ to $C_5$ hydrocarbyl group.

In another aspect, the pyrrole compound can comprise, can consist essentially of, or can be, pyrrole, 2,5-dimethylpyrrole, 2-methyl-5-ethylpyrrole, 2-methyl-5-propylpyrrole, 2,5-diethylpyrrole, 3,4-dimethylpyrrole, 2,5-di-n-propylpyrrole, 2,5-di-n-butylpyrrole, 2,5-di-n-pentylpyrrole, 2,5-di-n-hexylpyrrole, 2,5-di-n-heptylpyrrole, 2,5-di-n-octylpyrrole, 2,5-dibenzylpyrrole, 2,4-dimethyl-3-ethylpyrrole, 2,3,5-triethylpyrrrole, 2,3,5-tri-n-butylpyrrrole, 2,3,5-tri-n-pentylpyrrrole, 2,3,5-tri-n-hexylpyrrrole, 2,3,5-tri-n-heptylpyrrrole, 2,3,5-tri-n-octylpyrrrole, 2,3,4,5-tetraethylpyrrole, 2,3,4,5-tetra-n-butylpyrrole, 2,3,4,5-tetra-n-hexylpyrrole, 2,5-bis(2',2',2'-trifluoroethyl)pyrrole, 2,5-bis(2'-methoxymethyl)pyrrole, 2-methyl-4-isopropylpyrrole, 2-ethyl-4-isopropylpyrrole, 2-methyl-4-sec-butylpyrrole, 2-ethyl-4-sec-butylpyrrole, 2-methyl-4-isobutylpyrrole, 2-ethyl-4-isobutylpyrrole, 2-methyl-4-t-butylpyrrole, 2-ethyl-4-t-butylpyrrole, 2-methyl-4-neopentylpyrrole, 2-ethyl-4-neopentylpyrrole, 3,4-diisopropylpyrrole, 3,4-di-sec-butylpyrrole, 3,4-diisobutylpyrrole, 3,4-di-t-butylpyrrole, 3,4-di-neopentylpropylpyrrole, tetrahydroindole, dipyrrolylmethane, indole, 3,4-dichloropyrrole, 2,3,4,5-tetrachloropyrrole, pyrrole-2-carboxylic acid, 2-acetylpyrrole, pyrrole-2-carboxaldehyde, 3-acetyl-2,4-dimethylpyrrole, ethyl-2,4-dimethyl-5-(ethoxycarbonyl)-3-pyrrole-propionate, or ethyl-3,5-dimethyl-2-pyrrolecarboxylate.

According to another aspect of the heteroatomic ligand, the pyrrole compound can comprise, can consist essentially of, or can be (a) a metal pyrrolide, such as an alkyl metal pyrrolide; (b) a diorganoaluminum pyrrolide of any pyrrole provided herein; (c) diethylaluminum 2,5-dimethylpyrrolide, ethylaluminum di(2,5-dimethylpyrrolide), aluminum tri(2,5-dimethylpyrrolide), or combinations thereof.

The heteroatomic ligand also may comprise, can consist essentially of, or can be, a diphosphino aminyl compound (i.e. a compound comprising a P—N—P (phosphorus-nitrogen-phosphorus) linkage). For example, the heteroatomic ligand can comprise, can consist essentially of, or can be a diphosphino aminyl moiety having Structure PNP2:

PNP2

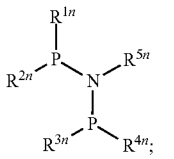

wherein $R^{1n}$, $R^{2n}$, $R^{3n}$, $R^{4n}$, and/or $R^{5n}$ independently can be (a) a $C_1$ to $C_{30}$ organyl group; alternatively, a $C_1$ to $C_{20}$ organyl group; alternatively, a $C_1$ to $C_{15}$ organyl group; alternatively, a $C_1$ to $C_{10}$ organyl group; or alternatively, a $C_1$ to $C_5$ organyl group; (b) a $C_1$ to $C_{30}$ organyl group comprising inert functional groups; alternatively, a $C_1$ to $C_{20}$ organyl group comprising inert functional groups; alternatively, a $C_1$ to $C_{15}$ organyl group comprising inert functional groups; alternatively, a $C_1$ to $C_{10}$ organyl group comprising inert functional groups; or alternatively, a $C_1$ to $C_5$ organyl group comprising inert functional groups; (c) a $C_1$ to $C_{30}$ hydrocarbyl group; alternatively, a $C_1$ to $C_{20}$ hydrocarbyl group; alternatively, a $C_1$ to $C_{15}$ hydrocarbyl group; alternatively, a $C_1$ to $C_{10}$ hydrocarbyl group; or alternatively, a $C_1$ to $C_5$ hydrocarbyl group; (d) a $C_1$ to $C_{30}$ alkyl group; alternatively, a $C_1$ to $C_{20}$ alkyl group; alternatively, a $C_1$ to $C_{15}$ alkyl group; alternatively, a $C_1$ to $C_{10}$ alkyl group; or alternatively, a $C_1$ to $C_5$ alkyl group; (e) a $C_6$ to $C_{30}$ aromatic group; alternatively, a $C_6$ to $C_{20}$ aromatic group; alternatively, a $C_6$ to $C_{15}$ aromatic group; or alternatively, a $C_6$ to $C_{10}$ aromatic group; (f) a phenyl group or a $C_6$ to $C_{30}$ substituted phenyl group; alternatively, a phenyl group or a $C_6$ to $C_{20}$ substituted phenyl group; alternatively, a phenyl group or a $C_6$ to $C_{15}$ substituted phenyl group; alternatively, a phenyl group or a $C_6$ to $C_{10}$ substituted phenyl group; or alternatively, a phenyl group; or (g) a substituted or an unsubstituted $C_1$ to $C_{20}$ alkyl group, $C_5$ to $C_{20}$ cycloalkyl group, or $C_6$-$C_{20}$ aromatic group; wherein any substituents are selected independently from a $C_1$ to $C_{10}$ hydrocarbyl group.

In this Structure PNP2, $R^{1n}$ and $R^{2n}$, and/or $R^{3n}$ and $R^{4n}$ of the diphosphino aminyl moiety can be joined to form a ring containing a phosphorus atom of the diphosphino aminyl moiety. For example, $R^{1n}$ and $R^{5n}$, or $R^{4n}$ and $R^{5n}$ of the diphosphino aminyl moiety can be joined to form a ring containing a phosphorus atom and the nitrogen atom of the diphosphino aminyl moiety.

The heteroatomic ligand also may comprise, can consist essentially of, or can be an $N^2$-phosphinyl formamidine compound having Structure NPF1, or an $N^2$-phosphinyl formamidine compound having Structure NPA1:

Structure NPF1

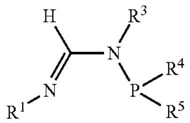

Structure NPA1

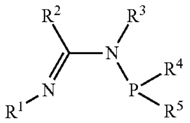

wherein $R^1$, $R^2$, $R^3$, $R^4$, and $R^5$ within Structure NPF1 and Structure NPFCr1 are independently (a)(i) a $C_1$ to $C_{30}$ organyl group, a $C_1$ to $C_{30}$ organyl group consisting essentially of inert functional groups, or a $C_1$ to $C_{30}$ hydrocarbyl group; (ii) a $C_1$ to $C_{20}$ organyl group, a $C_1$ to $C_{20}$ organyl group consisting essentially of inert functional groups, or a $C_1$ to $C_{20}$ hydrocarbyl group; (iii) a $C_1$ to $C_{15}$ organyl group, a $C_1$ to $C_{15}$ organyl group consisting essentially of inert functional groups, or a $C_1$ to $C_{15}$ hydrocarbyl group; (iv) a $C_1$ to $C_{10}$ organyl group, a $C_1$ to $C_{10}$ organyl group consisting essentially of inert functional groups, or a $C_1$ to $C_{10}$ hydrocarbyl group; or (v) a $C_1$ to $C_5$ organyl group, a $C_1$ to $C_5$ organyl group consisting essentially of inert functional groups, or a $C_1$ to $C_5$ hydrocarbyl group; (b) a $C_1$ to $C_{30}$ alkyl group; alternatively, a $C_1$ to $C_{20}$ alkyl group; alternatively, a $C_1$ to $C_{15}$ alkyl group; alternatively, a $C_1$ to $C_{10}$ alkyl group; or alternatively, a $C_1$ to $C_5$ alkyl group; (c) a $C_6$ to $C_{30}$ aromatic group; alternatively, a $C_6$ to $C_{20}$ aromatic group; alternatively, a $C_6$ to $C_{15}$ aromatic group; or alternatively, a $C_6$ to $C_{10}$ aromatic group; (d) a phenyl group or a $C_6$ to $C_{30}$ substituted phenyl group; alternatively, a phenyl group or a $C_6$ to $C_{20}$ substituted phenyl group; alternatively, a phenyl group or a $C_6$ to $C_{15}$ substituted phenyl group; or alternatively, a phenyl group or a $C_6$ to $C_{10}$ substituted phenyl group; or (e) a benzyl group or a $C_6$ to $C_{30}$ substituted benzyl group; alternatively, a benzyl group or a $C_6$ to $C_{20}$ substituted benzyl group; alternatively, a benzyl group or a $C_6$ to $C_{15}$ substituted benzyl group; or alternatively, a benzyl group or a $C_6$ to $C_{10}$ substituted benzyl group.

In view of the heteroatomic ligand disclosed herein and in another aspect, the chromium-containing compound complexed to an $N^2$-phosphinyl formamidine compound or the chromium-containing compound complexed to an $N^2$-phosphinyl amidine compound can have the following structures:

Structure NPFCr1

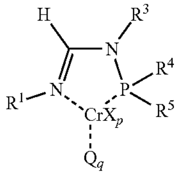

Structure NPACr1

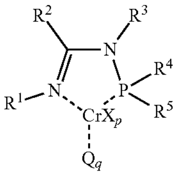

wherein X is an anionic ligand, and p is from 2 to 6, Q is a neutral ligand such as a nitrile ligand or an ether ligand, and q is from 0 to 6; and wherein $R^1$, $R^2$, $R^3$, $R^4$, and $R^5$ within Structure NPF1 and Structure NPFCr1 are independently (a)(i) a $C_1$ to $C_{30}$ organyl group, a $C_1$ to $C_{30}$ organyl group consisting essentially of inert functional groups, or a $C_1$ to $C_{30}$ hydrocarbyl group; (ii) a $C_1$ to $C_{20}$ organyl group, a $C_1$ to $C_{20}$ organyl group consisting essentially of inert functional groups, or a $C_1$ to $C_{20}$ hydrocarbyl group; (iii) a $C_1$ to $C_{15}$ organyl group, a $C_1$ to $C_{15}$ organyl group consisting essentially of inert functional groups, or a $C_1$ to $C_{15}$ hydrocarbyl group; (iv) a $C_1$ to $C_{10}$ organyl group, a $C_1$ to $C_{10}$ organyl group consisting essentially of inert functional groups, or a $C_1$ to $C_{10}$ hydrocarbyl group; or (v) a $C_1$ to $C_5$ organyl group, a $C_1$ to $C_5$ organyl group consisting essentially of inert functional groups, or a $C_1$ to $C_5$ hydrocarbyl group; (b) a $C_1$ to $C_{30}$ alkyl group; alternatively, a $C_1$ to $C_{20}$ alkyl group; alternatively, a $C_1$ to $C_{15}$ alkyl group; alternatively, a $C_1$ to $C_{10}$ alkyl group; or alternatively, a $C_1$ to $C_5$ alkyl group; (c) a $C_6$ to $C_{30}$ aromatic group; alternatively, a $C_6$ to $C_{20}$ aromatic group; alternatively, a $C_6$ to $C_{15}$ aromatic group; or alternatively, a $C_6$ to $C_{10}$ aromatic group; (d) a phenyl group or a $C_6$ to $C_{30}$ substituted phenyl group; alternatively, a phenyl group or a $C_6$ to $C_{20}$ substituted phenyl group; alternatively, a phenyl group or a $C_6$ to $C_{15}$ substituted phenyl group; or alternatively, a phenyl group or a $C_6$ to $C_{10}$ substituted phenyl group; or (e) a benzyl group or a $C_6$ to $C_{30}$ substituted benzyl group; alternatively, a benzyl group or a $C_6$ to $C_{20}$ substituted benzyl group; alternatively, a benzyl group or a $C_6$ to $C_{15}$ substituted benzyl group; or alternatively, a benzyl group or a $C_6$ to $C_{10}$ substituted benzyl group.

Referring to Structure NPF1 and Structure NPFCr1 as well as Structure NPF1 and Structure NPFCr1, in another aspect, $R^1$ is a $C_1$ to $C_{15}$ alkyl group, a $C_4$ to $C_{20}$ cycloalkyl group, a $C_4$ to $C_{20}$ substituted cycloalkyl group, a $C_6$ to $C_{20}$ aryl group, or a $C_6$ to $C_{20}$ substituted aryl group; $R^2$ is a $C_1$ to $C_{30}$ organyl group consisting essentially of inert functional groups wherein the inert functional groups are selected from halo groups, nitro groups, hydrocarboxy groups, sulfidyl groups, hydrocarbyl groups, or combinations thereof; $R^3$ is hydrogen, and $R^4$ and $R^5$ are each independently a $C_1$ to $C_{30}$ organyl group consisting essentially of inert functional groups wherein the inert functional groups are selected from halo groups, nitro groups, hydrocarboxy groups, sulfidyl groups, hydrocarbyl groups, or combinations thereof.

In any of the heteroatomic ligands disclosed herein, any substituent of a substituted group can be selected from (a) a halide, a hydrocarbyl group, or a hydrocarboxy group; alternatively, a halide or a hydrocarbyl group; (b) a $C_1$ to $C_{10}$ hydrocarbyl group or a $C_1$ to $C_{10}$ hydrocarboxy group; alternatively, a halide or a $C_1$ to $C_{10}$ hydrocarbyl group; alternatively, a halide or a $C_1$ to $C_{10}$ hydrocarboxy group; alternatively, a $C_1$ to $C_{10}$ hydrocarbyl group or a $C_1$ to $C_{10}$ hydrocarboxy group; alternatively, a halide; alternatively, a $C_1$ to $C_{10}$ hydrocarbyl group; or alternatively, a $C_1$ to $C_{10}$ hydrocarboxy group.

In the processes for making an aviation fuel, the first catalyst system, the second catalyst system, or both independently can further comprise a metal alkyl compound, which can include an organoaluminum compound such as a trialkylaluminum compound or an organoaluminoxane. For example, the organoaluminum compound can comprise, consist essentially of, or be selected from a triorganoaluminum compound, a diorganoaluminum halide, an organoaluminum dihalide, a diorganoaluminum alkoxide, an organoaluminum dialkoxide, an aluminoxane, or combinations thereof. In an aspect, the organoaluminum compound can have a general formula $Al(R^{10})_n(X^{11})_{3-n}$, wherein n is from 1 to 3 inclusive; each $R^{10}$ is independently a $C_1$ to $C_{20}$ hydrocarbyl; and $X^{11}$ is independently a halide, a hydride, a $C_1$ to $C_{20}$ hydrocarbyl, or a $C_1$ to $C_{20}$ hydrocarbyloxide. For example, the organoaluminum compound organoaluminum compound can comprise, consist essentially of, or can be selected from trimethylaluminum, triethylaluminum, tri-n-propylaluminum, tri-n-butylaluminum, triisobutylaluminum, tri-n-hexylaluminum, tri-n-octylaluminum, diisobutylaluminum hydride, diethylaluminum ethoxide, diethylaluminum chloride, or any combination thereof.

In a further aspect, the organoaluminum compound can comprise, consist essentially of, or can be selected from an aluminoxane compound. For example, the organoaluminum compound can comprise, consist essentially of, or be selected from at least one aluminoxane compound, and wherein the aluminoxane comprises a cyclic aluminoxane having the formula

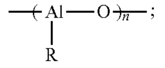

wherein R is a linear or branched alkyl having from 1 to 10 carbon atoms, and n is an integer from 3 to about 10; a linear aluminoxane having the formula

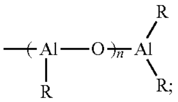

wherein R is a linear or branched alkyl having from 1 to 10 carbon atoms, and n is an integer from 1 to about 50; a cage aluminoxane having the formula $R^t_{5m+\alpha}R^b_{m-\alpha}Al_{4m}O_{3m}$, wherein m is 3 or 4 and $\alpha=n_{Al(3)}-n_{O(2)}+n_{O(4)}$; wherein $n_{Al(3)}$ is the number of three coordinate aluminum atoms, $n_{O(2)}$ is the number of two coordinate oxygen atoms, $n_{O(4)}$ is the number of 4 coordinate oxygen atoms, $R^t$ represents a terminal alkyl group, and $R^b$ represents a bridging alkyl group; wherein R is a linear or branched alkyl having from 1 to 10 carbon atoms; or any combination thereof. In another aspect, the organoaluminum compound can comprise, consist essentially of, or be selected from an aluminoxane having the formula $(R^C—Al—O)_t$ or $R^C(R^C—Al—O)_tAl(R^C)_2$, wherein $R^C$ is a linear or branched $C_1$-$C_6$ alkyl such as methyl, ethyl, propyl, butyl, pentyl, or hexyl wherein t is an integer from 1 to 50, inclusive, or t is an integer from 2 to 20.

Examples of organoaluminoxane compounds can include, but are not limited to, the following. In an aspect, the organoaluminum compound can comprise, consist essentially of, or can be selected from methylaluminoxane (MAO), ethylaluminoxane, modified methylaluminoxane (MMAO) such as an isobutyl-modified methyl alumoxane, n-propylaluminoxane, iso-propylaluminoxane, n-butylaluminoxane, t-butylaluminoxane, sec-butylaluminoxane, isobutylaluminoxane, t-butyl aluminoxane, 1-pentylaluminoxane, 2-pentylaluminoxane, 3-pentylaluminoxane, isopentylaluminoxane, neopentylaluminoxane, or any combinations thereof.

As described herein, the chromium-based catalyst can comprise or can consist essentially of (a) a chromium-containing compound, (b) a heteroatomic ligand, (c) a metal alkyl compound, and (d) optionally, a diluent. Other catalyst systems described herein can optionally include a diluent if at least a portion of the reaction process is conducted in solution or a slurry. Therefore in an aspect, the first catalyst system, the second catalyst system, or both independently can comprise a diluent. For example, the diluent can comprise, consist essentially of, or be selected from a hydrocarbon, a halogenated hydrocarbon, or combinations thereof. In another aspect, the diluent can comprise, consist essentially of, or be selected from a cyclic diluent, an acyclic diluent, or combinations thereof. In another aspect, the diluent can comprise, consist essentially of, or be selected from a linear diluent, a branched diluent, or combinations thereof.

The diluent used according to this disclosure can also comprise, consist essentially of, or be selected from aliphatic hydrocarbons, aromatic hydrocarbons, petroleum distillates, halogenated aliphatic hydrocarbons, halogenated aromatic hydrocarbons, or combinations thereof. For example, the diluent can comprise, consist essentially of, or be selected from a $C_3$ to $C_8$ linear or branched acyclic aliphatic hydrocarbon, $C_6$ to $C_{10}$ aromatic hydrocarbons, $C_1$ to $C_{15}$ halogenated aliphatic hydrocarbons, $C_1$ to $C_{10}$ halogenated aliphatic hydrocarbons, $C_1$ to $C_5$ halogenated aliphatic hydrocarbons, $C_6$ to $C_{20}$ halogenated aromatic hydrocarbons, $C_6$ to $C_{10}$ halogenated aromatic hydrocarbons, or combinations thereof.

In a further aspect, the diluent can comprise, consist essentially of, or be selected from a propane, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), hexane (n-hexane or mixture of linear and branched $C_6$ acyclic aliphatic hydrocarbons), heptane (n-heptane or a mixture of linear and branched $C_7$ acyclic aliphatic hydrocarbons), octane (n-octane or a mixture of linear and branched $C_8$ acyclic aliphatic hydrocarbons), cyclohexane, methyl cyclohexane, benzene, toluene, xylene (including ortho-xylene, meta-xylene, para-xylene, or mixtures thereof), ethylbenzene, methylene chloride, chloroform, carbon tetrachloride, dichloroethane, trichloroethane, chlorobenzene, dichlorobenzene, or combinations thereof, which represent examples of suitable diluents.

Oligomerization Conditions

In the process for making an aviation fuel according to this disclosure, the oligomerization conditions can vary according to the olefin stream, the catalyst, and the like. In an aspect, contacting the ethylene feed with the first catalyst system can be carried out at a total pressure of from 0 psig (0 KPa) to 2,500 psig (17.3 MPa); alternatively, from 0 psig (KPa) to 1,600 psig (11.0 MPa); alternatively, from 0 psig (KPa) to 1,500 psig (10.4 MPa); alternatively, from 50 psig (344 KPa) to 2,500 psig (17.3 MPa); alternatively, from 100 psig (689 KPa) to 2,500 psig (17.3 MPa); alternatively, from 150 psig (1.0 MPa) to 2,000 psig (13.8 MPa); or alternatively, from 300 psig (2.0 MPa) to 900 psig (6.2 MPa). In another aspect, wherein at least a portion of the ethylene feed is a bio-ethylene feed, contacting the ethylene feed with the first catalyst system can occur at a bio-ethylene feed pressure of from 0 psig (0 KPa) to 2,500 psig (17.3 MPa); alternatively, from 50 psig (344 KPa) to 2,500 psig (17.3 MPa); alternatively, from 100 psig (689 KPa) to 2,500 psig (17.3 MPa); or alternatively, from 150 psig (1.0 MPa) to 2,000 psig (13.8 MPa).

Contacting the ethylene feed with the first catalyst system can occur at any temperature which effects the desired oligomerization reactions. For example, contacting the ethylene feed (and optionally, at least a portion of the ethylene feed can be a bio-ethylene feed) with the first catalyst system can occur at a temperature of at least 0° C.; alternatively, at least 10° C.; alternatively, at least 20° C.; alternatively, at least 30° C.; alternatively, at least 40° C.; alternatively, at least 50° C.; alternatively, at least 60° C.; alternatively, at least 70° C.; alternatively, at least 80° C.; alternatively, at least 90° C.; alternatively, at least 100° C.; alternatively, at least 110° C.; alternatively, at least 120° C.; alternatively, at least 130° C.; alternatively, at least 140° C.; alternatively, at least 150° C.; alternatively, at least 160° C.; alternatively, at least 170° C.; or alternatively, at least 180° C. The step of contacting the ethylene feed with the first catalyst system can occur at a temperature of less than 180° C.; alternatively, less than 160° C.; alternatively, less than 140° C.; alternatively, less than 120° C.; alternatively, less than 100° C.; alternatively, less than 90° C.; or alternatively, less than 80° C.

In other aspects, contacting the ethylene feed (and optionally, at least a portion of the ethylene feed can be a bio-ethylene feed) with the first catalyst system can occur at a temperature within a range of from 0° C. to 180° C.; alternatively, from 10° C. to 160° C.; alternatively, from 20° C. to 140° C.; alternatively, from 30° C. to 120° C.; alternatively, from 40° C. to 100° C.; alternatively, from 50° C. to 100° C.; or alternatively, from 60° C. to 140° C.

Biomass Ethanol and Bio-Ethylene

Biomass ethanol produced by any process can be used according to this disclosure. Biomass ethanol, including the fuel ethanol for blending with gasoline, is largely produced by fermenting the grain starch and sugars from sources such as corn, sorghum, and barley. Other feedstocks for the production of biomass ethanol include agriculture residues such as corn stalks, rice stalks, and grasses such as switchgrass, and ethanol from these sources is also termed cellulosic ethanol as it derives from lignocellulosic biomass. Microorganisms such as yeast (e.g., *Saccharomyces* species) can be employed to produce ethanol via fermentation of sugars, either directly extracted from sources such as sugarcanes and sugar beet juices or obtained via hydrolysis of starchy materials such as corn and grains. Bacteria (e.g., *Zymomonas* species) and molds (e.g., *Mucor* species) may also be used to produce biomass ethanol. The ethanol produced in this manner can then be separated by distillation.

Gas obtained from a biomass feedstock is primarily a gaseous mixture of methane and carbon dioxide, with traces of other gases. This bio-syngas can be produced by the thermal gasification (in gasifiers) of various organic feedstocks. This bio-syngas may also be termed biosynthetic gas or bio-SNG.

In an aspect, the biomass ethanol according to this disclosure can be produced from a starch-based feedstock, a sugar-based feedstock, or a cellulosic feedstock, or from a bio-syngas to ethanol process. For example, the biomass ethanol can be produced by the fermentation of sugars derived from a starch-based feedstock or a sugar-based feedstock. The biomass ethanol also may be produced by the fermentation of a carbohydrate derived from a starch-based feedstock, a sugar-based feedstock, or a cellulosic feedstock. For example, suitable starch-based feedstocks include barley, cassava root, corn, potato, rice, sorghum grain, sweet potato, wheat, rye, or any combination thereof. In another aspect, suitable sugar-based feedstocks can include sugar cane, sugar beet, sweet sorghum, molasses, fruit, or any combination thereof.

The biomass ethanol also can be produced from a starch-based feedstock by a process comprising the enzymatic hydrolysis of the starch-based feedstock to produce sugars, followed by yeast fermentation of the sugars. In another aspect, the biomass ethanol can be produced from cellulosic feedstock. In this aspect, the cellulosic feedstock can comprise or be selected from corn stover, wheat straw, sugar cane bagasse, switchgrass, or wood chips, or any combination thereof.

The dehydration of the biomass ethanol to bio-ethylene can comprise simply contacting the biomass ethanol with a dehydration catalyst under conditions suitable to form bio-ethylene. For example, the dehydration of the biomass ethanol can comprise passing liquid phase ethanol through a bed comprising the dehydration catalyst. This process can further comprise regenerating the dehydration catalyst by heating the catalyst after use at atmosphere pressure or at reduced pressure.

In an aspect, the dehydration catalyst which can convert biomass ethanol to bio-ethylene can comprise, consist essentially of, or can be selected from alumina, silica gel, silica-alumina, a crystalline silicate, a dealuminated crystalline silicate, a phosphorus-modified crystalline silicate, a zeolite, a molecular sieve, or anhydrous calcium sulfate, or combinations thereof. In some aspects, the dehydration catalyst can comprise, consist essentially of, or can be a lanthanum-modified H-ZSM-catalyst, a ZSM-5/SAPO-34 composite, a mordenite catalyst, a microspherical SAPO-34 catalyst, a phosphorus-modified HZSM-5 catalyst, a lanthanum-phosphorous modified HZSM-5 catalyst, a gallium-modified zeolite, a gallium-modified SAPO-11, a gallium-modified HZSM-5, a ZSM-based catalyst, a heteropolyacid catalyst, or a supported heteropolyacid catalyst. For example, in an aspect, the dehydration catalyst can comprise, consist essentially of, or can be a ZSM-5 zeolite comprising from 0.1 wt. % to 0.5 wt. % of lanthanum and from 0.01 wt. % to 1 wt. % phosphorous, relative to the weight of the catalyst, and wherein the ZSM-5 has a silica to alumina molar ratio of, for example, from 20 to 45.

Hydrogenation

The hydrogenation of olefins is well understood, and any suitable hydrogenation catalyst can be used in the hydrogenation of the mixture of decenes and in the hydrogenation of the $C_{16-}$ olefin stream, and other olefin streams. For example, in an aspect, the first hydrogenation catalyst, the second hydrogenation catalyst, or both independently can comprise, consist essentially of, or can be a nickel or a nickel-containing hydrogenation catalyst, a platinum or a platinum-containing hydrogenation catalyst, or a palladium or a palladium-containing hydrogenation catalyst.

The first hydrogenation catalyst, the second hydrogenation catalyst, or both independently can comprise, consist essentially of, or can be (a) a heterogeneous catalyst selected from a Group 8-12 metal deposited on a carrier selected from carbon, silica, alumina, silica-alumina, a zeolite, or calcium carbonate; or (b) a homogeneous catalyst selected from (i) a Ziegler catalyst comprising an organic salt of a Group 6-10 metal and an organoaluminum compound, or (ii) a coordination compound of Ru, Rh, or Ir, or (iii) a Group 4 metal organometallic compound. In an aspect, (a) the Group 8-12 metal of the heterogeneous catalyst can be selected from Fe, Co, Ni, Cu, Zn, Ru, Rh, Pd, Ir, or Pt; (b) the Group 6-10 metal of the homogeneous catalyst can be selected from Ni, Co, Fe, or Cr; or (c) the Group 4 metal organometallic compound can be selected from a Group 4 metallocene compound. For example, in certain aspects, the first hydrogenation catalyst, the second hydrogenation catalyst, or both independently can comprise one or more metals selected from cobalt, molybdenum, nickel, and/or tungsten.

Olefin and Alkane Compositions

Olefin and alkane compositions produced from one or more of the processes of this invention also are encompassed herein. A first $C_{13}$ olefin composition can be derived from (e.g., $BF_3$—ROH catalyzed) propylene addition to mixed decenes (e.g., 2-butyl-1-hexene, 3-propyl-1-heptene, 4-ethyl-1-octene, and 5-methyl-1-nonene), and the first olefin composition (or a $C_{16-}$ olefin stream produced by any of the processes disclosed herein) can comprise 2-methyl-4-butyl-3-octene, 2-methyl-5-propylnon-3-ene, 6-ethyl-2-methyldec-3-ene, and/or 2,7-dimethylundec-3-ene. Thus, the first olefin composition (or the $C_{16-}$ olefin stream produced by any of the processes disclosed herein) can comprise 2-methyl-4-butyl-3-octene, 2-methyl-5-propylnon-3-ene, 6-ethyl-2-methyldec-3-ene, and 2,7-dimethylundec-3-ene, or alternatively, the first olefin composition (or the $C_{16-}$ olefin stream produced by any of the processes disclosed herein) can comprise any combination of 2-methyl-4-butyl-3-octene, 2-methyl-5-propylnon-3-ene, 6-ethyl-2-methyldec-3-ene, and 2,7-dimethylundec-3-ene. An analogous first $C_{13}$ alkane composition (or $C_{16-}$ paraffins produced by any of the processes disclosed herein) can be formed via hydrogenation of the first olefin composition (or the $C_{16-}$ olefin stream), and the first alkane composition (or the $C_{16-}$ paraffins) can comprise 5-isobutylnonane, 2-methyl-5-propylnonane, 6-ethyl-2-methyldecane, and 2,7-dimethylundecane, or alternatively, the first alkane composition (or the $C_{16-}$ paraffins) can comprise any combination of 5-isobutylnonane, 2-methyl-5-propylnonane, 6-ethyl-2-methyldecane, and 2,7-dimethylundecane. The olefin addition reaction scheme for the reaction of $C_{10}$ olefins with propylene to form the first $C_{13}$ olefin composition (or the $C_{16-}$ olefin stream) and the first $C_{13}$ alkane composition (or the $C_{16-}$ paraffins) is illustrated in FIG. 1.

Figure 2:
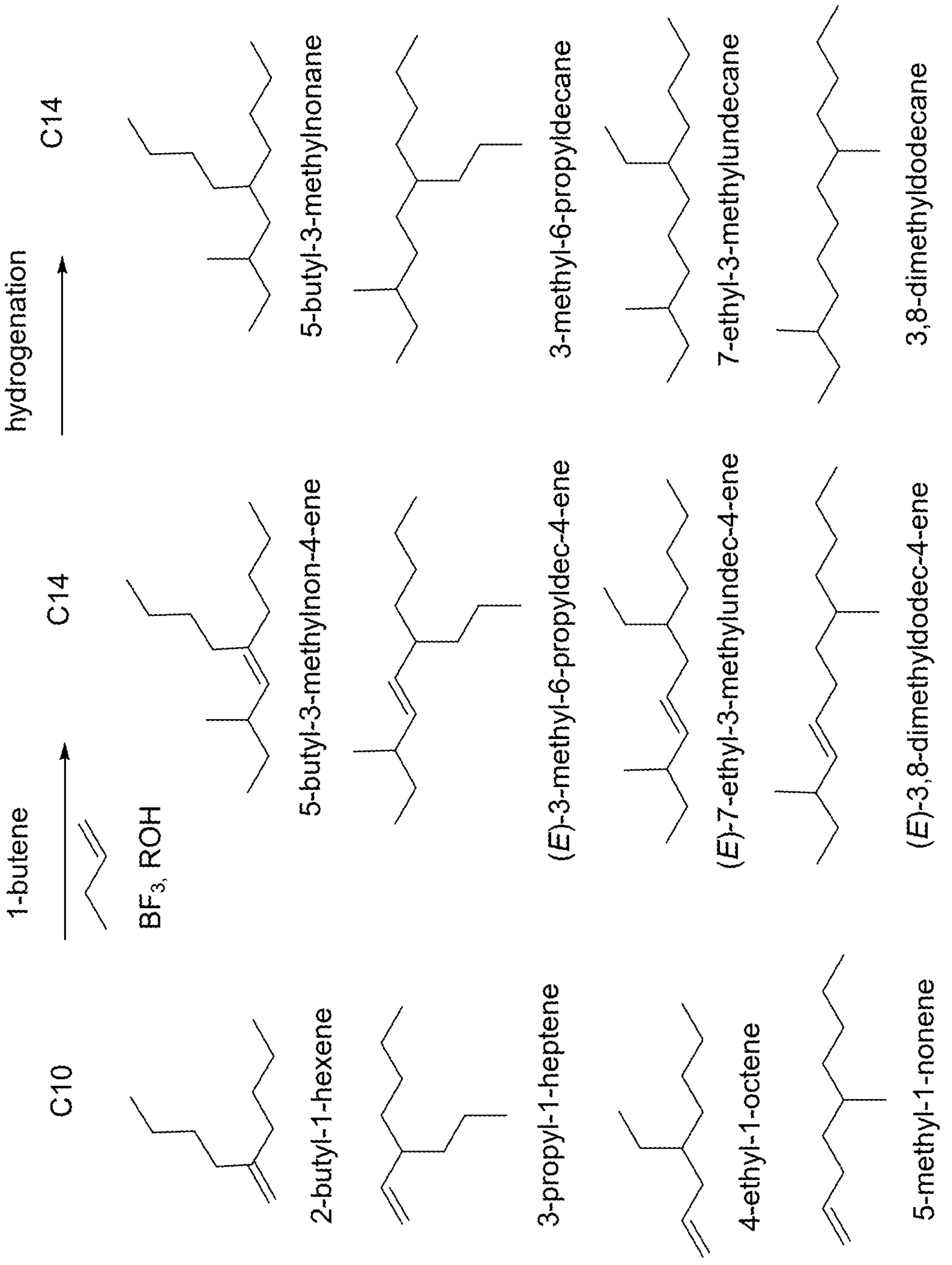
FIG. 2 is an olefin addition reaction scheme for the reaction of $C_{10}$ olefins with 1-butene to form $C_{14}$ olefins and subsequent hydrogenation to from $C_{14}$ alkanes.

A second $C_{14}$ olefin composition can be derived from (e.g., $BF_3$—ROH catalyzed) 1-butene addition to mixed decenes (e.g., 2-butyl-1-hexene, 3-propyl-1-heptene, 4-ethyl-1-octene, and 5-methyl-1-nonene), and the second olefin composition (or a $C_{16-}$ olefin stream produced by any of the processes disclosed herein) can comprise 5-butyl-3-methylnon-4-ene, 3-methyl-6-propyldec-4-ene, 7-ethyl-3-methylundec-4-ene, and/or 3,8-dimethyldodec-4-ene. Thus, the second olefin composition (or the $C_{16-}$ olefin stream produced by any of the processes disclosed herein) can comprise 5-butyl-3-methylnon-4-ene, 3-methyl-6-propyldec-4-ene, 7-ethyl-3-methylundec-4-ene, and 3,8-dimethyldodec-4-ene, or alternatively, the second olefin composition (or the $C_{16-}$ olefin stream produced by any of the processes disclosed herein) can comprise any combination of 5-butyl-3-methylnon-4-ene, 3-methyl-6-propyldec-4-ene, 7-ethyl-3-methylundec-4-ene, and 3,8-dimethyldodec-4-ene. An analogous second $C_{14}$ alkane composition (or $C_{16-}$ paraffins produced by any of the processes disclosed herein) can be formed via hydrogenation of the second olefin composition (or the $C_{16-}$ olefin stream), and the second alkane composition (or the $C_{16-}$ paraffins) can comprise 5-butyl-3-methylnonane, 3-methyl-6-propyldecane, 7-ethyl-3-methylundecane, and 3,8-dimethyldodecane, or alternatively, the second alkane composition (or the $C_{16-}$ paraffins) can comprise any combination of 5-butyl-3-methylnonane, 3-methyl-6-propyldecane, 7-ethyl-3-methylundecane, and 3,8-dimethyldodecane. The olefin addition reaction scheme for the reaction of $C_{10}$ olefins with 1-butene to form the second $C_{14}$ olefin composition (or the $C_{16-}$ olefin stream) and the second $C_{14}$ alkane composition (or the $C_{16-}$ paraffins) is illustrated in FIG. 2.

Figure 3:
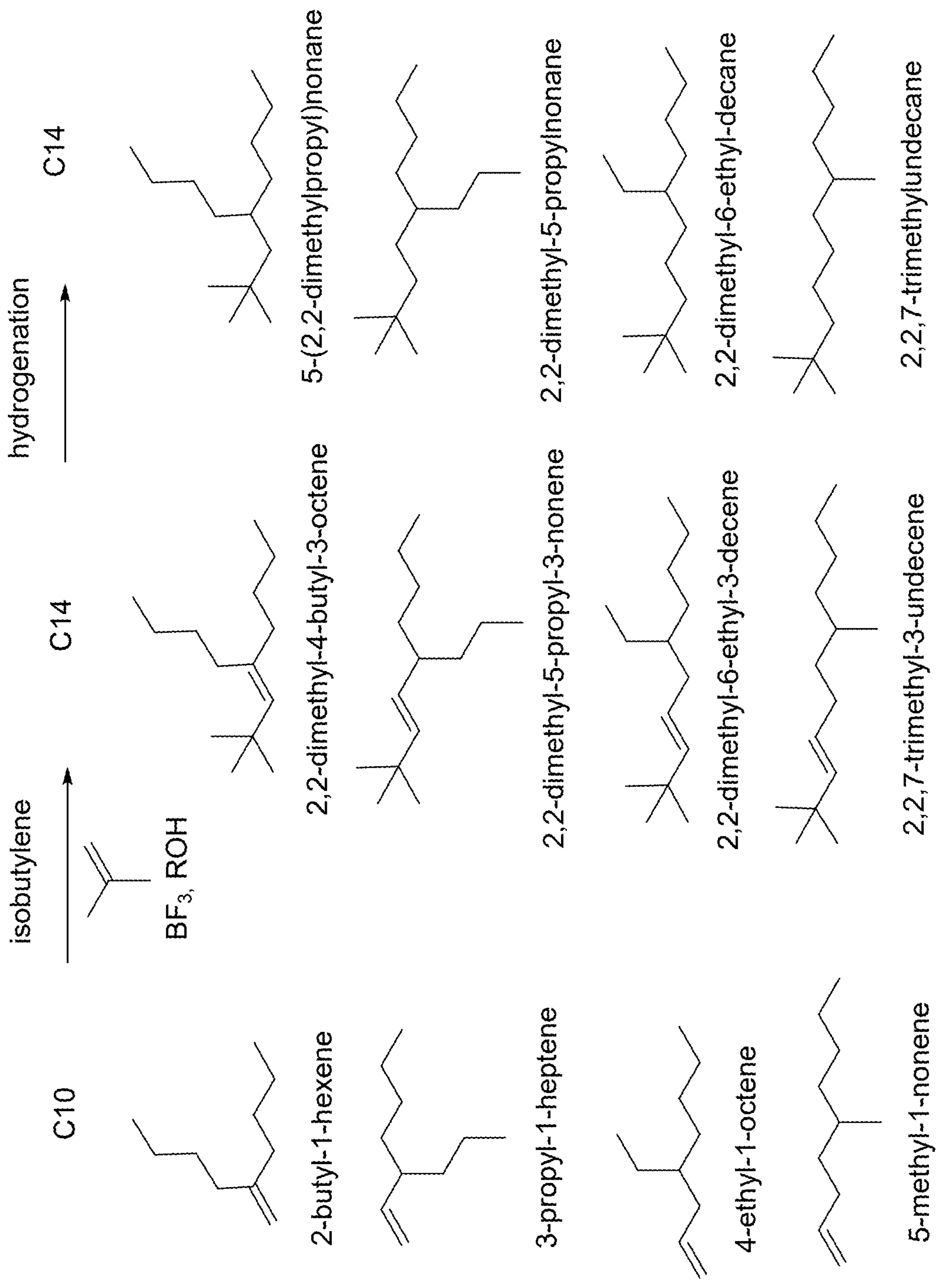
FIG. 3 is an olefin addition reaction scheme for the reaction of $C_{10}$ olefins with isobutylene to form $C_{14}$ olefins and subsequent hydrogenation to from $C_{14}$ alkanes.

A third $C_{14}$ olefin composition can be derived from (e.g., $BF_3$—ROH catalyzed) isobutylene addition to mixed decenes (e.g., 2-butyl-1-hexene, 3-propyl-1-heptene, 4-ethyl-1-octene, and 5-methyl-1-nonene), and the third olefin composition (or a $C_{16-}$ olefin stream produced by any of the processes disclosed herein) can comprise 2,2-dimethyl-4-butyl-3-octene, 2,2-dimethyl-5-propyl-3-nonene, 2,2-dimethyl-6-ethyl-3-decene, and/or 2,2,7-trimethyl-3-undecene. Thus, the third olefin composition (or the $C_{16-}$ olefin stream produced by any of the processes disclosed herein) can comprise 2,2-dimethyl-4-butyl-3-octene, 2,2-dimethyl-5-propyl-3-nonene, 2,2-dimethyl-6-ethyl-3-decene, and 2,2,7-trimethyl-3-undecene, or alternatively, the third olefin composition (or the $C_{16-}$ olefin stream produced by any of the processes disclosed herein) can comprise any combination of 2,2-dimethyl-4-butyl-3-octene, 2,2-dimethyl-5-propyl-3-nonene, 2,2-dimethyl-6-ethyl-3-decene, and 2,2,7-trimethyl-3-undecene. An analogous third $C_{14}$ alkane composition (or $C_{16-}$ paraffins produced by any of the processes disclosed herein) can be formed via hydrogenation of the third olefin composition (or the $C_{16-}$ olefin stream), and the third alkane composition (or the $C_{16-}$ paraffins) can comprise 5-(2,2-dimethylpropyl)nonane, 2,2-dimethyl-5-propylnonane, 2,2-dimethyl-6-ethyl-decane, and 2,2,7-trimethylundecane, or alternatively, the third alkane composition (or the $C_{16-}$ paraffins) can comprise any combination of 5-(2,2-dimethylpropyl)nonane, 2,2-dimethyl-5-propylnonane, 2,2-dimethyl-6-ethyl-decane, and 2,2,7-trimethylundecane. The olefin addition reaction scheme for the reaction of $C_{10}$ olefins with isobutylene to form the third $C_{14}$ olefin composition (or the $C_{16-}$ olefin stream) and the third $C_{14}$ alkane composition (or the $C_{16-}$ paraffins) is illustrated in FIG. 3.

Figure 4:
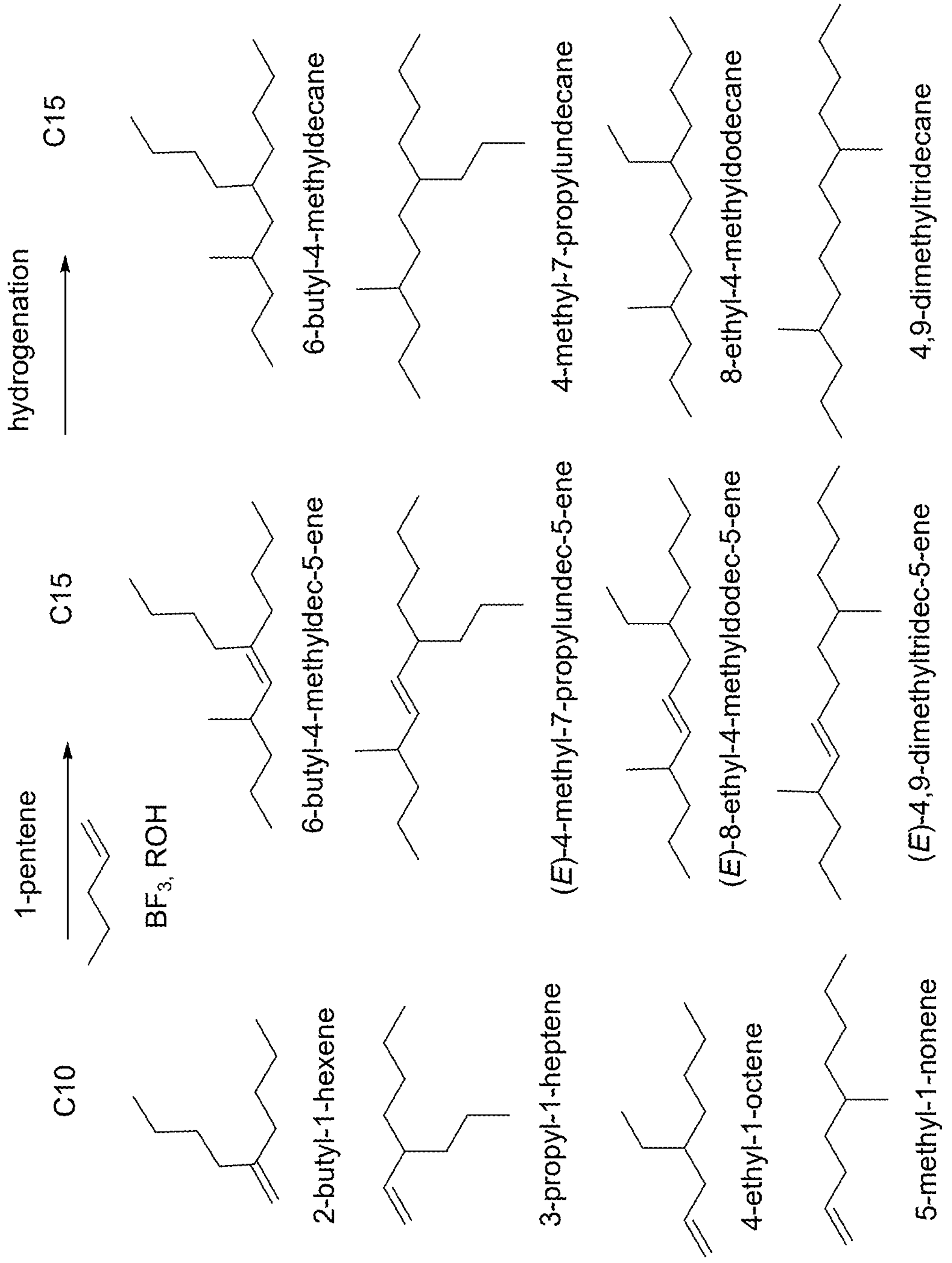
FIG. 4 is an olefin addition reaction scheme for the reaction of $C_{10}$ olefins with 1-pentene to form $C_{15}$ olefins and subsequent hydrogenation to from $C_{15}$ alkanes.

A fourth $C_{15}$ olefin composition can be derived from (e.g., $BF_3$—ROH catalyzed) 1-pentene addition to mixed decenes (e.g., 2-butyl-1-hexene, 3-propyl-1-heptene, 4-ethyl-1-octene, and 5-methyl-1-nonene), and the fourth olefin composition (or a $C_{16-}$ olefin stream produced by any of the processes disclosed herein) can comprise 6-butyl-4-methyldec-5-ene, 4-methyl-7-propylundec-5-ene, 8-ethyl-4-methyldodec-5-ene, and/or 4,9-dimethyltridec-5-ene. Thus, the fourth olefin composition (or the $C_{16-}$ olefin stream produced by any of the processes disclosed herein) can comprise 6-butyl-4-methyldec-5-ene, 4-methyl-7-propylundec-5-ene, 8-ethyl-4-methyldodec-5-ene, and 4,9-dimethyltridec-5-ene, or alternatively, the fourth olefin composition (or the $C_{16-}$ olefin stream produced by any of the processes disclosed herein) can comprise any combination of 6-butyl-4-methyldec-5-ene, 4-methyl-7-propylundec-5-ene, 8-ethyl-4-methyldodec-5-ene, and 4,9-dimethyltridec-5-ene. An analogous fourth $C_{15}$ alkane composition (or $C_{16-}$ paraffins produced by any of the processes disclosed herein) can be formed via hydrogenation of the fourth olefin composition (or the $C_{16-}$ olefin stream), and the fourth alkane composition (or the $C_{16-}$ paraffins) can comprise 6-butyl-4-methyldecane, 4-methyl-7-propylundecane, 8-ethyl-4-methyldodecane, and 4,9-dimethyltridecane, or alternatively, the fourth alkane composition (or the $C_{16-}$ paraffins) can comprise any combination of 6-butyl-4-methyldecane, 4-methyl-7-propylundecane, 8-ethyl-4-methyldodecane, and 4,9-dimethyltridecane. The olefin addition reaction scheme for the reaction of $C_{10}$ olefins with 1-pentene to form the fourth $C_{15}$ olefin composition (or the $C_{16-}$ olefin stream) and the fourth $C_{15}$ alkane composition (or the $C_{16-}$ paraffins) is illustrated in FIG. 4.

Figure 5:
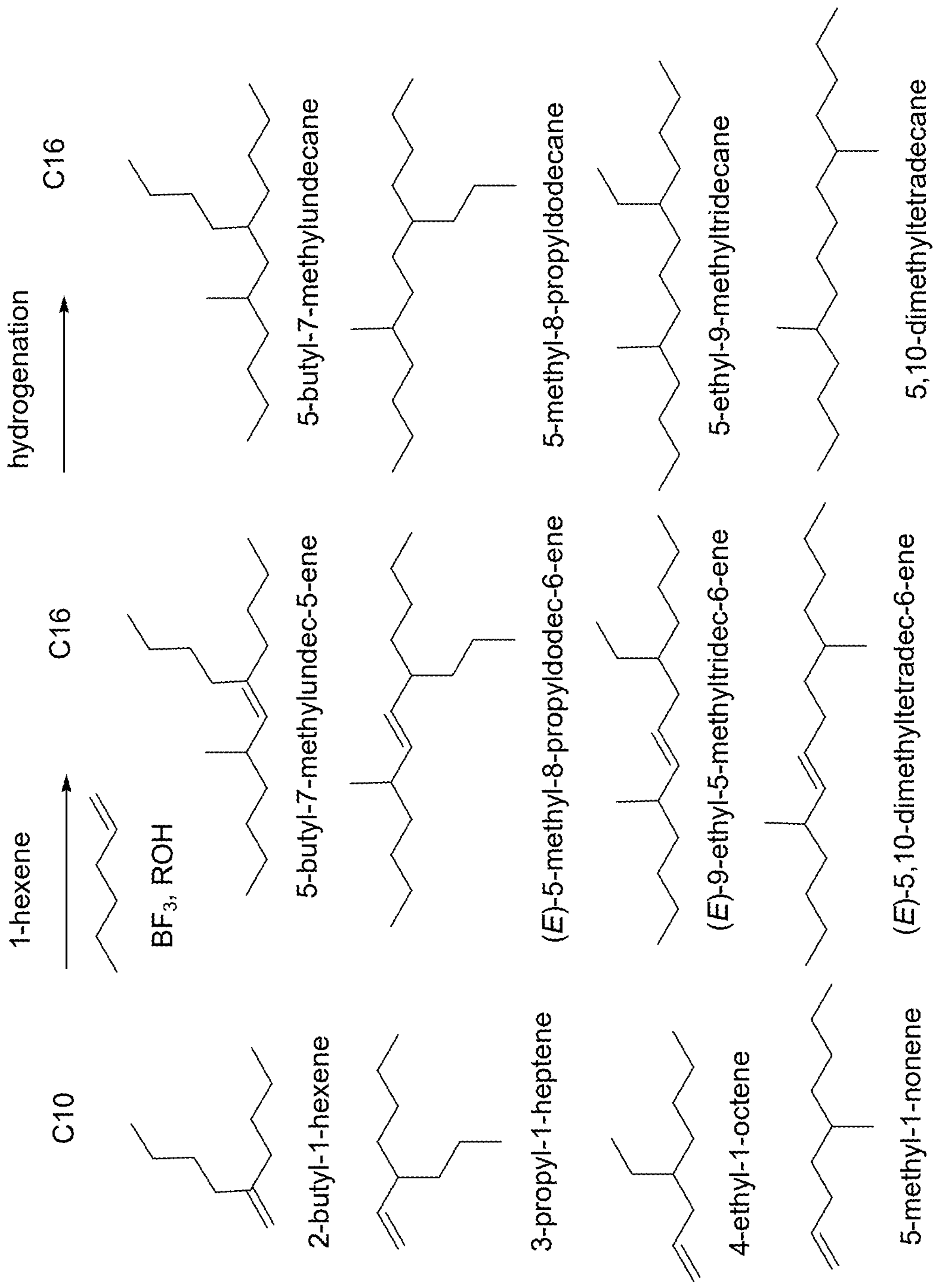
FIG. 5 is an olefin addition reaction scheme for the reaction of $C_{10}$ olefins with 1-hexene to form $C_{16}$ olefins and subsequent hydrogenation to from $C_{16}$ alkanes.

A fifth $C_{16}$ olefin composition can be derived from (e.g., $BF_3$—ROH catalyzed) 1-hexene addition to mixed decenes (e.g., 2-butyl-1-hexene, 3-propyl-1-heptene, 4-ethyl-1-octene, and 5-methyl-1-nonene), and the firth olefin composition (or a $C_{16-}$ olefin stream produced by any of the processes disclosed herein) can comprise 5-butyl-7-methylundec-5-ene, 5-methyl-8-propyldodec-6-ene, 9-ethyl-5-methyltridec-6-ene, and/or 5,10-dimethyltetradec-6-ene. Thus, the fifth olefin composition (or the $C_{16-}$ olefin stream produced by any of the processes disclosed herein) can comprise 5-butyl-7-methylundec-5-ene, 5-methyl-8-propyldodec-6-ene, 9-ethyl-5-methyltridec-6-ene, and 5,10-dimethyltetradec-6-ene, or alternatively, the fifth olefin composition (or the $C_{16-}$ olefin stream produced by any of the processes disclosed herein) can comprise any combination of 5-butyl-7-methylundec-5-ene, 5-methyl-8-propyldodec-6-ene, 9-ethyl-5-methyltridec-6-ene, and 5,10-dimethyltetradec-6-ene. An analogous fifth $C_{16}$ alkane composition (or $C_{16-}$ paraffins produced by any of the processes disclosed herein) can be formed via hydrogenation of the fifth olefin composition (or the $C_{16-}$ olefin stream), and the fifth alkane composition (or the $C_{16-}$ paraffins) can comprise 5-butyl-7-methylundecane, 5-methyl-8-propyldodecane, 5-ethyl-9-methyltridecane, and 5,10-dimethyltetradecane, or alternatively, the fifth alkane composition (or the $C_{16-}$ paraffins) can comprise any combination of 5-butyl-7-methylundecane, 5-methyl-8-propyldodecane, 5-ethyl-9-methyltridecane, and 5,10-dimethyltetradecane. The olefin addition reaction scheme for the reaction of $C_{10}$ olefins with 1-hexene to form the fifth $C_{16}$ olefin composition (or the $C_{16-}$ olefin stream) and the fifth $C_{16}$ alkane composition (or the $C_{16-}$ paraffins) is illustrated in FIG. 5.

Figure 6:
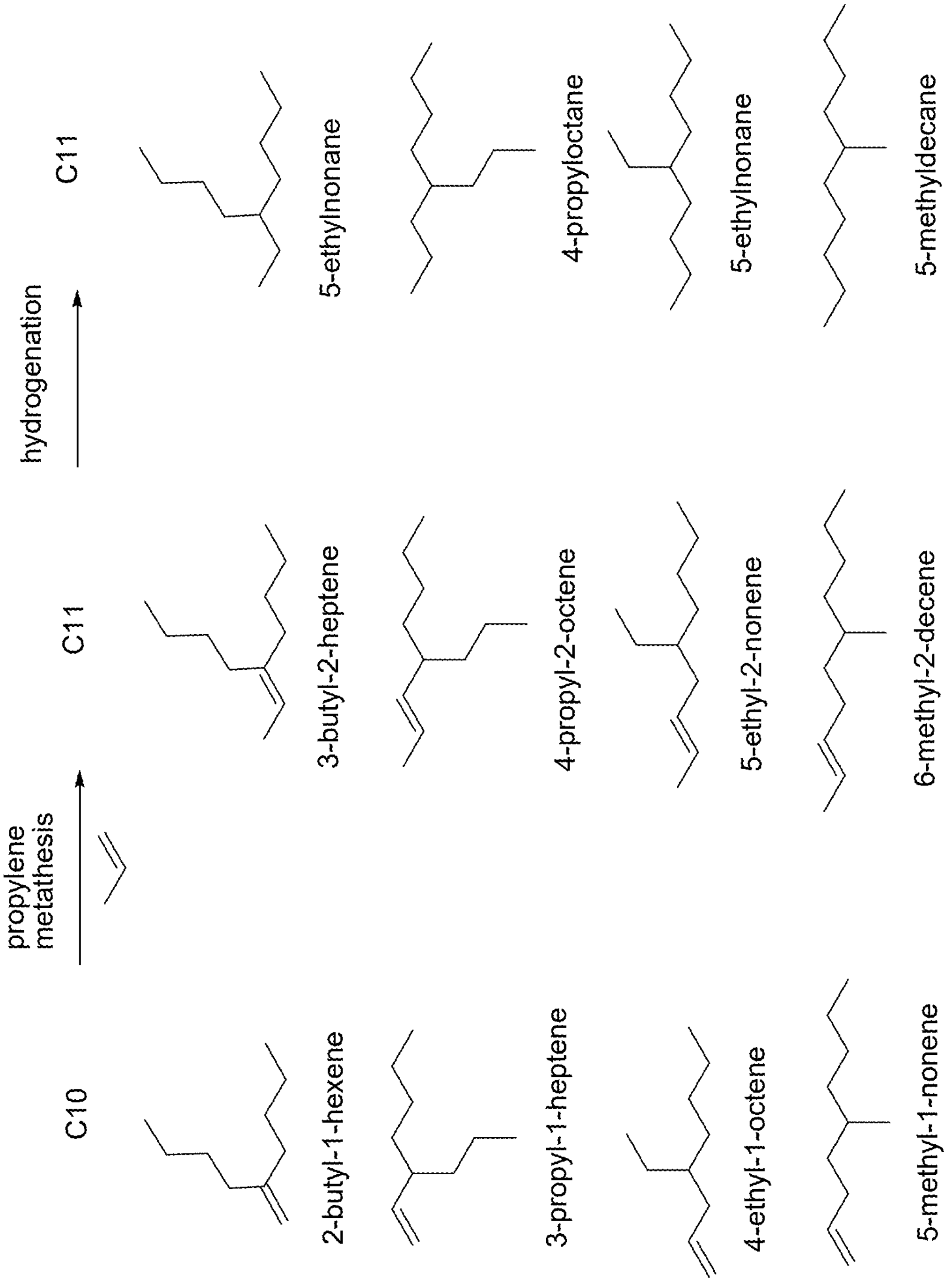
FIG. 6 is a metathesis reaction scheme for the reaction of $C_{10}$ olefins with propylene to form $C_{11}$ olefins and subsequent hydrogenation to from $C_{11}$ alkanes.

A sixth $C_{11}$ olefin composition can be derived from propylene metathesis with mixed decenes (e.g., 2-butyl-1-hexene, 3-propyl-1-heptene, 4-ethyl-1-octene, and 5-methyl-1-nonene), and the sixth olefin composition (or a $C_{16-}$ olefin stream produced by any of the processes disclosed herein) can comprise 3-butyl-2-heptene, 4-propyl-2-octene, 5-ethyl-2-nonene, and/or 6-methyl-2-decene. Thus, the sixth olefin composition (or the $C_{16-}$ olefin stream produced by any of the processes disclosed herein) can comprise 3-butyl-2-heptene, 4-propyl-2-octene, 5-ethyl-2-nonene, and 6-methyl-2-decene, or alternatively, the sixth olefin composition (or the $C_{16-}$ olefin stream produced by any of the processes disclosed herein) can comprise any combination of 3-butyl-2-heptene, 4-propyl-2-octene, 5-ethyl-2-nonene, and 6-methyl-2-decene. An analogous sixth $C_{11}$ alkane composition (or $C_{16-}$ paraffins produced by any of the processes disclosed herein) can be formed via hydrogenation of the sixth olefin composition (or the $C_{16-}$ olefin stream), and the sixth alkane composition (or the $C_{16-}$ paraffins) can comprise 5-ethylnonane, 4-propyloctane, and 5-methyldecane, or alternatively, the sixth alkane composition (or the $C_{16-}$ paraffins) can comprise any combination of 5-ethylnonane, 4-propyloctane, and 5-methyldecane. The metathesis reaction scheme for the reaction of $C_{10}$ olefins with propylene to form the sixth $C_{11}$ olefin composition (or the $C_{16-}$ olefin stream) and the sixth $C_{11}$ alkane composition (or the $C_{16-}$ paraffins) is illustrated in FIG. 6.

Figure 7:
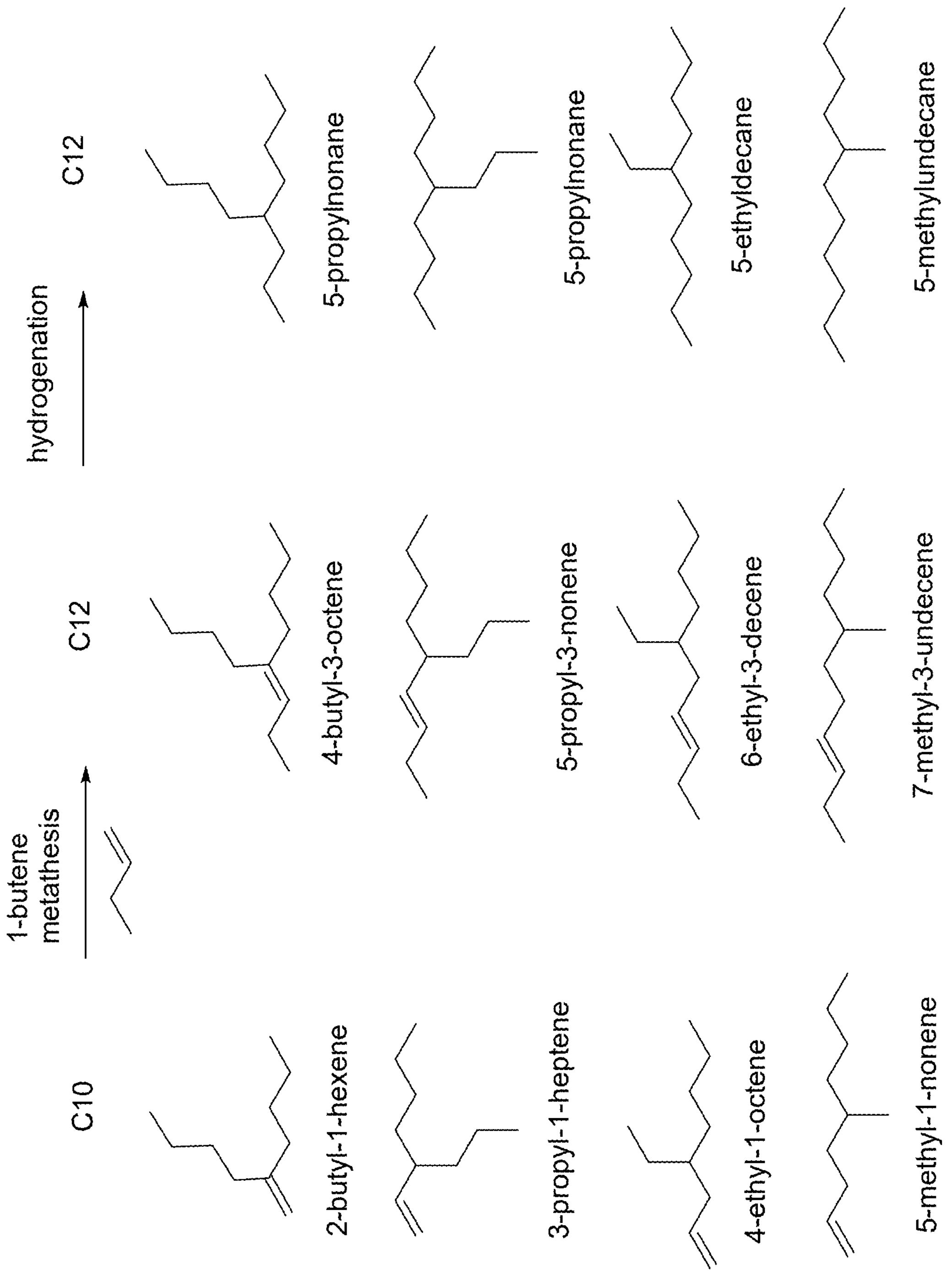
FIG. 7 is a metathesis reaction scheme for the reaction of $C_{10}$ olefins with 1-butene to form $C_{12}$ olefins and subsequent hydrogenation to from $C_{12}$ alkanes.

A seventh $C_{12}$ olefin composition can be derived from 1-butene metathesis with mixed decenes (e.g., 2-butyl-1-hexene, 3-propyl-1-heptene, 4-ethyl-1-octene, and 5-methyl-1-nonene), and the seventh olefin composition (or a $C_{16-}$ olefin stream produced by any of the processes disclosed herein) can comprise 4-butyl-3-octene, 5-propyl-3-nonene, 6-ethyl-3-decene, and/or 7-methyl-3-undecene. Thus, the seventh olefin composition (or the $C_{16-}$ olefin stream produced by any of the processes disclosed herein) can comprise 4-butyl-3-octene, 5-propyl-3-nonene, 6-ethyl-3-decene, and 7-methyl-3-undecene, or alternatively, the seventh olefin composition (or the $C_{16-}$ olefin stream produced by any of the processes disclosed herein) can comprise any combination of 4-butyl-3-octene, 5-propyl-3-nonene, 6-ethyl-3-decene, and 7-methyl-3-undecene. An analogous seventh $C_{12}$ alkane composition (or $C_{16-}$ paraffins produced by any of the processes disclosed herein) can be formed via hydrogenation of the seventh olefin composition (or the $C_{16-}$ olefin stream), and the seventh alkane composition (or the $C_{16-}$ paraffins) can comprise 5-propylnonane, 5-ethyldecane, and 5-methylundecane, or alternatively, the seventh alkane composition (or the $C_{16-}$ paraffins) can comprise any combination of 5-propylnonane, 5-ethyldecane, and 5-methylundecane. The metathesis reaction scheme for the reaction of $C_{10}$ olefins with 1-butene to form the seventh $C_{12}$ olefin composition (or the $C_{16-}$ olefin stream) and the seventh $C_{12}$ alkane composition (or the $C_{16-}$ paraffins) is illustrated in FIG. 7.

Figure 8:
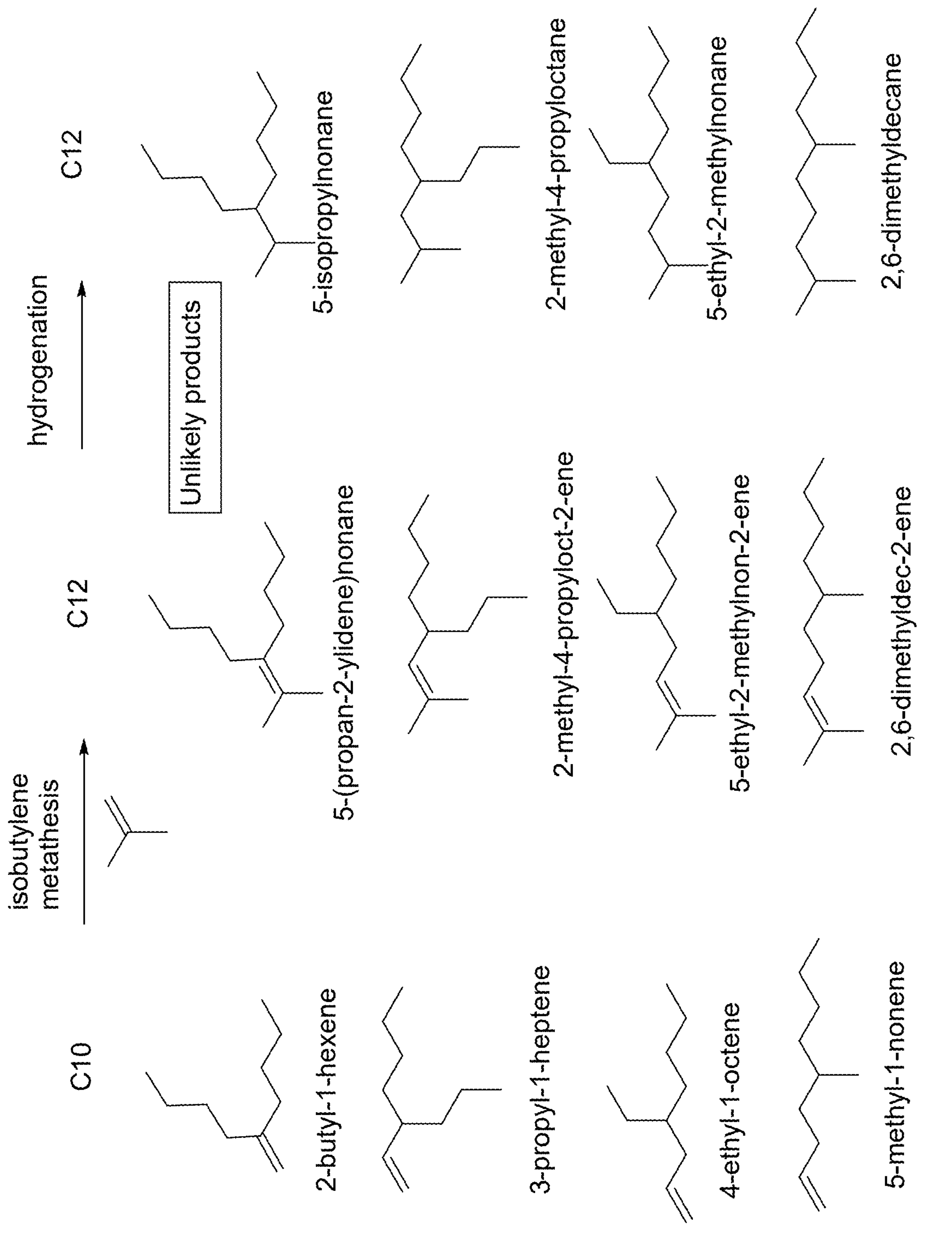
FIG. 8 is a metathesis reaction scheme for the reaction of $C_{10}$ olefins with isobutylene to form $C_{12}$ olefins and subsequent hydrogenation to from $C_{12}$ alkanes.

An eighth $C_{12}$ olefin composition can be derived from isobutylene metathesis with mixed decenes (e.g., 2-butyl-1-hexene, 3-propyl-1-heptene, 4-ethyl-1-octene, and 5-methyl-1-nonene), and the eighth olefin composition (or a $C_{16-}$ olefin stream produced by any of the processes disclosed herein) can comprise 2-methyl-4-propyloct-2-ene, 5-ethyl-2-methylnon-2-ene, and/or 2,6-dimethyldec-2-ene. Thus, the eighth olefin composition (or the $C_{16-}$ olefin stream produced by any of the processes disclosed herein) can comprise 2-methyl-4-propyloct-2-ene, 5-ethyl-2-methylnon-2-ene, and 2,6-dimethyldec-2-ene, or alternatively, the eighth olefin composition (or the $C_{16-}$ olefin stream produced by any of the processes disclosed herein) can comprise any combination of 2-methyl-4-propyloct-2-ene, 5-ethyl-2-methylnon-2-ene, and 2,6-dimethyldec-2-ene. An analogous eighth $C_{12}$ alkane composition (or $C_{16-}$ paraffins produced by any of the processes disclosed herein) can be formed via hydrogenation of the eighth olefin composition (or the $C_{16-}$ olefin stream), and the eighth alkane composition (or the $C_{16-}$ paraffins) can comprise 2-methyl-4-propyloctane, 5-ethyl-2-methylnonane, and 2,6-dimethyldecane, or alternatively, the eighth alkane composition (or the $C_{16-}$ paraffins) can comprise any combination of 2-methyl-4-propyloctane, 5-ethyl-2-methylnonane, and 2,6-dimethyldecane. The metathesis reaction scheme for the reaction of $C_{10}$ olefins with isobutylene to form the eighth $C_{12}$ olefin composition (or the $C_{16-}$ olefin stream) and the eighth $C_{12}$ alkane composition (or the $C_{16-}$ paraffins) is illustrated in FIG. 8.

Figure 9:
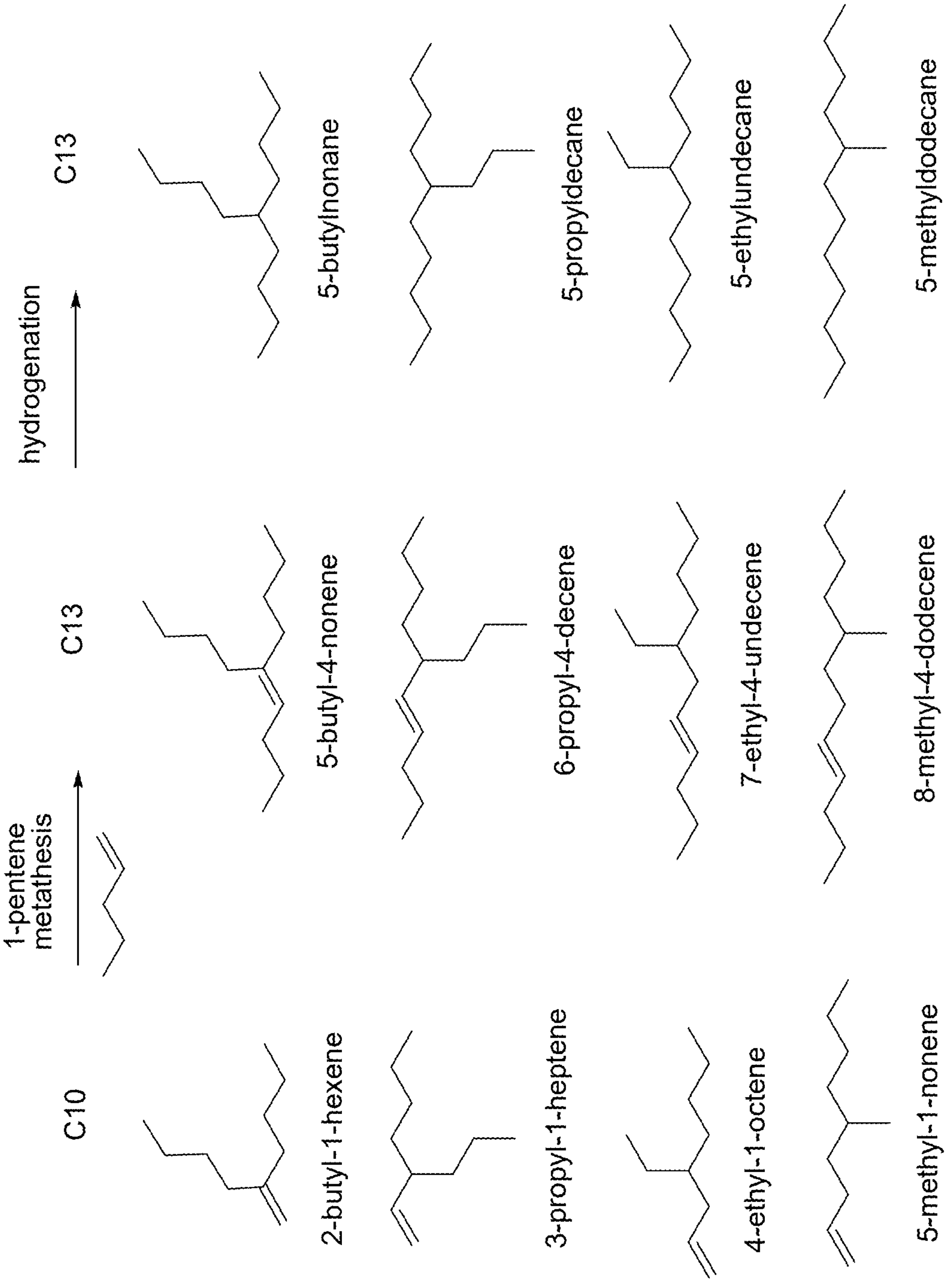
FIG. 9 is a metathesis reaction scheme for the reaction of $C_{10}$ olefins with 1-pentene to form $C_{13}$ olefins and subsequent hydrogenation to from $C_{13}$ alkanes.

A ninth $C_{13}$ olefin composition can be derived from 1-pentene metathesis with mixed decenes (e.g., 2-butyl-1-hexene, 3-propyl-1-heptene, 4-ethyl-1-octene, and 5-methyl-1-nonene), and the ninth olefin composition (or a $C_{16-}$ olefin stream produced by any of the processes disclosed herein) can comprise 5-butyl-4-nonene, 6-propyl-4-decene, 7-ethyl-4-undecene, and/or 8-methyl-4-dodecene. Thus, the ninth olefin composition (or the $C_{16-}$ olefin stream produced by any of the processes disclosed herein) can comprise 5-butyl-4-nonene, 6-propyl-4-decene, 7-ethyl-4-undecene, and 8-methyl-4-dodecene, or alternatively, the ninth olefin composition (or the $C_{16-}$ olefin stream produced by any of the processes disclosed herein) can comprise any combination of 5-butyl-4-nonene, 6-propyl-4-decene, 7-ethyl-4-undecene, and 8-methyl-4-dodecene. An analogous ninth $C_{13}$ alkane composition (or $C_{16-}$ paraffins produced by any of the processes disclosed herein) can be formed via hydrogenation of the ninth olefin composition (or the $C_{16-}$ olefin stream), and the ninth alkane composition (or the $C_{16-}$ paraffins) can comprise 5-butylnonane, 5-propyldecane, 5-ethylundecane, and 5-methyldodecane, or alternatively, the ninth alkane composition (or the $C_{16-}$ paraffins) can comprise any combination of 5-butylnonane, 5-propyldecane, 5-ethylundecane, and 5-methyldodecane. The metathesis reaction scheme for the reaction of $C_{10}$ olefins with 1-pentene to form the ninth $C_{13}$ olefin composition (or the $C_{16-}$ olefin stream) and the ninth $C_{13}$ alkane composition (or the $C_{16-}$ paraffins) is illustrated in FIG. 9.

Figure 10:
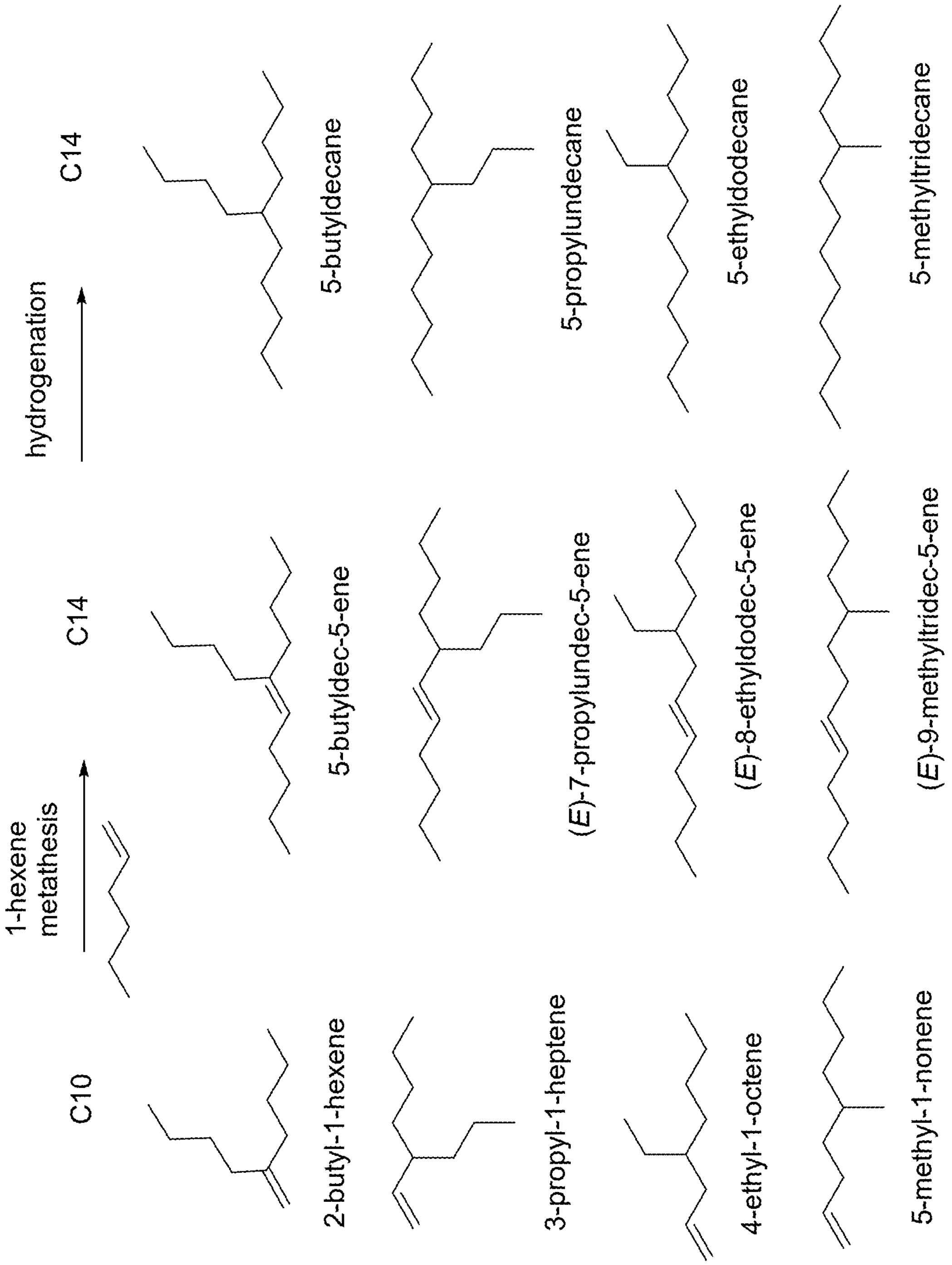
FIG. 10 is a metathesis reaction scheme for the reaction of $C_{10}$ olefins with 1-hexene to form $C_{14}$ olefins and subsequent hydrogenation to from $C_{14}$ alkanes.

A tenth $C_{14}$ olefin composition can be derived from 1-hexene metathesis with mixed decenes (e.g., 2-butyl-1-hexene, 3-propyl-1-heptene, 4-ethyl-1-octene, and 5-methyl-1-nonene), and the tenth olefin composition (or a $C_{16-}$ olefin stream produced by any of the processes disclosed herein) can comprise 5-butyldec-5-ene, 7-propylundec-5-ene, 8-ethyldodec-5-ene, and/or 9-methyltridec-5-ene. Thus, the tenth olefin composition (or the $C_{16-}$ olefin stream produced by any of the processes disclosed herein) can comprise 5-butyldec-5-ene, 7-propylundec-5-ene, 8-ethyldodec-5-ene, and 9-methyltridec-5-ene, or alternatively, the tenth olefin composition (or the $C_{16-}$ olefin stream produced by any of the processes disclosed herein) can comprise any combination of 5-butyldec-5-ene, 7-propylundec-5-ene, 8-ethyldodec-5-ene, and 9-methyltridec-5-ene. An analogous tenth $C_{14}$ alkane composition (or $C_{16-}$ paraffins produced by any of the processes disclosed herein) can be formed via hydrogenation of the tenth olefin composition (or the $C_{16-}$ olefin stream), and the tenth alkane composition (or the $C_{16-}$ paraffins) can comprise 5-butyldecane, 5-propylundecane, 5-ethyldodecane, and 5-methyltridecane, or alternatively, the tenth alkane composition (or the $C_{16-}$ paraffins) can comprise any combination of 5-butyldecane, 5-propylundecane, 5-ethyldodecane, and 5-methyltridecane. The metathesis reaction scheme for the reaction of $C_{10}$ olefins with 1-hexene to form the tenth $C_{14}$ olefin composition (or the $C_{16-}$ olefin stream) and the tenth $C_{14}$ alkane composition (or the $C_{16-}$ paraffins) is illustrated in FIG. 10.

Figure 11:
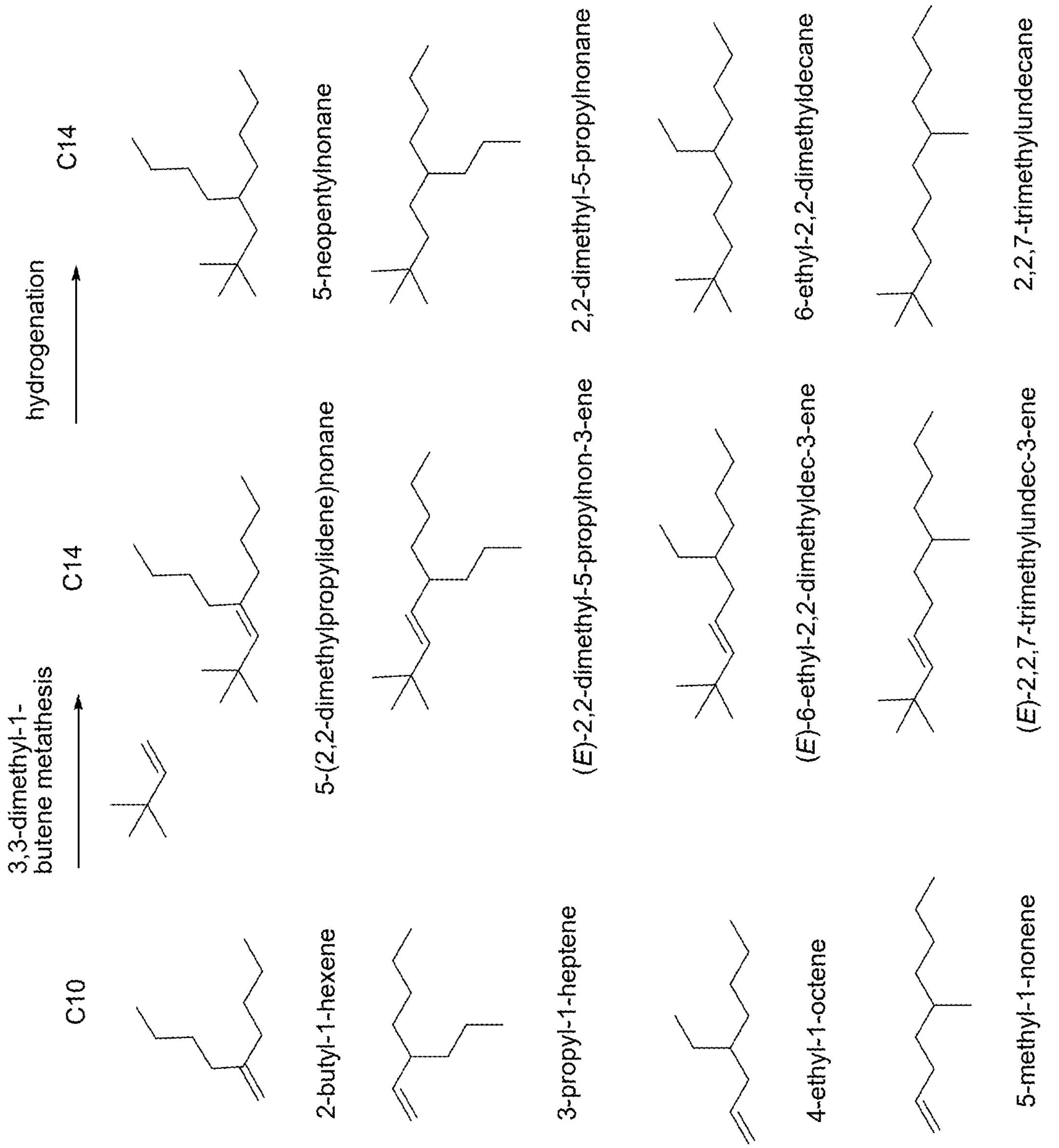
FIG. 11 is a metathesis reaction scheme for the reaction of $C_{10}$ olefins with 3,3-dimethyl-1-butene to form $C_{14}$ olefins and subsequent hydrogenation to from $C_{14}$ alkanes.

An eleventh $C_{14}$ olefin composition can be derived from 3,3-dimethyl-1-butene metathesis with mixed decenes (e.g., 2-butyl-1-hexene, 3-propyl-1-heptene, 4-ethyl-1-octene, and 5-methyl-1-nonene), and the eleventh olefin composition (or a $C_{16-}$ olefin stream produced by any of the processes disclosed herein) can comprise 5-(2,2-dimethylpropylidene)nonane, 2,2-dimethyl-5-propylnon-3-ene, 6-ethyl-2,2-dimethyldec-3-ene, and/or 2,2,7-trimethylundec-3-ene. Thus, the eleventh olefin composition (or the $C_{16-}$ olefin stream produced by any of the processes disclosed herein) can comprise 5-(2,2-dimethylpropylidene)nonane, 2,2-dimethyl-5-propylnon-3-ene, 6-ethyl-2,2-dimethyldec-3-ene, and 2,2,7-trimethylundec-3-ene, or alternatively, the eleventh olefin composition (or the $C_{16-}$ olefin stream produced by any of the processes disclosed herein) can comprise any combination of 5-(2,2-dimethylpropylidene)nonane, 2,2-dimethyl-5-propylnon-3-ene, 6-ethyl-2,2-dimethyldec-3-ene, and 2,2,7-trimethylundec-3-ene. An analogous eleventh $C_{14}$ alkane composition (or $C_{16-}$ paraffins produced by any of the processes disclosed herein) can be formed via hydrogenation of the eleventh olefin composition (or the $C_{16-}$ olefin stream), and the eleventh alkane composition (or the $C_{16-}$ paraffins) can comprise 5-neopentylnonane, 2,2-dimethyl-5-propylnonane, 6-ethyl-2,2-dimethyldecane, and 2,2,7-trimethylundecane, or alternatively, the eleventh alkane composition (or the $C_{16-}$ paraffins) can comprise any combination of 5-neopentylnonane, 2,2-dimethyl-5-propylnonane, 6-ethyl-2,2-dimethyldecane, and 2,2,7-trimethylundecane. The metathesis reaction scheme for the reaction of $C_{10}$ olefins with 3,3-dimethyl-1-butene to form the eleventh $C_{14}$ olefin composition (or the $C_{16-}$ olefin stream) and the eleventh $C_{14}$ alkane composition (or the $C_{16-}$ paraffins) is illustrated in FIG. 11.

Figure 12:
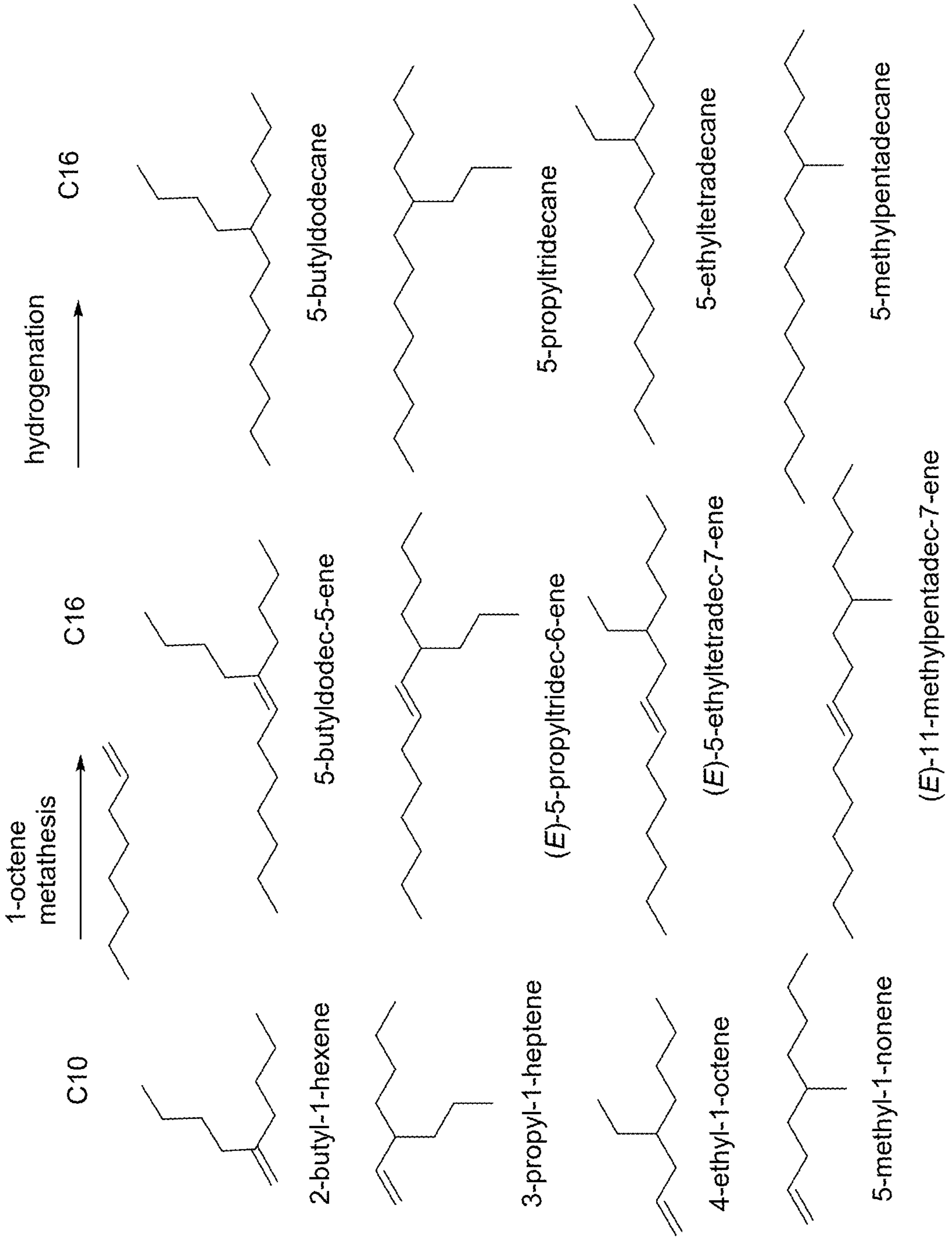
FIG. 12 is a metathesis reaction scheme for the reaction of $C_{10}$ olefins with 1-octene to form $C_{16}$ olefins and subsequent hydrogenation to from $C_{16}$ alkanes.

A twelfth $C_{16}$ olefin composition can be derived from 1-octene metathesis with mixed decenes (e.g., 2-butyl-1-hexene, 3-propyl-1-heptene, 4-ethyl-1-octene, and 5-methyl-1-nonene), and the twelfth olefin composition (or a $C_{16-}$ olefin stream produced by any of the processes disclosed herein) can comprise 5-butyldodec-5-ene, 5-propyltridec-6-ene, 5-ethyltetradec-7-ene, and 11-methylpentadec-7-ene. Thus, the twelfth olefin composition (or the $C_{16-}$ olefin stream produced by any of the processes disclosed herein) can comprise 5-butyldodec-5-ene, 5-propyltridec-6-ene, 5-ethyl-tetradec-7-ene, and 11-methylpentadec-7-ene, or alternatively, the twelfth olefin composition (or the $C_{16-}$ olefin stream produced by any of the processes disclosed herein) can comprise any combination of 5-butyldodec-5-ene, 5-propyltridec-6-ene, 5-ethyl-itetradec-7-ene, and 11-methylpentadec-7-ene. An analogous twelfth $C_{16}$ alkane composition (or $C_{16-}$ paraffins produced by any of the processes disclosed herein) can be formed via hydrogenation of the twelfth olefin composition (or the $C_{16-}$ olefin stream), and the twelfth alkane composition (or the $C_{16-}$ paraffins) can comprise 5-butyldodecane, 5-propyltridecane, 5-ethyltetradecane, and 5-methylpentadecane, or alternatively, the twelfth alkane composition (or the $C_{16-}$ paraffins) can comprise any combination of 5-butyldodecane, 5-propyltridecane, 5-ethyltetradecane, and 5-methylpentadecane. The metathesis reaction scheme for the reaction of $C_{10}$ olefins with 1-octene to form the twelfth $C_{16}$ olefin composition (or the $C_{16-}$ olefin stream) and the twelfth $C_{16}$ alkane composition (or the $C_{16-}$ paraffins) is illustrated in FIG. 12.

Aspects

The invention is described above with reference to numerous aspects and specific examples. Many variations will suggest themselves to those skilled in the art in light of the above detailed description. All such obvious variations are within the full intended scope of the appended claims. Other aspects of the invention can include, but are not limited to, the following (aspects are described as "comprising" but, alternatively, can "consist essentially of" or "consist of"):

Aspect 1. A process for making an aviation fuel, the process comprising (a) contacting an ethylene feed with a first catalyst system comprising a first oligomerization catalyst to form an oligomerization product comprising at least one $C_4$-$C_8$ alpha-olefin and a mixture of decenes, (b) separating the mixture of decenes from the oligomerization product, (c) forming a $C_{16-}$ olefin stream by (i) contacting the mixture of decenes with at least one $C_{6-}$ alpha-olefin in the presence of a second catalyst system comprising a second oligomerization catalyst, or (ii) contacting the mixture of decenes with at least one $C_{8-}$ alpha-olefin in the presence of a second catalyst system comprising a metathesis catalyst, (d) optionally, hydrogenating the $C_{16-}$ olefin stream in the presence of a first hydrogenation catalyst to provide $C_{16-}$ paraffins, and (e) optionally, using the $C_{16-}$ paraffins as a component to form an aviation fuel.

Aspect 2. A process for making an aviation fuel, the process comprising (a) contacting an ethylene feed with a first catalyst system comprising a first oligomerization catalyst to form an oligomerization product comprising at least one $C_4$-$C_8$ alpha-olefin and a mixture of decenes, (b) separating the mixture of decenes from the oligomerization product, (c) contacting the mixture of decenes with at least one $C_{6-}$ alpha-olefin in the presence of a second catalyst system comprising a second oligomerization catalyst to provide a $C_{16-}$ olefin stream, (d) optionally, hydrogenating the $C_{16-}$ olefin stream in the presence of a first hydrogenation catalyst to provide $C_{16-}$ paraffins, and (e) optionally, using the $C_{16-}$ paraffins as a component to form an aviation fuel.

Aspect 3. A process for making an aviation fuel, the process comprising (a) contacting an ethylene feed with a first catalyst system comprising a first oligomerization catalyst to form an oligomerization product comprising at least one $C_4$-$C_8$ alpha-olefin and a mixture of decenes, (b) separating the mixture of decenes from the oligomerization product, (c) contacting the mixture of decenes with at least one $C_{8-}$ alpha-olefin in the presence of a second catalyst system comprising a metathesis catalyst to provide a $C_{16-}$ olefin stream, (d) optionally, hydrogenating the $C_{16-}$ olefin stream in the presence of a first hydrogenation catalyst to provide $C_{16-}$ paraffins, and (e) optionally, using the $C_{16-}$ paraffins as a component to form an aviation fuel.

Aspect 4. A process for making an aviation fuel, the process comprising (a) contacting an ethylene feed with a first catalyst system comprising a first oligomerization catalyst to form an oligomerization product comprising at least one $C_4$-$C_8$ alpha-olefin and a mixture of decenes, (b) separating the mixture of decenes from the oligomerization product, (c) optionally, hydrogenating the mixture of decenes in the presence of a second hydrogenation catalyst to provide a mixture of decanes, and (d) optionally, using the mixture of decanes as a component to form an aviation fuel.

Aspect 5. A process for making an aviation fuel, the process comprising (a) contacting an ethylene feed with a first catalyst system comprising a first oligomerization catalyst to form an oligomerization product comprising at least one $C_4$-$C_6$ alpha-olefin or at least one $C_4$-$C_8$ alpha-olefin and a mixture of decenes, (b) contacting the oligomerization product with a second catalyst system comprising a second oligomerization catalyst or a metathesis catalyst to provide a $C_{16-}$ olefin stream, (c) optionally, hydrogenating the $C_{16-}$ olefin stream in the presence of a first hydrogenation catalyst to provide $C_{16-}$ paraffins, and (d) optionally, using the $C_{16-}$ paraffins as a component to form an aviation fuel.

Aspect 6. The process for making an aviation fuel according to any of Aspects 1-2, wherein the at least one $C_{6-}$ alpha-olefin comprises, consists essentially of, or is ethylene, propylene, 1-butene, 1-pentene, or 1-hexene, or a combination thereof; or alternatively, ethylene, 1-butene, 1-hexene, or a combination thereof.

Aspect 7. The process for making an aviation fuel according to any of Aspects 1 or 3, wherein the at least one $C_{8-}$ alpha-olefin comprises, consists essentially of, or is propylene, 1-butene, isobutylene, 1-pentene, 1-hexene, 3,3-dimethyl-1-butene, 1-octene, or a combination thereof; or alternatively, propylene, 1-butene, 1-hexene, 1-octene, or a combination thereof.

Aspect 8. The process for making an aviation fuel according to Aspect 4, wherein using the mixture of decanes as a component to form the aviation fuel comprises blending the mixture of decanes with $C_{16-}$ paraffins and/or cycloparaffins to provide the aviation fuel.

Aspect 9. The process for making an aviation fuel according to any preceding Aspect, wherein the at least one $C_4$-$C_8$ alpha-olefin comprises 1-butene, 1-hexene, 1-octene, or any combination thereof, and/or the at least one $C_4$-$C_6$ alpha-olefin comprises 1-butene, 1-hexene, or a combination thereof.

Aspect 10. The process for making an aviation fuel according to Aspect 5, wherein the steps of contacting the ethylene feed with the first catalyst system and contacting the oligomerization product with the second catalyst system are carried out in the same reactor.

Aspect 11. The process for making an aviation fuel according to Aspect 5, wherein the steps of contacting the ethylene feed with the first catalyst system and contacting the oligomerization product with the second catalyst system are carried out in different reactors.

Aspect 12. The process for making an aviation fuel according to any of Aspects 1-3 and 5-11, wherein the $C_{16-}$ paraffins comprise $C_{16-}$ n-alkanes, $C_{16-}$ iso-alkanes, or mixtures thereof.

Aspect 13. The process for making an aviation fuel according to any of Aspects 1-3 and 5-11, wherein the $C_{16-}$ paraffins comprise $C_{12}$ to $C_{16}$ n-alkanes, $C_{12}$ to $C_{16}$ iso-alkanes, or mixtures thereof.

Aspect 14. The process for making an aviation fuel according to any preceding Aspect, wherein at least a portion of the ethylene feed is a bio-ethylene feed.

Aspect 15. The process for making an aviation fuel according to any preceding Aspect, wherein at least a portion of the ethylene feed is a bio-ethylene feed, and the process further comprises providing the bio-ethylene feed by {1}converting a starch-based feedstock, a sugar-based feedstock, or a cellulosic feedstock to a biomass ethanol, and {2}dehydrating the biomass ethanol to provide a bio-ethylene feed, and the aviation fuel is a sustainable aviation fuel.

Aspect 16. The process for making an aviation fuel according to Aspect 15, wherein the sustainable aviation fuel or the component thereof is not further purified.

Aspect 17. The process for making an aviation fuel according to Aspect 15, wherein the sustainable aviation fuel or the component thereof is further purified.

Aspect 18. The process for making an aviation fuel according to any of Aspects 15-17, wherein the sustainable aviation fuel or the component thereof is blended with a non-sustainable aviation fuel.

Aspect 19. The process for making an aviation fuel according to any of Aspects 15-18, wherein all of the bio-ethylene feed is derived from the dehydration of biomass ethanol.

Aspect 20. The process for making an aviation fuel according to any of Aspects 15-18, wherein a portion of the bio-ethylene feed is derived from the dehydration of biomass ethanol.

Aspect 21. The process for making an aviation fuel according to any of Aspects 15-20, wherein the sustainable aviation fuel is certified as compliant with the Carbon Offsetting and Reduction Scheme for International Aviation (CORSIA) sustainability criteria in accordance with the International Sustainability and Carbon Certification (ISCC) CORSIA certification system.

Aspect 22. The process for making an aviation fuel according to any of Aspects 15-21, wherein the sustainable aviation fuel is certified as a Lower Carbon Aviation Fuel (LCAF) in accordance with the International Sustainability and Carbon Certification (ISCC) LCAF certification system.

Aspect 23. The process for making an aviation fuel according to any of Aspects 21-22, wherein the certification is based upon the weight or fraction of the sustainable aviation fuel attributable to the biomass ethanol determined by mass balance and the free attribution method.

Aspect 24. The process for making an aviation fuel according to any preceding Aspect, wherein the oligomerization product comprises 1-butene, 1-hexene, 1-octene, or any combination thereof.

Aspect 25. The process for making an aviation fuel according to any preceding Aspect, wherein the oligomerization product further comprises octenes, dodecenes, tetradecenes, or any combination thereof.

Aspect 26. The process for making an aviation fuel according to any of Aspects 1-25, wherein the oligomerization product comprises at least 60 mol %; at least 65 mol %; at least 70 mol %; at least 75 mol %; at least 80 mol %; at least 85 mol %; at least 90 mol %; or at least 95 mol % 1-hexene.

Aspect 27. The process for making an aviation fuel according to any of Aspects 1-25, wherein the oligomerization product comprises at least 60 mol %; at least 65 mol %; at least 70 mol %; at least 75 mol %; at least 80 mol %; at least 85 mol %; at least 90 mol %; or at least 95 mol % 1-octene.

Aspect 28. The process for making an aviation fuel according to any of Aspects 1-25, wherein the oligomerization product comprises at least 60 mol %; at least 65 mol %; at least 70 mol %; at least 75 mol %; at least 80 mol %; at least 85 mol %; at least 90 mol %; or at least 95 mol % 1-hexene and 1-octene combined.

Aspect 29. The process for making an aviation fuel according to any of Aspects 1-25, wherein the oligomerization product comprises at least 70 wt. % hexene; at least 75 wt. % hexene; at least 80 wt. % hexene; at least 85 wt. % hexene; or at least 90 wt. % hexene, based upon the weight of the oligomerization product.

Aspect 30. The process for making an aviation fuel according to any of Aspects 1-25, wherein the oligomerization product comprises from 70 wt. % to 99.8 wt. % hexene; from 75 wt. % to 99.7 wt. % hexene; or alternatively, from 80 wt. % to 99.6 wt. % hexane, based upon the weight of the oligomerization product.

Aspect 31. The process for making an aviation fuel according to any of Aspects 1-25, wherein the oligomerization product comprises at least 70 wt. % octene; at least 75 wt. % octene; at least 80 wt. % octene; at least 85 wt. % octene; or at least 90 wt. % octene, based upon the weight of the oligomerization product.

Aspect 32. The process for making an aviation fuel according to any of Aspects 1-25, wherein the oligomerization product comprises from 70 wt. % to 99.8 wt. % octene; from 75 wt. % to 99.7 wt. % octene; or from 80 wt. % to 99.6 wt. % octene, based upon the weight of the oligomerization product.

Aspect 33. The process for making an aviation fuel according to any of Aspects 1-32, wherein the oligomerization product comprises the mixture of decenes in a concentration of at least 0.5 mol %; at least 1 mol %; at least 2 mol %; at least 3 mol %; at least 4 mol %; at least 5 mol %; at least 6 mol %; at least 8 mol %; at least 10 mol %; at least 12 mol %; or at least 15 mol %.

Aspect 34. The process for making an aviation fuel according to any of Aspects 1-33, wherein contacting the bio-ethylene feed with the first catalyst system is carried out under conditions in which at least 0.2 wt. %, at least 1 wt. %, at least 2 wt. %, at least 5 wt. %, at least 7 wt. %, at least 10 wt. %, at least 12 wt. %, or at least 15 wt. % of the oligomerization product comprises the mixture of decenes.

Aspect 35. The process for making an aviation fuel according to any of Aspects 1-34, wherein the oligomerization product comprises the mixture of decenes in a concentration of less than 40 mol %; less than 35 mol %; less than 30 mol %; less than 25 mol %; less than 20 mol %; less than 15 mol %; less than 10 mol %; or less than 5 mol %.

Aspect 36. The process for making an aviation fuel according to any of Aspects 1-35, wherein contacting the bio-ethylene feed with the first catalyst system is carried out under conditions in which less than 5 wt. %, less than 7 wt. %, less than 10 wt. %, less than 12 wt. %, less than 15 wt. %, less than 18 wt. %, or less than 20 wt. % of the oligomerization product comprises the mixture of decenes.

Aspect 37. The process for making an aviation fuel according to any of Aspects 1-36, wherein the mixture of decenes comprises 2-butyl-1-hexene, 3-propyl-1-heptene, 4-ethyl-1-octene, 5-methyl-1-nonene, 4-decene, and 5-decene, or wherein the mixture of decenes comprises 2-butyl-1-hexene, 3-propyl-1-heptene, 4-ethyl-1-octene, and 5-methyl-1-nonene.

Aspect 38. The process for making an aviation fuel according to any of Aspects 1-37, wherein the mixture of decenes comprises at least 76 mol %, at least 78 mol %, at least 80 mol %, or at least 82 mol % $C_{10}$ monoolefins.

Aspect 39. The process for making an aviation fuel according to any of Aspects 1-38, wherein the mixture of decenes comprises from 76 mol % to 95 mol % $C_{10}$ monoolefins; from 78 mol % to 90 mol % $C_{10}$ monoolefins; from 80 mol % to 88 mol % $C_{10}$ monoolefins; or from 82 mol % to 86 mol % $C_{10}$ monoolefins.

Aspect 40. The process for making an aviation fuel according to any of Aspects 1-39, wherein the oligomerization product further comprises $C_{9-}$ monoolefins, $C_{11+}$ monoolefins, or combinations thereof.

Aspect 41. The process for making an aviation fuel according to any of Aspects 38-40, wherein the $C_{10}$ monoolefins comprise (a) at least 3 mol %, at least 4 mol %, at least 5 mol %, at least 6 mol %, at least 7 mol %, or at least 8 mol % 2-butyl-1-hexene; (b) at least 8 mol %, at least 9 mol %, at least 10 mol %, at least 11 mol %, at least 12 mol %, or at least 13 mol % 3-propyl-1-heptene; (c) at least 6 mol %, at least 7 mol %, at least 8 mol %, at least 9 mol %, at least 10 mol %, or at least 11 mol % 4-ethyl-1-octene; and (d) at least 20 mol %, at least 22 mol %, at least 24 mol %, at least 26 mol %, at least 28 mol %, or at least 30 mol % 5-methyl-1-nonene.

Aspect 42. The process for making an aviation fuel according to any of Aspects 38-41, wherein the $C_{10}$ monoolefins comprise from 3 mol % to 20 mol %, from 4 mol % to 18 mol %, from 5 mol % to 17 mol %, from 6 mol % to 16 mol %, or from 7 mol % to 15 mol % 2-butyl-1-hexene.

Aspect 43. The process for making an aviation fuel according to any of Aspects 38-42, wherein the $C_{10}$ monoolefins comprise from 10 mol % to 32 mol %, from 11 mol % to 30 mol %, from 12 mol % to 28 mol %, from 13 mol % to 26 mol %, or from 14 mol % to 24 mol % 3-propyl-1-heptene.

Aspect 44. The process for making an aviation fuel according to any of Aspects 38-43, wherein the $C_{10}$ monoolefins comprise from 7 mol % to 25 mol %, from 8 mol % to 24 mol %, from 9 mol % to 23 mol %, from 10 mol % to 22 mol %, or from 11 mol % to 21 mol % 4-ethyl-1-octene.

Aspect 45. The process for making an aviation fuel according to any of Aspects 38-44, wherein the $C_{10}$ monoolefins comprise from 24 mol % to 52 mol %, from 26 mol % to 50 mol %, from 28 mol % to 48 mol %, from 30 mol % to 46 mol %, or from 32 mol % to 44 mol % 5-methyl-1-nonene.

Aspect 46. The process for making an aviation fuel according to any of Aspects 38-45, wherein the $C_{10}$ monoolefins have any of the following features (a) a molar ratio of 2-butyl-1-hexene to 5-methyl-1-nonene of at least 2:1, at least 2.4:1, at least 2.6:1, or at least 2.8:1; (b) a molar ratio of 3-propyl-1-heptene to 5-methyl-1-nonene of at least 1.2:1, at least 1.4:1, at least 1.6:1, or at least 1.8:1; (c) a molar ratio of 4-ethyl-1-octene to 5-methyl-1-nonene of at least 1.6:1, at least 1.7:1, at least 1.9:1, or at least 2.1:1; or (d) any combination thereof.

Aspect 47. The process for making an aviation fuel according to any of Aspects 1-46, wherein the oligomerization product comprises at least 1 mol %, at least 2 mol %, at least 3 mol %, or at least 4 mol % $C_{14}$ monoolefins.

Aspect 48. The process for making an aviation fuel according to any of Aspects 1-46, wherein the oligomerization product comprises from 1 mol % to 12 mol % $C_{14}$ monoolefins; from 2 mol % to 10 mol % $C_{14}$ monoolefins; from 3 mol % to 8 mol % $C_{14}$ monoolefins; or from 4 mol % to 7 mol % $C_{14}$ monoolefins.

Aspect 49. The process for making an aviation fuel according to any of the preceding Aspects, wherein the oligomerization product comprises (a) from 0.1 mol % to 5 mol %, from 0.25 mol % to 4 mol %, or from 0.5 mol % to 3 mol % $C_8$ monoolefins, wherein the $C_8$ monoolefins comprise at least 95 mol % 1-octene; (b) 0.1 mol % to 5 mol %, from 0.25 mol % to 4 mol %, or from 0.5 mol % to 3 mol % $C_{12}$ monoolefins, wherein the $C_{12}$ monoolefins comprise from 54 mol % to 74 mol % 1-dodecene; (c) from 0.05 mol % to 2 mol %, from 0.04 mol % to 1.5 mol %, from 0.06 mol % to 1.25 mol %, from 0.08 mol % to 1 mol %, or from 0.1 mol % to 0.75 mol % $C_{16}$ monoolefins and/or $C_{15}$ monoolefins; or (d) any combination thereof.

Aspect 50. The process for making an aviation fuel according to any of the preceding Aspects, wherein the mixture of decenes comprises at least 95 mol % $C_{10}$ monoolefins, and $C_{10}$ monoolefins comprise (a) at least 3 mol % 2-butyl-1-hexene; (b) at least 10 mol % 3-propyl-1-heptene; (c) at least 7 mol % 4-ethyl-1-octene; and (d) at least 24 mol % 5-methyl-1-nonene.

Aspect 51. The process for making an aviation fuel according to Aspect 50, wherein the mixture of decenes comprise linear $C_{10}$ monoolefins comprising or consisting essentially of 1-decene, 4-decene, 5-decene, or combinations thereof.

Aspect 52. The process for making an aviation fuel according to any preceding Aspect, wherein the $C_{16-}$ olefin stream comprises 2,2-dimethyl-4-butyl-3-octene, 2,2-dimethyl-5-propyl-3-nonene, 2,2-dimethyl-6-ethyl-3-decene, and 2,2,7-trimethyl-3-undecene.

Aspect 53. The process for making an aviation fuel according to any of Aspects 1-51, wherein the $C_{16-}$ olefin stream comprises any one or any combination of 2,2-dimethyl-4-butyl-3-octene, 2,2-dimethyl-5-propyl-3-nonene, 2,2-dimethyl-6-ethyl-3-decene, and 2,2,7-trimethyl-3-undecene.

Aspect 54. The process for making an aviation fuel according to any of Aspects 1-51, wherein the $C_{16-}$ paraffins comprise 5-(2,2-dimethylpropyl)nonane, 2,2-dimethyl-5-propylnonane, 2,2-dimethyl-6-ethyl-decane, and 2,2,7-trimethylundecane.

Aspect 55. The process for making an aviation fuel according to any of Aspects 1-51, wherein the $C_{16-}$ paraffins comprise any one or any combination of 5-(2,2-dimethylpropyl)nonane, 2,2-dimethyl-5-propylnonane, 2,2-dimethyl-6-ethyl-decane, and 2,2,7-trimethylundecane.

Aspect 56. The process for making an aviation fuel according to any of Aspects 1-51, wherein the $C_{16-}$ olefin stream comprises 2-methyl-4-butyl-3-octene, 2-methyl-5-propylnon-3-ene, 6-ethyl-2-methyldec-3-ene, and 2,7-dimethylundec-3-ene.

Aspect 57. The process for making an aviation fuel according to any of Aspects 1-51, wherein the $C_{16-}$ olefin stream comprises any one or any combination of 2-methyl-4-butyl-3-octene, 2-methyl-5-propylnon-3-ene, 6-ethyl-2-methyldec-3-ene, and 2,7-dimethylundec-3-ene.

Aspect 58. The process for making an aviation fuel according to any of Aspects 1-51, wherein the $C_{16-}$ paraffins comprise 5-isobutylnonane, 2-methyl-5-propylnonane, 6-ethyl-2-methyldecane, and 2,7-dimethylundecane.

Aspect 59. The process for making an aviation fuel according to any of Aspects 1-51, wherein the $C_{16-}$ paraffins comprise any one or any combination of 5-isobutylnonane, 2-methyl-5-propylnonane, 6-ethyl-2-methyldecane, and 2,7-dimethylundecane.

Aspect 60. The process for making an aviation fuel according to any of Aspects 1-51, wherein the $C_{16-}$ olefin stream comprises 5-butyl-3-methylnon-4-ene, 3-methyl-6-propyldec-4-ene, 7-ethyl-3-methylundec-4-ene, and 3,8-dimethyldodec-4-ene.

Aspect 61. The process for making an aviation fuel according to any of Aspects 1-51, wherein the $C_{16-}$ olefin stream comprises any one or any combination of 5-butyl-3-methylnon-4-ene, 3-methyl-6-propyldec-4-ene, 7-ethyl-3-methylundec-4-ene, and 3,8-dimethyldodec-4-ene.

Aspect 62. The process for making an aviation fuel according to any of Aspects 1-51, wherein the $C_{16-}$ paraffins comprise 5-butyl-3-methylnonane, 3-methyl-6-propyldecane, 7-ethyl-3-methylundecane, and 3,8-dimethyldodecane.

Aspect 63. The process for making an aviation fuel according to any of Aspects 1-51, wherein the $C_{16-}$ paraffins comprise any one or any combination of 5-butyl-3-methylnonane, 3-methyl-6-propyldecane, 7-ethyl-3-methylundecane, and 3,8-dimethyldodecane.

Aspect 64. The process for making an aviation fuel according to any of Aspects 1-51, wherein the $C_{16-}$ olefin stream comprises 6-butyl-4-methyldec-5-ene, 4-methyl-7-propylundec-5-ene, 8-ethyl-4-methyldodec-5-ene, and 4,9-dimethyltridec-5-ene.

Aspect 65. The process for making an aviation fuel according to any of Aspects 1-51, wherein the $C_{16-}$ olefin stream comprises any one or any combination of 6-butyl-4-methyldec-5-ene, 4-methyl-7-propylundec-5-ene, 8-ethyl-4-methyldodec-5-ene, and 4,9-dimethyltridec-5-ene.

Aspect 66. The process for making an aviation fuel according to any of Aspects 1-51, wherein the $C_{16-}$ paraffins comprise 6-butyl-4-methyldecane, 4-methyl-7-propylundecane, 8-ethyl-4-methyldodecane, and 4,9-dimethyltridecane.

Aspect 67. The process for making an aviation fuel according to any of Aspects 1-51, wherein the $C_{16-}$ paraffins comprise any one or any combination of 6-butyl-4-methyldecane, 4-methyl-7-propylundecane, 8-ethyl-4-methyldodecane, and 4,9-dimethyltridecane.

Aspect 68. The process for making an aviation fuel according to any of Aspects 1-51, wherein the $C_{16-}$ olefin stream comprises 5-butyl-7-methylundec-5-ene, 5-methyl-8-propyldodec-6-ene, 9-ethyl-5-methyltridec-6-ene, and 5,10-dimethyltetradec-6-ene.

Aspect 69. The process for making an aviation fuel according to any of Aspects 1-51, wherein the $C_{16-}$ olefin stream comprises any one or any combination of 5-butyl-7-methylundec-5-ene, 5-methyl-8-propyldodec-6-ene, 9-ethyl-5-methyltridec-6-ene, and 5,10-dimethyltetradec-6-ene.

Aspect 70. The process for making an aviation fuel according to any of Aspects 1-51, wherein the $C_{16-}$ paraffins comprise 5-butyl-7-methylundecane, 5-methyl-8-propyldodecane, 5-ethyl-9-methyltridecane, and 5,10-dimethyltetradecane.

Aspect 71. The process for making an aviation fuel according to any of Aspects 1-51, wherein the $C_{16-}$ paraffins comprise any one or any combination of 5-butyl-7-methylundecane, 5-methyl-8-propyldodecane, 5-ethyl-9-methyltridecane, and 5,10-dimethyltetradecane.

Aspect 72. The process for making an aviation fuel according to any of Aspects 1-51, wherein the $C_{16-}$ olefin stream comprises 3-butyl-2-heptene, 4-propyl-2-octene, 5-ethyl-2-nonene, and 6-methyl-2-decene.

Aspect 73. The process for making an aviation fuel according to any of Aspects 1-51, wherein the $C_{16-}$ olefin stream comprises any one or any combination of 3-butyl-2-heptene, 4-propyl-2-octene, 5-ethyl-2-nonene, and 6-methyl-2-decene.

Aspect 74. The process for making an aviation fuel according to any of Aspects 1-51, wherein the $C_{16-}$ paraffins comprise 5-ethylnonane, 4-propyloctane, and 5-methyldecane.

Aspect 75. The process for making an aviation fuel according to any of Aspects 1-51, wherein the $C_{16-}$ paraffins comprise any one or any combination of 5-ethylnonane, 4-propyloctane, and 5-methyldecane.

Aspect 76. The process for making an aviation fuel according to any of Aspects 1-51, wherein the $C_{16-}$ olefin stream comprises 4-butyl-3-octene, 5-propyl-3-nonene, 6-ethyl-3-decene, and 7-methyl-3-undecene.

Aspect 77. The process for making an aviation fuel according to any of Aspects 1-51, wherein the $C_{16-}$ olefin stream comprises any one or any combination of 4-butyl-3-octene, 5-propyl-3-nonene, 6-ethyl-3-decene, and 7-methyl-3-undecene.

Aspect 78. The process for making an aviation fuel according to any of Aspects 1-51, wherein the $C_{16-}$ paraffins comprise 5-propylnonane, 5-ethyldecane, and 5-methylundecane.

Aspect 79. The process for making an aviation fuel according to any of Aspects 1-51, wherein the $C_{16-}$ paraffins comprise any one or any combination of 5-propylnonane, 5-ethyldecane, and 5-methylundecane.

Aspect 80. The process for making an aviation fuel according to any of Aspects 1-51, wherein the $C_{16-}$ olefin stream comprises 2-methyl-4-propyloct-2-ene, 5-ethyl-2-methylnon-2-ene, and 2,6-dimethyldec-2-ene.

Aspect 81. The process for making an aviation fuel according to any of Aspects 1-51, wherein the $C_{16-}$ olefin stream comprises any one or any combination of 2-methyl-4-propyloct-2-ene, 5-ethyl-2-methylnon-2-ene, and 2,6-dimethyldec-2-ene.

Aspect 82. The process for making an aviation fuel according to any of Aspects 1-51, wherein the $C_{16-}$ paraffins comprise 2-methyl-4-propyloctane, 5-ethyl-2-methylnonane, and 2,6-dimethyldecane.

Aspect 83. The process for making an aviation fuel according to any of Aspects 1-51, wherein the $C_{16-}$ paraffins comprise any one or any combination of 2-methyl-4-propyloctane, 5-ethyl-2-methylnonane, and 2,6-dimethyldecane.

Aspect 84. The process for making an aviation fuel according to any of Aspects 1-51, wherein the $C_{16-}$ olefin stream comprises 5-butyl-4-nonene, 6-propyl-4-decene, 7-ethyl-4-undecene, and 8-methyl-4-dodecene.

Aspect 85. The process for making an aviation fuel according to any of Aspects 1-51, wherein the $C_{16-}$ olefin stream comprises any one or any combination of 5-butyl-4-nonene, 6-propyl-4-decene, 7-ethyl-4-undecene, and 8-methyl-4-dodecene.

Aspect 86. The process for making an aviation fuel according to any of Aspects 1-51, wherein the $C_{16-}$ paraffins comprise 5-butylnonane, 5-propyldecane, 5-ethylundecane, and 5-methyldodecane.

Aspect 87. The process for making an aviation fuel according to any of Aspects 1-51, wherein the $C_{16-}$ paraffins comprise any one or any combination of 5-butylnonane, 5-propyldecane, 5-ethylundecane, and 5-methyldodecane.

Aspect 88. The process for making an aviation fuel according to any of Aspects 1-51, wherein the $C_{16-}$ olefin stream comprises 5-butyldec-5-ene, 7-propylundec-5-ene, 8-ethyldodec-5-ene, and 9-methyltridec-5-ene.

Aspect 89. The process for making an aviation fuel according to any of Aspects 1-51, wherein the $C_{16-}$ olefin stream comprises any one or any combination of 5-butyldec-5-ene, 7-propylundec-5-ene, 8-ethyldodec-5-ene, and 9-methyltridec-5-ene.

Aspect 90. The process for making an aviation fuel according to any of Aspects 1-51, wherein the $C_{16-}$ paraffins comprise 5-butyldecane, 5-propylundecane, 5-ethyldodecane, and 5-methyltridecane.

Aspect 91. The process for making an aviation fuel according to any of Aspects 1-51, wherein the $C_{16-}$ paraffins comprise any one or any combination of 5-butyldecane, 5-propylundecane, 5-ethyldodecane, and 5-methyltridecane.

Aspect 92. The process for making an aviation fuel according to any of Aspects 1-51, wherein the $C_{16-}$ olefin stream comprises 5-(2,2-dimethylpropylidene)nonane, 2,2-dimethyl-5-propylnon-3-ene, 6-ethyl-2,2-dimethyldec-3-ene, and 2,2,7-trimethylundec-3-ene.

Aspect 93. The process for making an aviation fuel according to any of Aspects 1-51, wherein the $C_{16-}$ olefin stream comprises any one or any combination of 5-(2,2-dimethylpropylidene)nonane, 2,2-dimethyl-5-propylnon-3-ene, 6-ethyl-2,2-dimethyldec-3-ene, and 2,2,7-trimethylundec-3-ene.

Aspect 94. The process for making an aviation fuel according to any of Aspects 1-51, wherein the $C_{16-}$ paraffins comprise 5-neopentylnonane, 2,2-dimethyl-5-propylnonane, 6-ethyl-2,2-dimethyldecane, and 2,2,7-trimethylundecane.

Aspect 95. The process for making an aviation fuel according to any of Aspects 1-51, wherein the $C_{16-}$ paraffins comprise any one or any combination of 5-neopentylnonane, 2,2-dimethyl-5-propylnonane, 6-ethyl-2,2-dimethyldecane, and 2,2,7-trimethylundecane.

Aspect 96. The process for making an aviation fuel according to any of Aspects 1-51, wherein the $C_{16-}$ olefin stream comprises 5-butyldodec-5-ene, 5-propyltridec-6-ene, 5-ethyltetradec-7-ene, and 11-methylpentadec-7-ene.

Aspect 97. The process for making an aviation fuel according to any of Aspects 1-51, wherein the $C_{16-}$ olefin stream comprises any one or any combination of 5-butyldodec-5-ene, 5-propyltridec-6-ene, 5-ethyltetradec-7-ene, and 11-methylpentadec-7-ene.

Aspect 98. The process for making an aviation fuel according to any of Aspects 1-51, wherein the $C_{16-}$ paraffins comprise 5-butyldodecane, 5-propyltridecane, 5-ethyltetradecane, and 5-methylpentadecane.

Aspect 99. The process for making an aviation fuel according to any of Aspects 1-51, wherein the $C_{16-}$ paraffins comprise any one or any combination of 5-butyldodecane, 5-propyltridecane, 5-ethyltetradecane, and 5-methylpentadecane.

Aspect 100. The process for making an aviation fuel according to any preceding Aspect, wherein independently: the first oligomerization catalyst comprises, consists essentially of, consists of, or is selected from any oligomerization catalyst; the second oligomerization catalyst comprises, consists essentially of, consists of, or is selected from any oligomerization catalyst promoting anti-Markovnikov selectivity; and the metathesis catalyst comprises, consists essentially of, consists of, or is selected from any metathesis catalyst.

Aspect 101. The process for making an aviation fuel according to any preceding Aspect, wherein the first catalyst system, the second catalyst system, or both catalyst systems independently comprise, consist essentially of, or consist of a chromium-based catalyst, a metallocene-based catalyst, a Ziegler-Natta based catalyst, a metal-oxide supported Group 6-10 transition metal-based catalyst, or a combination thereof.

Aspect 102. The process for making an aviation fuel according to any preceding Aspect, wherein the first catalyst system, the second catalyst system, or both catalyst systems independently comprise or consist essentially of (a) molybdenum oxide on alumina ($MoO_3/Al_2O_3$), tungsten oxide on silica ($WO_3/SiO_2$), tungsten oxide on silica-alumina ($WO_3/SiO_2/Al_2O_3$), rhenium oxide on alumina ($Re_2O_7/Al_2O_3$), cobalt oxide and molybdenum oxide on alumina ($CoO/MoO_3/Al_2O_3$), rhenium oxide on alumina activated with tetramethyl tin ($Re_2O_7/Al_2O_3/SnMe_4$), or any combination thereof; or (b) tungstated zirconium, molybdenum zirconium, nickel and/or cobalt doped tungstated zirconium, nickel and/or cobalt doped molybdenum zirconium catalysts, a Group 3 to Group 12 metal-treated zeolite, or combinations thereof.

Aspect 103. The process for making an aviation fuel according to any preceding Aspect, wherein the second oligomerization catalyst comprises, consists essentially of, consists of, or is selected from (a) $BF_3$ and a protic promoter or (b) a chemically-modified solid oxide which comprises a solid oxide treated with an electron-withdrawing anion.

Aspect 104. The process for making an aviation fuel according to any preceding Aspect, wherein the second oligomerization catalyst comprises, consists essentially of, consists of, or is selected from (a) $BF_3$ and (b) a protic promoter; and the protic promoter comprises, consists essentially of, or is selected from water, an alcohol, a carboxylic acid, or any combination thereof.

Aspect 105. The process for making an aviation fuel according to Aspect 104, wherein the alcohol comprises, consists essentially of, consists of, or is selected from a $C_1$ to $C_{20}$, alcohol; alternatively, a $C_1$ to $C_{15}$, alcohol; alternatively, a $C_1$ to $C_{10}$ alcohol; or alternatively, a $C_1$ to $C_6$ alcohol; a monool, a polyol, or any combination thereof; a monool, a diol, or any combination thereof; alternatively, a monool; alternatively, a polyol; or alternatively, a diol; a linear alcohol, a branched alcohol, or any combination thereof; alternatively, a linear alcohol; or alternatively, a branched alcohol; methanol, ethanol, a propanol, a butanol, a pentanol, a hexanol, or any combination thereof; alternatively, methanol; alternatively, ethanol; alternatively, 1-propanol; alternatively, 2-propanol; alternatively, 1-butanol; alternatively, 1-pentanol; or alternatively, 1-hexanol; or any combination thereof.

Aspect 106. The process for making an aviation fuel according Aspect 104, wherein the carboxylic acid comprises, consists essentially of, consists of, or is selected from a $C_2$ to $C_{20}$ carboxylic acid; alternatively, a $C_2$ to $C_{15}$ carboxylic acid; alternatively, a $C_3$ to $C_{10}$ carboxylic acid; or alternatively, a $C_3$ to $C_8$ carboxylic acid; a mono-carboxylic acid, a poly-carboxylic acid, or any combination thereof; alternatively, a monocarboxylic acid, a di-carboxylic acid, or any combination thereof; alternatively, a mono-carboxylic acid; alternatively, a poly-carboxylic acid; or alternatively, a di-carboxylic acid; a linear carboxylic acid, a branched carboxylic acid, or any combination thereof; alternatively, a linear carboxylic acid; or alternatively a branched carboxylic acid; acetic acid, propionic acid, a butyric acid, a hexanoic acid, a heptanoic acid, an octanoic acid, a nonanoic acid, a decanoic acid, a succinic acid, or any combination thereof; or any combination thereof.

Aspect 107. The process for making an aviation fuel according to any preceding Aspect, wherein: the second oligomerization catalyst comprises, consists essentially of, consists of, or is selected from a chemically-modified solid oxide which comprises a solid oxide treated with an electron-withdrawing anion; and the chemically-modified solid oxide is generated by treatment of a solid oxide with an acid of an electron-withdrawing anion or a salt of an electron-withdrawing anion.

Aspect 108. The process for making an aviation fuel according to Aspect 107, wherein following treatment of the solid oxide with the acid or the salt of an electron-withdrawing anion, the chemically-modified solid oxide is dried and calcined.

Aspect 109. The process for making an aviation fuel according to any of Aspects 107-108, wherein the solid oxide of the chemically-modified solid oxide comprises, consists essentially of, or is $Al_2O_3$, $B_2O_3$, BeO, $Bi_2O_3$, CdO, $Co_3O_4$, $Cr_2O_3$, CuO, $Fe_2O_3$, $Ga_2O_3$, $La_2O_3$, $Mn_2O_3$, $MoO_3$, $Na_2O$, NiO, $P_2O_5$, $Sb_2O_5$, $SiO_2$, $SnO_2$, SrO, $ThO_2$, $TiO_2$, $V_2O_5$, $WO_3$, $Y_2O_3$, ZnO, $ZrO_2$, $K_2O$, CaO, $La_2O_3$, $Ce_2O_3$, mixtures thereof, mixed oxides thereof (for example, silica-alumina), and any combination thereof.

Aspect 110. The process for making an aviation fuel according to any of Aspects 107-109, wherein the solid oxide of the chemically-modified solid oxide comprises, consists essentially of, or is silica, alumina, titania, zirconia, magnesia, boria, calcia, zinc oxide, silica-alumina, silica-coated alumina, silica-titania, silica-zirconia, silica-magnesia, alumina-titania, alumina-zirconia, zinc-aluminate, alumina-boria, silica-boria, aluminum phosphate, aluminophosphate, aluminophosphate-silica, magnesium aluminate, titania-zirconia, or any combination thereof.

Aspect 111. The process for making an aviation fuel according to any of Aspects 107-110, wherein the electron-withdrawing anion of the chemically-modified solid oxide comprises, consists essentially of, or is sulfate, bisulfate, fluorosulfate, phosphate, fluorophosphate, triflate, mesylate, tosylate, thiosulfate, $C_1$-$C_{10}$ alkyl sulfonate, $C_6$-$C_{14}$ aryl sulfonate, fluoride, chloride, or any combination thereof.

Aspect 112. The process for making an aviation fuel according to any of Aspects 107-111, wherein the chemically-modified solid oxide is generated by treatment of a solid oxide with sulfuric acid, sulfate ion, bisulfate ion, fluorosulfuric acid, fluorosulfate ion, phosphoric acid, phosphate ion, fluorophosphoric acid, monofluorophosphate ion, triflic (trifluoromethanesulfonic) acid, triflate trifluoromethanesulfonate) ion, methanesulfonic acid, mesylate (methanesulfonate) ion, toluenesulfonic acid, tosylate (toluenesulfonate) ion, thiosulfate ion, $C_1$-$C_{10}$ alkyl sulfonic acid, $C_1$-$C_{10}$ alkyl sulfonate ion, $C_6$-$C_{14}$ aryl sulfonic acid, $C_6$-$C_{14}$ aryl sulfonate ion, fluoride ion, chloride ion, or any combination thereof.

Aspect 113. The process for making an aviation fuel according to any of Aspects 107-112, wherein the chemically-modified solid oxide comprises a sulfur oxoacid anion-modified solid oxide, a phosphorus oxoacid anion-modified solid oxide, or a halide ion-modified solid oxide.

Aspect 114. The process for making an aviation fuel according to any of Aspects 107-113, wherein the chemically-modified solid oxide comprises a sulfated solid oxide, bisulfated (hydrogen sulfated) solid oxide, fluorosulfated solid oxide, phosphated solid oxide, fluorophosphated solid oxide, fluorided solid oxide, or chlorided solid oxide.

Aspect 115. The process for making an aviation fuel according to any of Aspects 107-114, wherein: the solid oxide of the chemically-modified solid oxide comprises, consists essentially of, or is silica, alumina, silica-alumina, silica-coated alumina, aluminum phosphate, aluminophosphate, heteropolytungstate, titania, zirconia, magnesia, boria, zinc oxide, a mixed oxide thereof, or any mixture thereof; and the electron-withdrawing anion of the chemically-modified solid oxide comprises, consists essentially of, or is sulfate, bisulfate, fluorosulfate, phosphate, fluorophosphates, fluoride, or chloride.

Aspect 116. The process for making an aviation fuel according to any of Aspects 107-115, wherein the chemically-modified solid oxide comprises or consists essentially of sulfated alumina, sulfated silica-alumina, or sulfated silica-coated alumina.

Aspect 117. The process for making an aviation fuel according to any of Aspects 107-116, wherein the chemically-modified solid oxide is metal-treated with a metal cation selected from a Group 1, 2, 12, or 13 metal.

Aspect 118. The process for making an aviation fuel according to any preceding Aspect, wherein the first catalyst system, the second catalyst system, or both catalyst systems independently comprise a metal alkyl compound selected from an organoaluminum compound, an organoaluminoxane, an organoboron compound, an organozinc compound, an organomagnesium compound, an organolithium compound, or any combination thereof.

Aspect 119. The process for making an aviation fuel according to any of preceding Aspect, wherein the first catalyst system, the second catalyst system, or both catalyst systems independently comprise a metal alkyl compound having the general formula (a) $M^3(X^{10})_n(X^{11})_{3-n}$, wherein $M^3$ is boron or aluminum and n is from 1 to 3 inclusive; (b) $M^4(X^{10})_n(X^{11})_{2-n}$, wherein $M^4$ is magnesium or zinc and n is from 1 to 2 inclusive; or (c) $M^5X^{10}$; wherein $M^5$ is Li; wherein $X^{10}$ is independently hydride or a $C_1$ to $C_{20}$ hydrocarbyl; and $X^{11}$ is independently a halide, a hydride, a $C_1$ to $C_{20}$ hydrocarbyl, or a $C_1$ to $C_{20}$ hydrocarbyloxide.

Aspect 120. The process for making an aviation fuel according to any preceding Aspect, wherein the first catalyst system, the second catalyst system, or both catalyst systems further comprise hydrogen.

Aspect 121. The process for making an aviation fuel according to any preceding Aspect, wherein the first catalyst system, the second catalyst system, or both catalyst systems further comprise hydrogen at partial pressure of from 2 psi to 100 psi; 5 psi to 75 psi; or 10 psi to 50 psi.

Aspect 122. The process for making an aviation fuel according to any of the preceding Aspects, wherein the first catalyst system or the second catalyst system independently comprises, consists essentially of, or is selected from a chromium-based catalyst.

Aspect 123. The process for making an aviation fuel according to Aspect 122, wherein the chromium-based catalyst comprises or consists essentially of (a) a chromium-containing compound, (b) a heteroatomic ligand, (c) a metal alkyl compound, and (d) optionally, a diluent.

Aspect 124. The process for making an aviation fuel according to Aspect 123, wherein the heteroatomic ligand is a separate component of the first catalyst system, the second catalyst system, or both catalyst systems, or wherein the heteroatomic ligand is complexed to the chromium-containing compound of the first catalyst system, the second catalyst system, or both catalyst systems.

Aspect 125. The process for making an aviation fuel according to any of the preceding Aspects, wherein the first catalyst system or the second catalyst system independently comprises, consists essentially of, or is selected from (a) a chromium-containing compound, a pyrrole compound, an organoaluminum compound, and optionally a halide containing compound; (b) a chromium-containing compound, a diphosphino aminyl compound, an organoaluminum compound; (c) a chromium-containing compound complexed to a diphosphino aminyl compound, and an organoaluminum compound; (d) a chromium-containing compound, an $N^2$-phosphinyl amidine compound, and an organoaluminum compound; (e) a chromium-containing compound complexed to an $N^2$-phosphinyl amidine compound, and an organoaluminum compound; (f) a chromium-containing compound, an $N^2$-phosphinyl formamidine compound, an organoaluminum compound; (g) a chromium-containing compound complexed to an $N^2$-phosphinyl formamidine compound, and an organoaluminum compound; or (h) any combinations thereof.

Aspect 126. The process for making an aviation fuel according to any of Aspects 123-125, wherein the chromium-containing compound is selected from chromium(II) nitrate, chromium(II) sulfate, chromium(II) fluoride, chromium(II) chloride, chromium(II) bromide, chromium(II) iodide, chromium(III) nitrate, chromium(III) sulfate, chromium(III) fluoride, chromium(III) chloride, chromium(III) bromide, or chromium(III) iodide.

Aspect 127. The process for making an aviation fuel according to any of Aspects 123-126, wherein the chromium-containing compound is selected from a chromium (II) carboxylate, a chromium(II) alkoxide, a chromium(II) aryloxide, a chromium(II) beta-dionate (i.e. beta-diketonate), a chromium(III) carboxylate, a chromium(III) alkoxide, a chromium(III) aryloxide, or a chromium(III) beta-dionate (i.e. beta-diketonate).

Aspect 128. The process for making an aviation fuel according to Aspect 127, wherein each carboxylate group of the chromium-containing compound independently can be a $C_2$ to $C_{24}$ carboxylate group, or alternatively a $C_4$ to $C_{19}$ carboxylate group, or alternatively, a $C_5$ to $C_{12}$ carboxylate group; each alkoxide group of the chromium-containing compound independently can be a $C_1$ to $C_{24}$ alkoxy group, alternatively, a $C_4$ to $C_{19}$ alkoxy group, or alternatively, a $C_5$ to $C_{12}$ alkoxy group; each aryloxide group of the chromium-containing compound independently can be a $C_6$ to $C_{24}$ aryloxy group, alternatively, a $C_6$ to $C_{19}$ aryloxy group, or alternatively, a $C_6$ to $C_{12}$ aryloxy group; and/or each beta-dionate group of the chromium-containing compound independently can be a $C_5$ to $C_{24}$ beta-dionate group, alternatively, a $C_5$ to $C_{19}$ beta-dionate group, or alternatively, a $C_5$ to $C_{12}$ beta-dionate group.

Aspect 129. The process for making an aviation fuel according to any of the preceding Aspects, wherein the first catalyst system or the second catalyst system independently comprises, consists essentially of, or is selected from a chromium carboxylate comprising or consisting essentially of an acetate, a propionate, a butyrate, a pentanoate, a hexanoate, a heptanoate, an octanoate, a nonanoate, a decanoate, an undecanoate, a dodecanoate, a tridecanoate, a tetradecanoate, a pentadecanoate, a hexadecanoate, a heptadecanoate, or an octadecanoate.

Aspect 130. The process for making an aviation fuel according to any of the preceding Aspects, wherein the first catalyst system or the second catalyst system independently comprises, consists essentially of, or is selected from a chromium carboxylate wherein each carboxylate group of the chromium carboxylate is independently selected from acetate, propionate, n-butyrate, isobutyrate, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, laurate (n-dodecanoate), or stearate (n-octadecanoate).

Aspect 131. The process for making an aviation fuel according to any of the preceding Aspects, wherein the first catalyst system or the second catalyst system independently comprises, consists essentially of, or is selected from a chromium carboxylate comprising, consisting essentially of, or selected from chromium(II) acetate, chromium(II) propionate, chromium(II) butyrate, chromium(II) isobutyrate, chromium(II) neopentanoate, chromium(II) oxalate, chromium(II) octanoate, chromium(II) 2-ethylhexanoate, chromium(II) laurate, or chromium(II) stearate, chromium(III) acetate, chromium(III) propionate, chromium(III) butyrate, chromium(III) isobutyrate, chromium(III) neopentanoate, chromium(III) oxalate, chromium(III) octanoate, chromium (III) 2-ethylhexanoate, chromium(III) 2,2,6,6,-tetramethylheptanedionate, chromium(III) naphthenate, chromium(III) laurate, or chromium(III) stearate.

Aspect 132. The process for making an aviation fuel according to any of Aspects 123-131, wherein the heteroatomic ligand can comprise, can consist essentially of, or can be, an amine compound, an amide compound, an imide compound, or combinations thereof.

Aspect 133. The process for making an aviation fuel according to any of Aspects 123-132, wherein the heteroatomic ligand can comprise, can consist essentially of, or can be (a) a $C_2$ to $C_{30}$ amine; alternatively, a $C_2$ to $C_{20}$ amine; alternatively, $C_2$ to $C_{15}$ amine; or alternatively, a $C_2$ to $C_{10}$ amine; (b) a $C_3$ to $C_{30}$ amide; alternatively, a $C_3$ to $C_{20}$ amide; alternatively, $C_3$ to $C_{15}$ amide; or alternatively, a $C_3$ to $C_{10}$ amide; or (c) a $C_4$ to $C_{30}$ imide; alternatively, a $C_4$ to $C_{20}$ imide; alternatively, $C_4$ to $C_{15}$ imide; or alternatively, a $C_4$ to $C_{10}$ imide.

Aspect 134. The process for making an aviation fuel according to any of Aspects 123-133 wherein the heteroatomic ligand can comprise, can consist essentially of, or can be, a pyrrole compound, a diphosphino aminyl compound, an $N^2$-phosphinyl amidine compound, an $N^2$-phosphinyl formamidine compound, or combinations thereof.

Aspect 135. The process for making an aviation fuel according to any of Aspects 123-134, wherein the heteroatomic ligand can comprise, can consist essentially of, or can be (a) any pyrrole compound that can form a chromium pyrrolide complex; (b) pyrrole ($C_5H_5N$), a derivative of pyrrole (e.g., indole), a substituted pyrroles, or a metal pyrrolide compound; or (c) pyrrole or any heteroleptic or homoleptic metal complex or salt containing a pyrrolide radical or ligand; or (d) a $C_4$ to $C_{30}$ pyrrole; alternatively, a $C_4$ to $C_{20}$ pyrrole; alternatively, $C_4$ to $C_{15}$ pyrrole; or alternatively, a $C_4$ to $C_{10}$ pyrrole.

Aspect 136. The process for making an aviation fuel according to any of Aspects 123-135, wherein the pyrrole compound can have Formula P1 or Formula I1:

P1

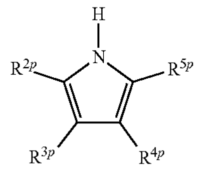

I1

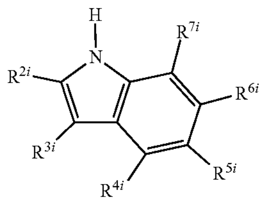

wherein: $R^{2p}$, $R^{3p}$, $R^{4p}$, and $R^{5p}$ of Formula P1 and $R^{2i}$, $R^{3i}$, $R^{4i}$, $R^{5i}$, $R^{6i}$, and $R^{7i}$ of Formula I1 can each independently be hydrogen, a $C_1$ to $C_{18}$ organyl group, a $C_1$ to $C_{18}$ hydrocarbyl group, or a $C_3$ to $C_{60}$ silyl group; alternatively, hydrogen, a $C_1$ to $C_{15}$ organyl group, a $C_1$ to $C_{15}$ hydrocarbyl group, or a $C_3$ to $C_{45}$ silyl group; alternatively, hydrogen, a $C_1$ to $C_{10}$ organyl group, a $C_1$ to $C_{10}$ hydrocarbyl group, or a $C_3$ to $C_{30}$ silyl group; alternatively, hydrogen, a $C_1$ to $C_5$ organyl group, a $C_1$ to $C_5$ hydrocarbyl group, or a $C_3$ to $C_{15}$ silyl group.

Aspect 137. The process for making an aviation fuel according to Aspect 136, wherein $R^{2p}$, $R^{3p}$, $R^{4p}$, and $R^{5p}$ of Formula P1 and $R^{2i}$, $R^{3i}$, $R^{4i}$, $R^{5i}$, $R^{6i}$, and $R^{7i}$ of Formula I1 can each independently be hydrogen or a $C_1$ to $C_{18}$ hydrocarbyl group; alternatively, hydrogen or a $C_1$ to $C_{15}$ hydrocarbyl group; alternatively, hydrogen or a $C_1$ to $C_{10}$ hydrocarbyl group; or alternatively, hydrogen or a $C_1$ to $C_5$ hydrocarbyl group.

Aspect 138. The process for making an aviation fuel according to any of Aspects 123-131 and 134-137, wherein the pyrrole compound can comprise, can consist essentially of, or can be, pyrrole, 2,5-dimethylpyrrole, 2-methyl-5-ethylpyrrole, 2-methyl-5-propylpyrrole, 2,5-diethylpyrrole, 3,4-dimethylpyrrole, 2,5-di-n-propylpyrrole, 2,5-di-n-butylpyrrole, 2,5-di-n-pentylpyrrole, 2,5-di-n-hexylpyrrole, 2,5-di-n-heptylpyrrole, 2,5-di-n-octylpyrrole, 2,5-dibenzylpyrrole, 2,4-dimethyl-3-ethylpyrrole, 2,3,5-triethylpyrrrole, 2,3,5-tri-n-butylpyrrrole, 2,3,5-tri-n-pentylpyrrrole, 2,3,5-tri-n-hexylpyrrrole, 2,3,5-tri-n-heptylpyrrrole, 2,3,5-tri-n-octylpyrrrole, 2,3,4,5-tetraethylpyrrole, 2,3,4,5-tetra-n-butylpyrrole, 2,3,4,5-tetra-n-hexylpyrrole, 2,5-bis(2',2',2'-trifluoroethyl)pyrrole, 2,5-bis(2'-methoxymethyl)pyrrole, 2-methyl-4-isopropylpyrrole, 2-ethyl-4-isopropylpyrrole, 2-methyl-4-sec-butylpyrrole, 2-ethyl-4-sec-butylpyrrole, 2-methyl-4-isobutylpyrrole, 2-ethyl-4-isobutylpyrrole, 2-methyl-4-t-butylpyrrole, 2-ethyl-4-t-butylpyrrole, 2-methyl-4-neopentylpyrrole, 2-ethyl-4-neopentylpyrrole, 3,4-diisopropylpyrrole, 3,4-di-sec-butylpyrrole, 3,4-di-isobutylpyrrole, 3,4-di-t-butylpyrrole, 3,4-di-neo-pentylpropylpyrrole, tetrahydroindole, dipyrrolylmethane, indole, 3,4-dichloropyrrole, 2,3,4,5-tetrachloropyrrole, pyrrole-2-carboxylic acid, 2-acetylpyrrole, pyrrole-2-carboxaldehyde, 3-acetyl-2,4-dimethylpyrrole, ethyl-2,4-dimethyl-5-(ethoxycarbonyl)-3-pyrrole-propionate, or ethyl-3,5-dimethyl-2-pyrrolecarboxylate.

Aspect 139. The process for making an aviation fuel according to any of Aspects 123-131 and 134-137, wherein the pyrrole compound can comprise, can consist essentially of, or can be (a) a metal pyrrolide, such as an alkyl metal pyrrolide; (b) a diorganoaluminum pyrrolide of any pyrrole provided herein; (c) diethylaluminum 2,5-dimethylpyrrolide, ethylaluminum di(2,5-dimethylpyrrolide), aluminum tri(2,5-dimethylpyrrolide); or combinations thereof.

Aspect 140. The process for making an aviation fuel according to any of Aspects 123-139, wherein the heteroatomic ligand can comprise, can consist essentially of, or can be, a diphosphino aminyl compound (i.e. a compound comprising a P—N—P (phosphorus-nitrogen-phosphorus) linkage).

Aspect 141. The process for making an aviation fuel according to any of Aspects 123-140, wherein the heteroatomic ligand can comprise, can consist essentially of, or can be a diphosphino aminyl moiety having Structure PNP2:

PNP2

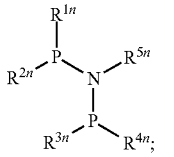

wherein the $R^{1n}$, $R^{2n}$, $R^{3n}$, $R^{4n}$, and/or $R^{5n}$, independently can be (a) a $C_1$ to $C_{30}$ organyl group; alternatively, a $C_1$ to $C_{20}$ organyl group; alternatively, a $C_1$ to $C_{15}$ organyl group; alternatively, a $C_1$ to $C_{10}$ organyl group; or alternatively, a $C_1$ to $C_5$ organyl group; (b) a $C_1$ to $C_{30}$ organyl group comprising inert functional groups; alternatively, a $C_1$ to $C_{20}$ organyl group comprising inert functional groups; alternatively, a $C_1$ to $C_{15}$ organyl group comprising inert functional groups; alternatively, a $C_1$ to $C_{10}$ organyl group comprising inert functional groups; or alternatively, a $C_1$ to $C_5$ organyl group comprising inert functional groups; (c) a $C_1$ to $C_{30}$ hydrocarbyl group; alternatively, a $C_1$ to $C_{20}$ hydrocarbyl group; alternatively, a $C_1$ to $C_{15}$ hydrocarbyl group; alternatively, a $C_1$ to $C_{10}$ hydrocarbyl group; or alternatively, a $C_1$ to $C_5$ hydrocarbyl group; (d) a $C_1$ to $C_{30}$ alkyl group; alternatively, a $C_1$ to $C_{20}$ alkyl group; alternatively, a $C_1$ to $C_{15}$ alkyl group; alternatively, a $C_1$ to $C_{10}$ alkyl group; or alternatively, a $C_1$ to $C_5$ alkyl group; (e) a $C_6$ to $C_{30}$ aromatic group; alternatively, a $C_6$ to $C_{20}$ aromatic group; alternatively, a $C_6$ to $C_{15}$ aromatic group; or alternatively, a $C_6$ to $C_{10}$ aromatic group; (f) a phenyl group or a $C_6$ to $C_{30}$ substituted phenyl group; alternatively, a phenyl group or a $C_6$ to $C_{20}$ substituted phenyl group; alternatively, a phenyl group or a $C_6$ to $C_{15}$ substituted phenyl group; alternatively, a phenyl group or a $C_6$ to $C_{10}$ substituted phenyl group; or alternatively, a phenyl group; or (g) a substituted or an unsubstituted $C_1$ to $C_{20}$ alkyl group, $C_5$ to $C_{20}$ cycloalkyl group, or $C_6$-$C_{20}$ aromatic group; wherein any substituents are selected independently from a $C_1$ to $C_{10}$ hydrocarbyl group.

Aspect 142. The process for making an aviation fuel according to Aspect 141, wherein $R^{1n}$ and $R^{2n}$, and/or $R^{3n}$ and $R^{4n}$ of the diphosphino aminyl moiety can be joined to form a ring containing a phosphorus atom of the diphosphino aminyl moiety.

Aspect 143. The process for making an aviation fuel according to any of Aspects 141-142, wherein $R^{1n}$ and $R^{5n}$, or $R^{4n}$ and $R^{5n}$ of the diphosphino aminyl moiety can be joined to form a ring containing a phosphorus atom and the nitrogen atom of the diphosphino aminyl moiety.

Aspect 144. The process for making an aviation fuel according to any of Aspects 123-142, wherein the heteroatomic ligand can be an $N^2$-phosphinyl formamidine compound having Structure NPF1, or an $N^2$-phosphinyl formamidine compound having Structure NPA1:

Structure NPF1

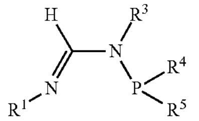

Structure NPA1

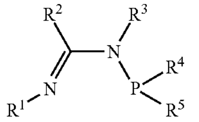

wherein $R^1$, $R^2$, $R^3$, $R^4$, and $R^5$ within Structure NPF1 and Structure NPFCr1 are independently (a)(i) a $C_1$ to $C_{30}$ organyl group, a $C_1$ to $C_{30}$ organyl group consisting essentially of inert functional groups, or a $C_1$ to $C_{30}$ hydrocarbyl group; (ii) a $C_1$ to $C_{20}$ organyl group, a $C_1$ to $C_{20}$ organyl group consisting essentially of inert functional groups, or a $C_1$ to $C_{20}$ hydrocarbyl group; (iii) a $C_1$ to $C_{15}$ organyl group, a $C_1$ to $C_{15}$ organyl group consisting essentially of inert functional groups, or a $C_1$ to $C_{15}$ hydrocarbyl group; (iv) a $C_1$ to $C_{10}$ organyl group, a $C_1$ to $C_{10}$ organyl group consisting essentially of inert functional groups, or a $C_1$ to $C_{10}$ hydrocarbyl group; or (v) a $C_1$ to $C_5$ organyl group, a $C_1$ to $C_5$ organyl group consisting essentially of inert functional groups, or a $C_1$ to $C_5$ hydrocarbyl group; (b) a $C_1$ to $C_{30}$ alkyl group; alternatively, a $C_1$ to $C_{20}$ alkyl group; alternatively, a $C_1$ to $C_{15}$ alkyl group; alternatively, a $C_1$ to $C_{10}$ alkyl group; or alternatively, a $C_1$ to $C_5$ alkyl group; (c) a $C_6$ to $C_{30}$ aromatic group; alternatively, a $C_6$ to $C_{20}$ aromatic group; alternatively, a $C_6$ to $C_{15}$ aromatic group; or alternatively, a $C_6$ to $C_{10}$ aromatic group; (d) a phenyl group or a $C_6$ to $C_{30}$ substituted phenyl group; alternatively, a phenyl group or a $C_6$ to $C_{20}$ substituted phenyl group; alternatively, a phenyl group or a $C_6$ to $C_{15}$ substituted phenyl group; or alternatively, a phenyl group or a $C_6$ to $C_{10}$ substituted phenyl group; or (e) a benzyl group or a $C_6$ to $C_{30}$ substituted benzyl group; alternatively, a benzyl group or a $C_6$ to $C_{20}$ substituted benzyl group; alternatively, a benzyl group or a $C_6$ to $C_{15}$ substituted benzyl group; or alternatively, a benzyl group or a $C_6$ to $C_{10}$ substituted benzyl group.

Aspect 145. The process for making an aviation fuel according to any of Aspects 123-144, wherein the chromium-containing compound complexed to an $N^2$-phosphinyl formamidine compound or the chromium-containing compound complexed to an $N^2$-phosphinyl amidine compound have the following structures:

Structure NPFCr1

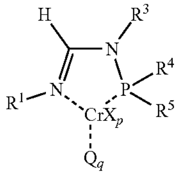

Structure NPACr1

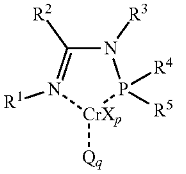

wherein X is an anionic ligand, and p is from 2 to 6, Q is a neutral ligand such as a nitrile ligand or an ether ligand, and q is from 0 to 6; and wherein $R^1$, $R^2$, $R^3$, $R^4$, and $R^5$ within Structure NPF1 and Structure NPFCr1 are independently (a)(i) a $C_1$ to $C_{30}$ organyl group, a $C_1$ to $C_{30}$ organyl group consisting essentially of inert functional groups, or a $C_1$ to $C_{30}$ hydrocarbyl group; (ii) a $C_1$ to $C_{20}$ organyl group, a $C_1$ to $C_{20}$ organyl group consisting essentially of inert functional groups, or a $C_1$ to $C_{20}$ hydrocarbyl group; (iii) a $C_1$ to $C_{15}$ organyl group, a $C_1$ to $C_{15}$ organyl group consisting essentially of inert functional groups, or a $C_1$ to $C_{15}$ hydrocarbyl group; (iv) a $C_1$ to $C_{10}$ organyl group, a $C_1$ to $C_{10}$ organyl group consisting essentially of inert functional groups, or a $C_1$ to $C_{10}$ hydrocarbyl group; or (v) a $C_1$ to $C_5$ organyl group, a $C_1$ to $C_5$ organyl group consisting essentially of inert functional groups, or a $C_1$ to $C_5$ hydrocarbyl group; (b) a $C_1$ to $C_{30}$ alkyl group; alternatively, a $C_1$ to $C_{20}$ alkyl group; alternatively, a $C_1$ to $C_{15}$ alkyl group; alternatively, a $C_1$ to $C_{10}$ alkyl group; or alternatively, a $C_1$ to $C_5$ alkyl group; (c) a $C_6$ to $C_{30}$ aromatic group; alternatively, a $C_6$ to $C_{20}$ aromatic group; alternatively, a $C_6$ to $C_{15}$ aromatic group; or alternatively, a $C_6$ to $C_{10}$ aromatic group; (d) a phenyl group or a $C_6$ to $C_{30}$ substituted phenyl group; alternatively, a phenyl group or a $C_6$ to $C_{20}$ substituted phenyl group; alternatively, a phenyl group or a $C_6$ to $C_{15}$ substituted phenyl group; or alternatively, a phenyl group or a $C_6$ to $C_{10}$ substituted phenyl group; or (e) a benzyl group or a $C_6$ to $C_{30}$ substituted benzyl group; alternatively, a benzyl group or a $C_6$ to $C_{20}$ substituted benzyl group; alternatively, a benzyl group or a $C_6$ to $C_{15}$ substituted benzyl group; or alternatively, a benzyl group or a $C_6$ to $C_{10}$ substituted benzyl group.

Aspect 146. The process for making an aviation fuel according to any of Aspects 144-145, wherein $R^1$ is a $C_1$ to $C_{15}$ alkyl group, a $C_4$ to $C_{20}$ cycloalkyl group, a $C_4$ to $C_{20}$ substituted cycloalkyl group, a $C_6$ to $C_{20}$ aryl group, or a $C_6$ to $C_{20}$ substituted aryl group; $R^2$ is a $C_1$ to $C_{30}$ organyl group consisting essentially of inert functional groups wherein the inert functional groups are selected from halo groups, nitro groups, hydrocarboxy groups, sulfidyl groups, hydrocarbyl groups, or combinations thereof; $R^3$ is hydrogen; and $R^4$ and $R^5$ are each independently a $C_1$ to $C_{30}$ organyl group consisting essentially of inert functional groups wherein the inert functional groups are selected from halo groups, nitro groups, hydrocarboxy groups, sulfidyl groups, hydrocarbyl groups, or combinations thereof.

Aspect 147. The process for making an aviation fuel according to any of Aspects 135-146, or any of the preceding Aspects, wherein any substituent of a substituted group is selected from (a) a halide, a hydrocarbyl group, or a hydrocarboxy group; alternatively, a halide or a hydrocarbyl group; or (b) a $C_1$ to $C_{10}$ hydrocarbyl group or a $C_1$ to $C_{10}$ hydrocarboxy group; alternatively, a halide or a $C_1$ to $C_{10}$ hydrocarbyl group; alternatively, a halide or a $C_1$ to $C_{10}$ hydrocarboxy group; alternatively, a $C_1$ to $C_{10}$ hydrocarbyl group or a $C_1$ to $C_{10}$ hydrocarboxy group; alternatively, a halide; alternatively, a $C_1$ to $C_{10}$ hydrocarbyl group; or alternatively, a $C_1$ to $C_{10}$ hydrocarboxy group.

Aspect 148. The process for making an aviation fuel according to any of the preceding Aspects, wherein the first catalyst system, the second catalyst system, or both catalyst systems independently comprise an organoaluminum compound.

Aspect 149. The process for making an aviation fuel according to Aspect 148, wherein the organoaluminum compound comprises, consists essentially of, or is selected from a triorganoaluminum compound, a diorganoaluminum halide, an organoaluminum dihalide, a diorganoaluminum alkoxide, an organoaluminum dialkoxide, an aluminoxane, or combinations thereof.

Aspect 150. The process for making an aviation fuel according to Aspect 148, wherein the organoaluminum compound has a general formula $Al(R^{10})_n(X^{11})_{3-n}$, wherein n is from 1 to 3 inclusive; each $R^{10}$ is independently a $C_1$ to $C_{20}$ hydrocarbyl; and $X^{11}$ is independently a halide, a hydride, a $C_1$ to $C_{20}$ hydrocarbyl, or a $C_1$ to $C_{20}$ hydrocarbyloxide.

Aspect 151. The process for making an aviation fuel according to Aspect 148, wherein the organoaluminum compound comprises, consists of, consists essentially of, or is selected from trimethylaluminum, triethylaluminum, tri-n-propylaluminum, tri-n-butylaluminum, triisobutylaluminum, tri-n-hexylaluminum, tri-n-octylaluminum, diisobutylaluminum hydride, diethylaluminum ethoxide, diethylaluminum chloride, or any combination thereof.

Aspect 152. The process for making an aviation fuel according to Aspect 148, wherein the organoaluminum compound comprises, consists of, consists essentially of, or is selected from an aluminoxane compound.

Aspect 153. The process for making an aviation fuel according to Aspect 148, wherein the organoaluminum compound comprises, consists of, consists essentially of, or is selected from at least one aluminoxane compound, and wherein the aluminoxane comprises a cyclic aluminoxane having the formula

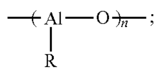

wherein R is a linear or branched alkyl having from 1 to 10 carbon atoms, and n is an integer from 3 to about 10; a linear aluminoxane having the formula

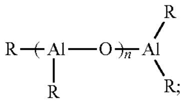

wherein R is a linear or branched alkyl having from 1 to 10 carbon atoms, and n is an integer from 1 to about 50; a cage aluminoxane having the formula $R^t_{5m+\alpha}R^b_{m-\alpha}Al_{4m}O_{3m}$, wherein m is 3 or 4 and $\alpha = n_{Al(3)} - n_{O(2)} + n_{O(4)}$; wherein $n_{Al(3)}$ is the number of three coordinate aluminum atoms, $n_{O(2)}$ is the number of two coordinate oxygen atoms, $n_{O(4)}$ is the number of 4 coordinate oxygen atoms, $R^t$ represents a terminal alkyl group, and $R^b$ represents a bridging alkyl group; wherein R is a linear or branched alkyl having from 1 to 10 carbon atoms; or any combination thereof.

Aspect 154. The process for making an aviation fuel according to Aspect 148, wherein the organoaluminum compound comprises, consists of, consists essentially of, or is selected from an aluminoxane having the formula $(R^C—Al—O)_t$ or $R^C(R^C—Al—O)_tAl(R^C)_2$, wherein $R^C$ is a linear or branched $C_1$-$C_6$ alkyl such as methyl, ethyl, propyl, butyl, pentyl, or hexyl wherein t is an integer from 1 to 50, inclusive, or t is an integer from 2 to 20.

Aspect 155. The process for making an aviation fuel according to Aspect 137, wherein the organoaluminum compound comprises, consists of, consists essentially of, or is selected from methylaluminoxane (MAO), ethylaluminoxane, modified methylaluminoxane (MMAO) such as an isobutyl-modified methyl alumoxane, n-propylaluminoxane, iso-propylaluminoxane, n-butylaluminoxane, t-butylaluminoxane, sec-butylaluminoxane, iso-butylaluminoxane, t-butyl aluminoxane, 1-pentylaluminoxane, 2-pentylaluminoxane, 3-pentylaluminoxane, iso-pentylaluminoxane, neopentylaluminoxane, or combinations thereof.

Aspect 156. The process for making an aviation fuel according to any of the preceding Aspects, wherein the first catalyst system, the second catalyst system, or both catalyst systems independently comprise a diluent.

Aspect 157. The process for making an aviation fuel according to Aspect 156, wherein the diluent comprises, consists essentially of, or is selected from a hydrocarbon, a halogenated hydrocarbon, or combinations thereof.

Aspect 158. The process for making an aviation fuel according to any of Aspects 156-157, wherein the diluent comprises, consists essentially of, or is selected from a cyclic diluent, an acyclic diluent, or combinations thereof.

Aspect 159. The process for making an aviation fuel according to any of Aspects 156-158, wherein the diluent comprises, consists essentially of, or is selected from a linear diluent, a branched diluent, or combinations thereof.

Aspect 160. The process for making an aviation fuel according to any of Aspects 156-159, wherein the diluent comprises, consists essentially of, or is selected from aliphatic hydrocarbons, aromatic hydrocarbons, petroleum distillates, halogenated aliphatic hydrocarbons, halogenated aromatic hydrocarbons, or combinations thereof.

Aspect 161. The process for making an aviation fuel according to any of Aspects 156-160, wherein the diluent comprises, consists essentially of, or is selected from a $C_3$ to $C_8$ linear or branched acyclic aliphatic hydrocarbon, $C_6$ to $C_{10}$ aromatic hydrocarbons, $C_1$ to $C_{15}$ halogenated aliphatic hydrocarbons, $C_1$ to $C_{10}$ halogenated aliphatic hydrocarbons, $C_1$ to $C_5$ halogenated aliphatic hydrocarbons, $C_6$ to $C_{20}$ halogenated aromatic hydrocarbons, $C_6$ to $C_{10}$ halogenated aromatic hydrocarbons, or combinations thereof.

Aspect 162. The process for making an aviation fuel according to any of Aspects 156-161, wherein the diluent comprises, consists essentially of, or is selected from a propane, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), hexane (n-hexane or mixture of linear and branched $C_6$ acyclic aliphatic hydrocarbons), heptane (n-heptane or a mixture of linear and branched $C_7$ acyclic aliphatic hydrocarbons), octane (n-octane or a mixture of linear and branched $C_8$ acyclic aliphatic hydrocarbons), cyclohexane, methyl cyclohexane, benzene, toluene, xylene (including ortho-xylene, meta-xylene, para-xylene, or mixtures thereof), ethylbenzene, methylene chloride, chloroform, carbon tetrachloride, dichloroethane, trichloroethane, chlorobenzene, dichlorobenzene, or combinations thereof.

Aspect 163. The process for making an aviation fuel according to any of the preceding Aspects, wherein the biomass ethanol is produced from a starch-based feedstock, a sugar-based feedstock, or a cellulosic feedstock, or is produced from a bio-syngas to ethanol process.

Aspect 164. The process for making an aviation fuel according to Aspect 163, wherein the biomass ethanol is produced by the fermentation of sugars derived from a starch-based feedstock or a sugar-based feedstock.

Aspect 165. The process for making an aviation fuel according to Aspect 163, wherein the biomass ethanol is produced by the fermentation of a carbohydrate derived from a starch-based feedstock, a sugar-based feedstock, or a cellulosic feedstock.

Aspect 166. The process for making an aviation fuel according to any of Aspects 163-165, wherein the starch-based feedstock comprises barley, cassava root, corn, potato, rice, sorghum grain, sweet potato, wheat, rye, or any combination thereof.

Aspect 167. The process for making an aviation fuel according to any of Aspects 163-166, wherein the sugar-based feedstock comprises sugar cane, sugar beet, sweet sorghum, molasses, fruit, or any combination thereof.

Aspect 168. The process for making an aviation fuel according to any of Aspects 163-166, wherein the biomass ethanol is produced from a starch-based feedstock by a process comprising the enzymatic hydrolysis of the starch-based feedstock to produce sugars, followed by yeast fermentation of the sugars.

Aspect 169. The process for making an aviation fuel according to Aspect 163, wherein the biomass ethanol is produced from cellulosic feedstock.

Aspect 170. The process for making an aviation fuel according to Aspect 164, wherein the cellulosic feedstock comprises corn stover, wheat straw, sugar cane bagasse, switchgrass, or wood chips.

Aspect 171. The process for making an aviation fuel according to any of the preceding Aspects, wherein dehydration of the biomass ethanol comprising contacting the biomass ethanol with a dehydration catalyst under conditions suitable to form bio-ethylene.

Aspect 172. The process for making an aviation fuel according to Aspect 171, wherein dehydration of the biomass ethanol comprises passing liquid phase ethanol through a bed comprising the dehydration catalyst.

Aspect 173. The process for making an aviation fuel according to any of Aspects 171-172, further comprising regenerating the dehydration catalyst by heating at atmosphere pressure or at reduced pressure.

Aspect 174. The process for making an aviation fuel according to any of Aspects 171-173, wherein the dehydration catalyst comprises, consists essentially of, or is alumina, silica gel, silica-alumina, a crystalline silicate, a dealuminated crystalline silicate, a phosphorus-modified crystalline silicate, a zeolite, a molecular sieve, or anhydrous calcium sulfate.

Aspect 175. The process for making an aviation fuel according to any of Aspects 171-174, wherein the dehydration catalyst comprises, consists essentially of, or is a lanthanum-modified H-ZSM-catalyst, a ZSM-5/SAPO-34 composite, a mordenite catalyst, microspherical SAPO-34 catalyst, a phosphorus-modified HZSM-5 catalyst, a lanthanum-phosphorous modified HZSM-5 catalyst, a gallium-modified zeolite, a gallium-modified SAPO-11, a gallium-modified HZSM-5, a ZSM-based catalyst, a heteropolyacid catalyst, or a supported heteropolyacid catalyst.

Aspect 176. The process for making an aviation fuel according to any of Aspects 171-175, wherein the dehydration catalyst comprises, consists essentially of, or is a ZSM-5 zeolite comprising from 0.1 wt. % to 0.5 wt. % of lanthanum and from 0.01 wt. % to 1 wt. % phosphorous, relative to the weight of the catalyst, wherein the ZSM-5 has a silica to alumina molar ratio of 20 to 45.

Aspect 177. The process for making an aviation fuel according to any of the preceding Aspects, wherein the first hydrogenation catalyst, the second hydrogenation catalyst, or both independently comprise, consist essentially of, or are selected from a nickel or a nickel-containing catalyst, a platinum or a platinum-containing catalyst, or a palladium or a palladium-containing catalyst.

Aspect 178. The process for making an aviation fuel according to any of the preceding Aspects, wherein the first hydrogenation catalyst, the second hydrogenation catalyst, or both independently comprise, consist essentially of, or are selected from (a) a heterogeneous catalyst selected from a Group 8-12 metal deposited on a carrier selected from carbon, silica, alumina, silica-alumina, a zeolite, or calcium carbonate; or (b) a homogeneous catalysts selected from (i) a Ziegler catalyst comprising an organic salt of a Group 6-10 metal and an organoaluminum compound, or (ii) a coordination compound of Ru, Rh, or Ir, or (iii) a Group 4 metal organometallic compound.

Aspect 179. The process for making an aviation fuel according to Aspect 178, wherein (a) the Group 8-12 metal of the heterogeneous catalysts is selected from Fe, Co, Ni, Cu, Zn, Ru, Rh, Pd, Ir, or Pt; (b) the Group 6-10 metal of the homogeneous catalyst is selected from Ni, Co, Fe, or Cr; or (c) the Group 4 metal organometallic compound is selected from a Group 4 metallocene compound.

Aspect 180. The process for making an aviation fuel according to any of the preceding Aspects, wherein the first hydrogenation catalyst, the second hydrogenation catalyst, or both independently comprise one or more metals selected from cobalt, molybdenum, nickel, or tungsten.

Aspect 181. The process for making an aviation fuel according to any of the preceding Aspects, wherein a portion of the ethylene feed can be a bio-ethylene feed, and the contacting the ethylene feed with the first catalyst system occurs at a total pressure of from 0 psig (0 KPa) to 2,500 psig (17.3 MPa); alternatively, from 0 psig (KPa) to 1,600 psig (11.0 MPa); alternatively, from 0 psig (KPa) to 1,500 psig (10.4 MPa); alternatively, from 50 psig (344 KPa) to 2,500 psig (17.3 MPa); alternatively, from 100 psig (689 KPa) to 2,500 psig (17.3 MPa); alternatively, from 150 psig (1.0 MPa) to 2,000 psig (13.8 MPa); or alternatively, from 300 psig (2.0 MPa) to 900 psig (6.2 MPa).

Aspect 182. The process for making an aviation fuel according to any of the preceding Aspects, wherein at least a portion of the ethylene feed is a bio-ethylene feed, and the contacting the ethylene feed with the first catalyst system occurs at a bio-ethylene feed pressure of from 0 psig (0 KPa) to 2,500 psig (17.3 MPa); alternatively, from 50 psig (344 KPa) to 2,500 psig (17.3 MPa); alternatively, from 100 psig (689 KPa) to 2,500 psig (17.3 MPa); or alternatively, from 150 psig (1.0 MPa) to 2,000 psig (13.8 MPa).

Aspect 183. The process for making an aviation fuel according to any of the preceding Aspects, wherein a portion of the ethylene feed can be a bio-ethylene feed, and the contacting the ethylene feed with the first catalyst system occurs at a temperature of at least 0° C.; alternatively, at least 10° C.; alternatively, at least 20° C.; alternatively, at least 30° C.; alternatively, at least 40° C.; alternatively, at least 50° C.; alternatively, at least 60° C.; alternatively, at least 70° C.; alternatively, at least 80° C.; alternatively, at least 90° C.; alternatively, at least 100° C.; alternatively, at least 110° C.; alternatively, at least 120° C.; alternatively, at least 130° C.; alternatively, at least 140° C.; alternatively, at least 150° C.; alternatively, at least 160° C.; alternatively, at least 170° C.; or alternatively, at least 180° C.

Aspect 184. The process for making an aviation fuel according to any of the preceding Aspects, wherein a portion of the ethylene feed can be a bio-ethylene feed, and the contacting the ethylene feed with the first catalyst system occurs at a temperature of less than 180° C.; alternatively, less than 160° C.; alternatively, less than 140° C.; alternatively, less than 120° C.; alternatively, less than 100° C.; alternatively, less than 90° C.; or alternatively, less than 80° C.

Aspect 185. The process for making an aviation fuel according to any of the preceding Aspects, wherein a portion of the ethylene feed can be a bio-ethylene feed, and the contacting the ethylene feed with the first catalyst system occurs at a temperature within a range of from 0° C. to 180° C.; alternatively, from 10° C. to 160° C.; alternatively, from 20° C. to 140° C.; alternatively, from 30° C. to 120° C.; alternatively, from 40° C. to 100° C.; alternatively, from 50° C. to 100° C.; or alternatively, from 60° C. to 140° C.

Aspect 186. A composition comprising 2,2-dimethyl-4-butyl-3-octene, 2,2-dimethyl-5-propyl-3-nonene, 2,2-dimethyl-6-ethyl-3-decene, and 2,2,7-trimethyl-3-undecene.

Aspect 187. A composition comprising any combination of 2,2-dimethyl-4-butyl-3-octene, 2,2-dimethyl-5-propyl-3-nonene, 2,2-dimethyl-6-ethyl-3-decene, and 2,2,7-trimethyl-3-undecene.

Aspect 188. A composition comprising 5-(2,2-dimethylpropyl)nonane, 2,2-dimethyl-5-propylnonane, 2,2-dimethyl-6-ethyl-decane, and 2,2,7-trimethylundecane.

Aspect 189. A composition comprising any combination of 5-(2,2-dimethylpropyl)nonane, 2,2-dimethyl-5-propylnonane, 2,2-dimethyl-6-ethyl-decane, and 2,2,7-trimethylundecane.

Aspect 190. A composition comprising 2-methyl-4-butyl-3-octene, 2-methyl-5-propylnon-3-ene, 6-ethyl-2-methyldec-3-ene, and 2,7-dimethylundec-3-ene.

Aspect 191. A composition comprising any combination of 2-methyl-4-butyl-3-octene, 2-methyl-5-propylnon-3-ene, 6-ethyl-2-methyldec-3-ene, and 2,7-dimethylundec-3-ene.

Aspect 192. A composition comprising 5-isobutylnonane, 2-methyl-5-propylnonane, 6-ethyl-2-methyldecane, and 2,7-dimethylundecane.

Aspect 193. A composition comprising any combination of 5-isobutylnonane, 2-methyl-5-propylnonane, 6-ethyl-2-methyldecane, and 2,7-dimethylundecane.

Aspect 194. A composition comprising 5-butyl-3-methylnon-4-ene, 3-methyl-6-propyldec-4-ene, 7-ethyl-3-methylundec-4-ene, and 3,8-dimethyldodec-4-ene.

Aspect 195. A composition comprising any combination of 5-butyl-3-methylnon-4-ene, 3-methyl-6-propyldec-4-ene, 7-ethyl-3-methylundec-4-ene, and 3,8-dimethyldodec-4-ene.

Aspect 196. A composition comprising 5-butyl-3-methylnonane, 3-methyl-6-propyldecane, 7-ethyl-3-methylundecane, and 3,8-dimethyldodecane.

Aspect 197. A composition comprising any combination of 5-butyl-3-methylnonane, 3-methyl-6-propyldecane, 7-ethyl-3-methylundecane, and 3,8-dimethyldodecane.

Aspect 198. A composition comprising 6-butyl-4-methyldec-5-ene, 4-methyl-7-propylundec-5-ene, 8-ethyl-4-methyldodec-5-ene, and 4,9-dimethyltridec-5-ene.

Aspect 199. A composition comprising any combination of 6-butyl-4-methyldec-5-ene, 4-methyl-7-propylundec-5-ene, 8-ethyl-4-methyldodec-5-ene, and 4,9-dimethyltridec-5-ene.

Aspect 200. A composition comprising 6-butyl-4-methyldecane, 4-methyl-7-propylundecane, 8-ethyl-4-methyldodecane, and 4,9-dimethyltridecane.

Aspect 201. A composition comprising any combination of 6-butyl-4-methyldecane, 4-methyl-7-propylundecane, 8-ethyl-4-methyldodecane, and 4,9-dimethyltridecane.

Aspect 202. A composition comprising 5-butyl-7-methylundec-5-ene, 5-methyl-8-propyldodec-6-ene, 9-ethyl-5-methyltridec-6-ene, and 5,10-dimethyltetradec-6-ene.

Aspect 203. A composition comprising any combination of 5-butyl-7-methylundec-5-ene, 5-methyl-8-propyldodec-6-ene, 9-ethyl-5-methyltridec-6-ene, and 5,10-dimethyltetradec-6-ene.

Aspect 204. A composition comprising 5-butyl-7-methylundecane, 5-methyl-8-propyldodecane, 5-ethyl-9-methyltridecane, and 5,10-dimethyltetradecane.

Aspect 205. A composition comprising any combination of 5-butyl-7-methylundecane, 5-methyl-8-propyldodecane, 5-ethyl-9-methyltridecane, and 5,10-dimethyltetradecane.

Aspect 206. A composition comprising 3-butyl-2-heptene, 4-propyl-2-octene, 5-ethyl-2-nonene, and 6-methyl-2-decene.

Aspect 207. A composition comprising any combination of 3-butyl-2-heptene, 4-propyl-2-octene, 5-ethyl-2-nonene, and 6-methyl-2-decene.

Aspect 208. A composition comprising 5-ethylnonane, 4-propyloctane, and 5-methyldecane.

Aspect 209. A composition comprising any combination of 5-ethylnonane, 4-propyloctane, and 5-methyldecane.

Aspect 210. A composition comprising 4-butyl-3-octene, 5-propyl-3-nonene, 6-ethyl-3-decene, and 7-methyl-3-undecene.

Aspect 211. A composition comprising any combination of 4-butyl-3-octene, 5-propyl-3-nonene, 6-ethyl-3-decene, and 7-methyl-3-undecene.

Aspect 212. A composition comprising 5-propylnonane, 5-ethyldecane, and 5-methylundecane.

Aspect 213. A composition comprising any combination of 5-propylnonane, 5-ethyldecane, and 5-methylundecane.

Aspect 214. A composition comprising 2-methyl-4-propyloct-2-ene, 5-ethyl-2-methylnon-2-ene, and 2,6-dimethyldec-2-ene.

Aspect 215. A composition comprising any combination of 2-methyl-4-propyloct-2-ene, 5-ethyl-2-methylnon-2-ene, and 2,6-dimethyldec-2-ene.

Aspect 216. A composition comprising 2-methyl-4-propyloctane, 5-ethyl-2-methylnonane, and 2,6-dimethyldecane.

Aspect 217. A composition comprising any combination of 2-methyl-4-propyloctane, 5-ethyl-2-methylnonane, and 2,6-dimethyldecane.

Aspect 218. A composition comprising 5-butyl-4-nonene, 6-propyl-4-decene, 7-ethyl-4-undecene, and 8-methyl-4-dodecene.

Aspect 219. A composition comprising any combination of 5-butyl-4-nonene, 6-propyl-4-decene, 7-ethyl-4-undecene, and 8-methyl-4-dodecene.

Aspect 220. A composition comprising 5-butylnonane, 5-propyldecane, 5-ethylundecane, and 5-methyldodecane.

Aspect 221. A composition comprising any combination of 5-butylnonane, 5-propyldecane, 5-ethylundecane, and 5-methyldodecane.

Aspect 222. A composition comprising 5-butyldec-5-ene, 7-propylundec-5-ene, 8-ethyldodec-5-ene, and 9-methyltridec-5-ene.

Aspect 223. A composition comprising any combination of 5-butyldec-5-ene, 7-propylundec-5-ene, 8-ethyldodec-5-ene, and 9-methyltridec-5-ene.

Aspect 224. A composition comprising 5-butyldecane, 5-propylundecane, 5-ethyldodecane, and 5-methyltridecane.

Aspect 225. A composition comprising any combination of 5-butyldecane, 5-propylundecane, 5-ethyldodecane, and 5-methyltridecane.

Aspect 226. A composition comprising 5-(2,2-dimethylpropylidene)nonane, 2,2-dimethyl-5-propylnon-3-ene, 6-ethyl-2,2-dimethyldec-3-ene, and 2,2,7-trimethylundec-3-ene.

Aspect 227. A composition comprising any combination of 5-(2,2-dimethylpropylidene)nonane, 2,2-dimethyl-5-propylnon-3-ene, 6-ethyl-2,2-dimethyldec-3-ene, and 2,2,7-trimethylundec-3-ene.

Aspect 228. A composition comprising 5-neopentylnonane, 2,2-dimethyl-5-propylnonane, 6-ethyl-2,2-dimethyldecane, and 2,2,7-trimethylundecane.

Aspect 229. A composition comprising any combination of 5-neopentylnonane, 2,2-dimethyl-5-propylnonane, 6-ethyl-2,2-dimethyldecane, and 2,2,7-trimethylundecane.

Aspect 230. A composition comprising 5-butyldodec-5-ene, 5-propyltridec-6-ene, 5-ethyltetradec-7-ene, and 11-methylpentadec-7-ene.

Aspect 231. A composition comprising any combination of 5-butyldodec-5-ene, 5-propyltridec-6-ene, 5-ethyltetradec-7-ene, and 11-methylpentadec-7-ene.

Aspect 232. A composition comprising 5-butyldodecane, 5-propyltridecane, 5-ethyltetradecane, and 5-methylpentadecane.

Aspect 233. A composition comprising any combination of 5-butyldodecane, 5-propyltridecane, 5-ethyltetradecane, and 5-methylpentadecane.

We claim:

1. A process for making a $C_{16}$-olefin stream, the process comprising:

(a) contacting an ethylene feed with a first catalyst system comprising a first oligomerization catalyst to form an oligomerization product comprising at least one $C_4$-$C_8$ alpha-olefin and a mixture of decenes;

(b) separating the mixture of decenes from the oligomerization product;

(c) contacting the mixture of decenes with at least one $C_{6-}$ alpha-olefin in the presence of a second catalyst system comprising a second oligomerization catalyst to provide the $C_{16-}$ olefin stream;

(d) optionally, hydrogenating the $C_{16-}$ olefin stream in the presence of a first hydrogenation catalyst to provide $C_{16-}$ paraffins; and (e) optionally, blending the $C_{16-}$ paraffins as a component to form an aviation fuel.

2. The process of claim 1, wherein the at least one $C_{6-}$ alpha-olefin comprises propylene, 1-butene, isobutylene, 1-pentene, 1-hexene, or a combination thereof.

3. The process of claim 1, wherein the mixture of decenes comprises 1-decene, 2-butyl-1-hexene, 3-propyl-1-heptene, 4-ethyl-1-octene, 5-methyl-1-nonene, 4-decene, 5-decene, or any combination thereof.

4. The process of claim 3, wherein the mixture of decenes comprises from 76 mol % to 95 mol % $C_{10}$ monoolefins.

5. The process of claim 1, wherein the oligomerization product comprises 1-butene, 1-hexene, 1-octene, dodecenes, tetradecenes, or any combination thereof.

6. The process of claim 1, wherein the oligomerization product comprises:

at least 60 mol % 1-hexene, at least 60 mol % 1-octene, or at least 60 mol % 1-hexene and 1-octene combined; or from 70 wt. % to 99.8 wt. % hexene or from 70 wt. % to 99.8 wt. % octene, and at least 0.2 wt. % of the mixture of decenes.

7. The process of claim 1, wherein the first catalyst system, the second catalyst system, or both comprise independently a chromium-based catalyst, a metallocene-based catalyst, a Ziegler-Natta based catalyst, a metal-oxide supported Group 6-10 transition metal-based catalyst, or a combination thereof.

8. The process of claim 7, wherein the first catalyst system, the second catalyst system, or both further comprise a metal alkyl compound selected from an organoaluminum compound, an organoaluminoxane, an organoboron compound, an organozinc compound, an organomagnesium compound, an organolithium compound, or any combination thereof.

9. The process of claim 1, wherein the first catalyst system, the second catalyst system, or both comprise independently a chromium-based catalyst, and the chromium-based catalyst comprises (a) a chromium-containing compound, (b) a heteroatomic ligand, (c) a metal alkyl compound, and (d) optionally, a diluent.

10. The process of claim 9, wherein the heteroatomic ligand is selected from a pyrrole compound, a diphosphino aminyl compound, an $N^2$-phosphinyl amidine compound, an $N^2$-phosphinyl formamidine compound, or combinations thereof.

11. The process of claim 10, wherein the diluent is present and comprises a hydrocarbon, a halogenated hydrocarbon, or combinations thereof.

12. The process of claim 1, wherein the first catalyst system, the second catalyst system, or both independently comprise:

(a) molybdenum oxide on alumina ($MoO_3/Al_2O_3$), tungsten oxide on silica ($WO_3/SiO_2$), tungsten oxide on silica-alumina ($WO_3/SiO_2/Al_2O_3$), rhenium oxide on alumina ($Re_2O_7/Al_2O_3$), cobalt oxide and molybdenum oxide on alumina ($CoO/MoO_3/Al_2O_3$), rhenium oxide on alumina activated with tetramethyl tin ($Re_2O_7/Al_2O_3/SnMe_4$), or any combination thereof; or (b) tungstated zirconium, molybdenum zirconium, nickel and/or cobalt doped tungstated zirconium, nickel and/or cobalt doped molybdenum zirconium catalysts, a Group 3 to Group 12 metal-treated zeolite, or combinations thereof.

13. The process of claim 1, wherein the first hydrogenation catalyst comprises:

(a) a heterogeneous catalyst selected from a Group 8-12 metal deposited on a carrier selected from carbon, silica, alumina, silica-alumina, a zeolite, or calcium carbonate; or (b) a homogeneous catalyst selected from (i) a Ziegler catalyst comprising an organic salt of a Group 6-10 metal and an organoaluminum compound, or (ii) a coordination compound of Ru, Rh, or Ir, or (iii) a Group 4 metal organometallic compound.

14. The process of claim 1, wherein the $C_{16-}$ olefin stream comprises:

(1) 2-methyl-4-butyl-3-octene, 2-methyl-5-propylnon-3-ene, 6-ethyl-2-methyldec-3-ene, and/or 2,7-dimethylundec-3-ene;

(2) 5-butyl-3-methylnon-4-ene, 3-methyl-6-propyldec-4-ene, 7-ethyl-3-methylundec-4-ene, and/or 3,8-dimethyldodec-4-ene;

(3) 2,2-dimethyl-4-butyl-3-octene, 2,2-dimethyl-5-propyl-3-nonene, 2,2-dimethyl-6-ethyl-3-decene, and/or 2,2,7-trimethyl-3-undecene;

(4) 6-butyl-4-methyldec-5-ene, 4-methyl-7-propylundec-5-ene, 8-ethyl-4-methyldodec-5-ene, and/or 4,9-dimethyltridec-5-ene; or (5) 5-butyl-7-methylundec-5-ene, 5-methyl-8-propyldodec-6-ene, 9-ethyl-5-methyltridec-6-ene, and/or 5,10-dimethyltetradec-6-ene.

15. The process of claim 1, wherein:

at least a portion of the ethylene feed is a bio-ethylene feed; and the aviation fuel is formed and is a sustainable aviation fuel.

16. The process of claim 15, wherein:

(a) the sustainable aviation fuel is certified as compliant with the Carbon Offsetting and Reduction Scheme for International Aviation (CORSIA) sustainability criteria in accordance with the International Sustainability and Carbon Certification (ISCC) CORSIA certification system; or (b) the sustainable aviation fuel is certified as a Lower Carbon Aviation Fuel (LCAF) in accordance with the International Sustainability and Carbon Certification (ISCC) LCAF certification system;

wherein the certification is based upon the weight or fraction of the sustainable aviation fuel attributable to the biomass ethanol determined by mass balance and a free attribution method.

* * * * *